US012655213B2

(12) United States Patent
Lohmueller et al.

(10) Patent No.: US 12,655,213 B2
(45) Date of Patent: Jun. 16, 2026

(54) COVALENT ADAPTOR SYNNOTCH AND CHIMERIC ANTIGEN RECEPTORS (CARS) FOR PROGRAMMABLE ANTIGEN-TARGETING

(71) Applicant: UNIVERSITY OF PITTSBURGH-OF THE COMMONWEALTH SYSTEM OF HIGHER EDUCATION, Pittsburgh, PA (US)

(72) Inventors: Jason Jakob Lohmueller, Pittsburgh, PA (US); Alexander Deiters, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 1362 days.

(21) Appl. No.: 17/282,113

(22) PCT Filed: Oct. 3, 2019

(86) PCT No.: PCT/US2019/054479
§ 371 (c)(1),
(2) Date: Apr. 1, 2021

(87) PCT Pub. No.: WO2020/072764
PCT Pub. Date: Apr. 9, 2020

(65) Prior Publication Data
US 2022/0267435 A1     Aug. 25, 2022

Related U.S. Application Data

(60) Provisional application No. 62/740,801, filed on Oct. 3, 2018.

(51) Int. Cl.
| | |
|---|---|
| *C07K 16/28* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 14/725* | (2006.01) |
| *C12N 9/10* | (2006.01) |
| *C12N 9/96* | (2006.01) |
| *A61K 38/00* | (2006.01) |

(52) U.S. Cl.
CPC .......... *C07K 16/2803* (2013.01); *A61K 40/11* (2025.01); *A61K 40/31* (2025.01); *A61K 40/4202* (2025.01); *A61K 40/4204* (2025.01); *A61K 40/4211* (2025.01); *A61P 35/00* (2018.01); *C07K 14/705* (2013.01); *C07K 14/7051* (2013.01); *C07K 14/70517* (2013.01); *C07K 14/70578* (2013.01); *A61K 38/00* (2013.01); *A61K 2239/48* (2023.05); *C07K 2317/76* (2013.01); *C07K 2319/02* (2013.01);

*C07K 2319/03* (2013.01); *C07K 2319/33* (2013.01); *C07K 2319/40* (2013.01); *C12N 9/1007* (2013.01); *C12N 9/96* (2013.01)

(58) Field of Classification Search
CPC .............. C07K 16/2803; C07K 14/705; C07K 14/7051; C07K 14/70517; C07K 14/70578; C07K 2317/76; C07K 2319/02; C07K 2319/03; C07K 2319/33; C07K 2319/40; C07K 2319/50; C07K 2319/71; C07K 2319/90; C07K 16/2863; C07K 16/2887; C07K 16/32; C07K 2317/24; C07K 2317/622; A61K 40/11; A61K 40/31; A61K 40/4202; A61K 40/4204; A61K 40/4211; A61K 38/00; A61K 2239/48; A61P 35/00
See application file for complete search history.

(56) References Cited

U.S. PATENT DOCUMENTS

| | | | |
|---|---|---|---|
| 2016/0129109 A1 | 5/2016 | Davila et al. | |
| 2017/0081411 A1 | 3/2017 | Boris et al. | |
| 2017/0198308 A1 | 7/2017 | Qi et al. | |
| 2018/0079812 A1 | 3/2018 | Lim et al. | |
| 2023/0414754 A1* | 12/2023 | Lohmueller | ....... C07K 16/2803 |

FOREIGN PATENT DOCUMENTS

| | | | | |
|---|---|---|---|---|
| WO | 2015142661 | 9/2015 | | |
| WO | WO-2017032777 A1 * | 3/2017 | ........... | A61K 31/436 |
| WO | 2017112784 | 6/2017 | | |
| WO | WO-2017091546 A1 * | 6/2017 | ......... | A61K 39/0011 |
| WO | WO-2017112784 A1 * | 6/2017 | ............. | A61K 35/12 |
| WO | 2018/053180 | 3/2018 | | |

(Continued)

OTHER PUBLICATIONS

Zhao Y, et al. A herceptin-based chimeric antigen receptor with modified signaling domains leads to enhanced survival of transduced T lymphocytes and antitumor activity. J Immunol. Nov. 1, 2009;183(9):5563-74. doi: 10.4049/jimmunol.0900447. PMID: 19843940; PMCID: PMC6292203. (Year: 2009).*

(Continued)

*Primary Examiner* — Maher M Haddad
*Assistant Examiner* — Alec Jon Peters
(74) *Attorney, Agent, or Firm* — Meunier Carlin & Curfman LLC

(57) ABSTRACT

Disclosed are compositions and methods related to the construction and use of universal synthetic notch (synNotch) receptors and chimeric antigen receptor (CAR) T cells.

Figure 1A:
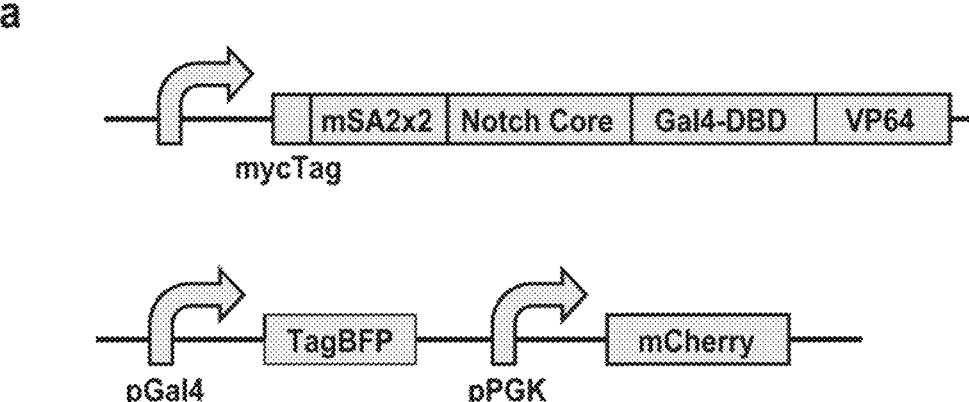

10 Claims, 17 Drawing Sheets
Specification includes a Sequence Listing.

(56)          References Cited

FOREIGN PATENT DOCUMENTS

WO          2019152957          8/2019

OTHER PUBLICATIONS

Cole NB. Site-specific protein labeling with SNAP-tags. Curr Protoc Protein Sci. Sep. 24, 2013;73:30.1.1-30.1.16. doi: 10.1002/0471140864.ps3001s73. PMID: 24510614; PMCID: PMC3920298. (Year: 2013).*

Bedbrook CN, et al. Genetically Encoded Spy Peptide Fusion System to Detect Plasma Membrane-Localized Proteins In Vivo. Chem Biol. Aug. 20, 2015;22(8):1108-21. doi: 10.1016/j.chembiol. 2015.06.020. Epub Jul. 23, 2015. PMID: 26211362; PMCID: PMC4546540. (Year: 2015).*

Minutolo N, et al. Redirecting gene-engineered T cells through covalent attachment of targeting ligands to a universal immune receptor. Journal for ImmunoTherapy of Cancer 2016, 4(Suppl 1):P31 (Year: 2016).*

Minutolo NG, et al. Quantitative Control of Gene-Engineered T-Cell Activity through the Covalent Attachment of Targeting Ligands to a Universal Immune Receptor. J Am Chem Soc. Apr. 8, 2020;142(14):6554-6568. doi: 10.1021/jacs.9b11622. Epub Mar. 30, 2020. PMID: 32191035; PMCID: PMC7306176. (Year: 2020).*

Ruffo, E., et al. Post-translational covalent assembly of CAR and synNotch receptors for programmable antigen targeting. Nat Commun 14, 2463 (2023). https://doi.org/10.1038/s41467-023-37863-5 (Year: 2023).*

Reymond L, et al. Visualizing biochemical activities in living cells through chemistry. Chimia (Aarau). 2011;65(11):868-71. doi: 10.2533/chimia.2011.868. PMID: 22289374. (Year: 2011).*

European Search Report issued for Appliation No. EP19868652, dated Aug. 16, 2022.

Extended European Search Report issued for Appliation No. EP19868652, dated Nov. 17, 2022.

Lomueller, Jason Jakob, et al. "Covalent adaptor synNotch and chimeric antigen receptors (CARs) for programmable antigen targeting." (2019): 71-18.

Andersen, P. S. et al. Quantifying the energetics of cooperativity in a ternary protein complex. Biochemistry 41, 5177-5184, doi:10.1021/bi0200209 (2002).

Cho, J. H., Collins, J. J. & Wong, W. W. Universal Chimeric Antigen Receptors for Multiplexed and Logical Control of T Cell Responses. Cell 173, 1426-1438 e1411, doi:10.1016/j.cell.2018.03.038 (2018).

Chudasama, V. L. et al. Simulations of site-specific target-mediated pharmacokinetic models for guiding the development of bispecific antibodies. J Pharmacokinet Pharmacodyn 42, 1-18, doi:10.1007/s10928-014-9401-1 (2015).

De Lean, A., Stadel, J. M. & Lefkowitz, R. J. A ternary complex model explains the agonist-specific binding properties of the adenylate cyclase-coupled beta-adrenergic receptor. J Biol Chem 255, 7108-7117 (1980).

Doldan-Martelli, V., Guantes, R. & Miguez, D. G. A mathematical model for the rational design of chimeric ligands in selective drug therapies. CPT Pharmacometrics Syst Pharmacol 2, e26, doi:10.1038/psp.2013.2 (2013).

Douglass, E. F., Jr., Miller, C. J., Sparer, G., Shapiro, H. & Spiegel, D. A. A comprehensive mathematical model for three-body binding equilibria. J Am Chem Soc 135, 6092-6099, doi:10.1021/ja311795d (2013).

Eric Jones, T. O., Pearu Peterson. SciPy: Open Source Scientific Tools for Python (2001).

Esensten, J. H., Bluestone, J. A. & Lim, W. A. Engineering Therapeutic T Cells: From Synthetic Biology to Clinical Trials. Annu Rev Pathol 12, 305-330, doi:10.1146/annurev-pathol-052016-100304 (2017).

Gautier, A. et al. An engineered protein tag for multiprotein labeling in living cells. Chem Biol 15, 128-136, doi:10.1016/j.chembiol. 2008.01.007 (2008).

Gross, G., Waks, T. & Eshhar, Z. Expression of immunoglobulin-T-cell receptor chimeric molecules as functional receptors with antibody-type specificity. Proc Natl Acad Sci U S A 86, 10024-10028, doi:10.1073/pnas.86.24.10024 (1989).

June, C. H. & Sadelain, M. Chimeric Antigen Receptor Therapy. N Engl J Med 379, 64-73, doi:10.1056/NEJMra1706169 (2018).

Keppler, A. et al. A general method for the covalent labeling of fusion proteins with small molecules in vivo. Nat Biotechnol 21, 86-89, doi:10.1038/nbt765 (2003).

Kershaw, M. H. et al. A phase I study on adoptive immunotherapy using gene-modified T cells for ovarian cancer. Clinical cancer research : an official journal of the American Association for Cancer Research 12, 6106-6115, doi:10.1158/1078-0432.CCR-06-1183 (2006).

Kudo, K. et al. T lymphocytes expressing a CD16 signaling receptor exert antibody-dependent cancer cell killing. Cancer research 74, 93-103, doi:10.1158/0008-5472.CAN-13-1365 (2014).

Lamers, C. H. et al. Treatment of metastatic renal cell carcinoma with autologous T-lymphocytes genetically retargeted against carbonic anhydrase IX: first clinical experience. J Clin Oncol 24, e20-22, doi:10.1200/JCO.2006.05.9964 (2006).

Lim, K. H., Huang, H., Pralle, A. & Park, S. Stable, high-affinity streptavidin monomer for protein labeling and monovalent biotin detection. Biotechnol Bioeng 110, 57-67, doi:10.1002/bit.24605 (2013).

Lohmueller, J. & Finn, O. J. Current modalities in cancer immunotherapy: Immunomodulatory antibodies, CARs and vaccines. Pharmacol Ther 178, 31-47, doi:10.1016/j.pharmthera.2017. 03.008 (2017).

Lohmueller, J. J. et al. Antibodies elicited by the first non-viral prophylactic cancer vaccine show tumor-specificity and immunotherapeutic potential. Sci Rep 6, 31740, doi:10.1038/srep31740 (2016).

Lohmueller, J. J., Ham, J. D., Kvorjak, M. & Finn, O. J. mSA2 affinity-enhanced biotin-binding CAR T cells for universal tumor targeting. Oncoimmunology 7, e1368604, doi:10.1080/2162402X. 2017.1368604 (2017).

Los, G. V. et al. HaloTag: a novel protein labeling technology for cell imaging and protein analysis. ACS Chem Biol 3, 373-382, doi:10.1021/cb800025k (2008).

Lu, C. & Wang, Z. X. Quantitative Analysis of Ligand Induced Heterodimerization of Two Distinct Receptors. Anal Chem 89, 6926-6930, doi:10.1021/acs.analchem.7b01274 (2017).

Ma, J. S. et al. Versatile strategy for controlling the specificity and activity of engineered T cells. Proc Natl Acad Sci U S A 113, E450-458, doi:10.1073/pnas.1524193113 (2016).

Mackall, C. L., Fry, T. J. & Gress, R. E. Harnessing the biology of IL-7 for therapeutic application. Nat Rev Immunol 11, 330-342, doi:10.1038/nri2970 (2011).

Maloney, D. G. et al. IDEC-C2B8 (Rituximab) anti-CD20 monoclonal antibody therapy in patients with relapsed low-grade non-Hodgkin's lymphoma. Blood 90, 2188-2195 (1997).

Maude, S. L. et al. Chimeric antigen receptor T cells for sustained remissions in leukemia. N Engl J Med 371, 1507-1517, doi:10. 1056/NEJMoa1407222 (2014).

Maus, M. V. et al. T cells expressing chimeric antigen receptors can cause anaphylaxis in humans. Cancer Immunol Res 1, 26-31, doi:10.1158/2326-6066.CIR-13-0006 (2013).

Morsut, L. et al. Engineering Customized Cell Sensing and Response Behaviors Using Synthetic Notch Receptors. Cell 164, 780-791, doi:10.1016/j.cell.2016.01.012 (2016).

Otsuki, J., Narita, T., Tsutsumida, K., Takatsuki, M. & Kaneko, M. Modular approach toward supramolecular functional assemblies: characterization of Donor-spacer-acceptor ternary complexes. J Phys Chem A 109, 6128-6134, doi:10.1021/jp051012f (2005).

Porter, D. L., Levine, B. L., Kalos, M., Bagg, A. & June, C. H. Chimeric antigen receptor-modified T cells in chronic lymphoid leukemia. N Engl J Med 365, 725-733, doi:10.1056/NEJMoa1103849 (2011).

Rodgers, D. T. et al. Switch-mediated activation and retargeting of CAR-T cells for B-cell malignancies. Proc Natl Acad Sci U S A 113, E459-468, doi:10.1073/pnas.1524155113 (2016).

(56)              References Cited

OTHER PUBLICATIONS

Roybal, K. T. et al. Engineering T Cells with Customized Therapeutic Response Programs Using Synthetic Notch Receptors. Cell 167, 419-432 e416, doi:10.1016/j.cell.2016.09.011 (2016).

Roybal, K. T. et al. Precision Tumor Recognition by T Cells With Combinatorial Antigen-Sensing Circuits. Cell 164, 770-779, doi:10.1016/j.cell.2016.01.011 (2016).

Sadelain, M., Brentjens, R. & Riviere, I. The basic principles of chimeric antigen receptor design. Cancer Discov 3, 388-398, doi:10.1158/2159-8290.CD-12-0548 (2013).

Slamon, D. J. et al. Use of chemotherapy plus a monoclonal antibody against HER2 for metastatic breast cancer that overexpresses HER2. N Engl J Med 344, 783-792, doi:10.1056/NEJM200103153441101 (2001).

Sun, X. et al. Development of SNAP-tag fluorogenic probes for wash-free fluorescence imaging. Chembiochem 12, 2217-2226, doi:10.1002/cbic.201100173 (2011).

Tamada, K. et al. Redirecting gene-modified T cells toward various cancer types using tagged antibodies. Clinical cancer research : an official journal of the American Association for Cancer Research 18, 6436-6445, doi:10.1158/1078-0432.CCR-12-1449 (2012).

Toda, S., Blauch, L. R., Tang, S. K. Y., Morsut, L. & Lim, W. A. Programming self-organizing multicellular structures with synthetic cell-cell signaling. Science 361, 156-162, doi:10.1126/science.aat0271 (2018).

Urbanska, K. et al. A universal strategy for adoptive immunotherapy of cancer through use of a novel T-cell antigen receptor. Cancer research 72, 1844-1852, doi:10.1158/0008-5472.CAN-11-3890 (2012).

Van Steeg, T. J., Bergmann, K. R., Dimasi, N., Sachsenmeier, K. F. & Agoram, B. The application of mathematical modelling to the design of bispecific monoclonal antibodies. MAbs 8, 585-592, doi:10.1080/19420862.2016.1141160 (2016).

Veggiani, G. et al. Programmable polyproteams built using twin peptide superglues. Proc Natl Acad Sci U S A 113, 1202-1207, doi:10.1073/pnas.1519214113 (2016).

Wang, J., Yu, Y. & Xia, J. Short peptide tag for covalent protein labeling based on coiled coils. Bioconjug Chem 25, 178-187, doi:10.1021/bc400498p (2014).

Wang, X. & Ha, T. Defining single molecular forces required to activate integrin and notch signaling. Science 340, 991-994, doi:10.1126/science.1231041 (2013).

Wu, H., Hu, Z. & Liu, X. Q. Protein trans-splicing by a split intein encoded in a split DnaE gene of *Synechocystis* sp. PCC6803. Proc Natl Acad Sci U S A 95, 9226-9231, doi:10.1073/pnas.95.16.9226 (1998).

Wu, X., Fan, Z., Masui, H., Rosen, N. & Mendelsohn, J. Apoptosis induced by an anti-epidermal growth factor receptor monoclonal antibody in a human colorectal carcinoma cell line and its delay by insulin. J Clin Invest 95, 1897-1905, doi:10.1172/JCI117871 (1995).

Yang, G. et al. Genetic targeting of chemical indicators in vivo. Nat Methods 12, 137-139, doi:10.1038/nmeth.3207 (2015).

Zola, H. et al. Preparation and characterization of a chimeric CD19 monoclonal antibody. Immunol Cell Biol 69 ( Pt 6), 411-422, doi:10.1038/icb.1991.58 (1991).

International Search Report and Written Opinion dated Dec. 18, 2019, from International Application No. PCT/US2019/054479, 12 pages.

Reddington, S. et al. "Secrets of a covalent interaction for biomaterials and biotechnology: SpyTag and SpyCatcher", Current Opinion in Chemical Biology 2015, 29:94-99.

Erhart D., et al., "Chemical Development of Intracellular Protein Heterodimerizers," Chemistry & Biology, Apr. 2013, vol. 20, No. 4, pp. 549-557, DOI: 10.1016/j.chembiol.2013.03.010.

* cited by examiner a b

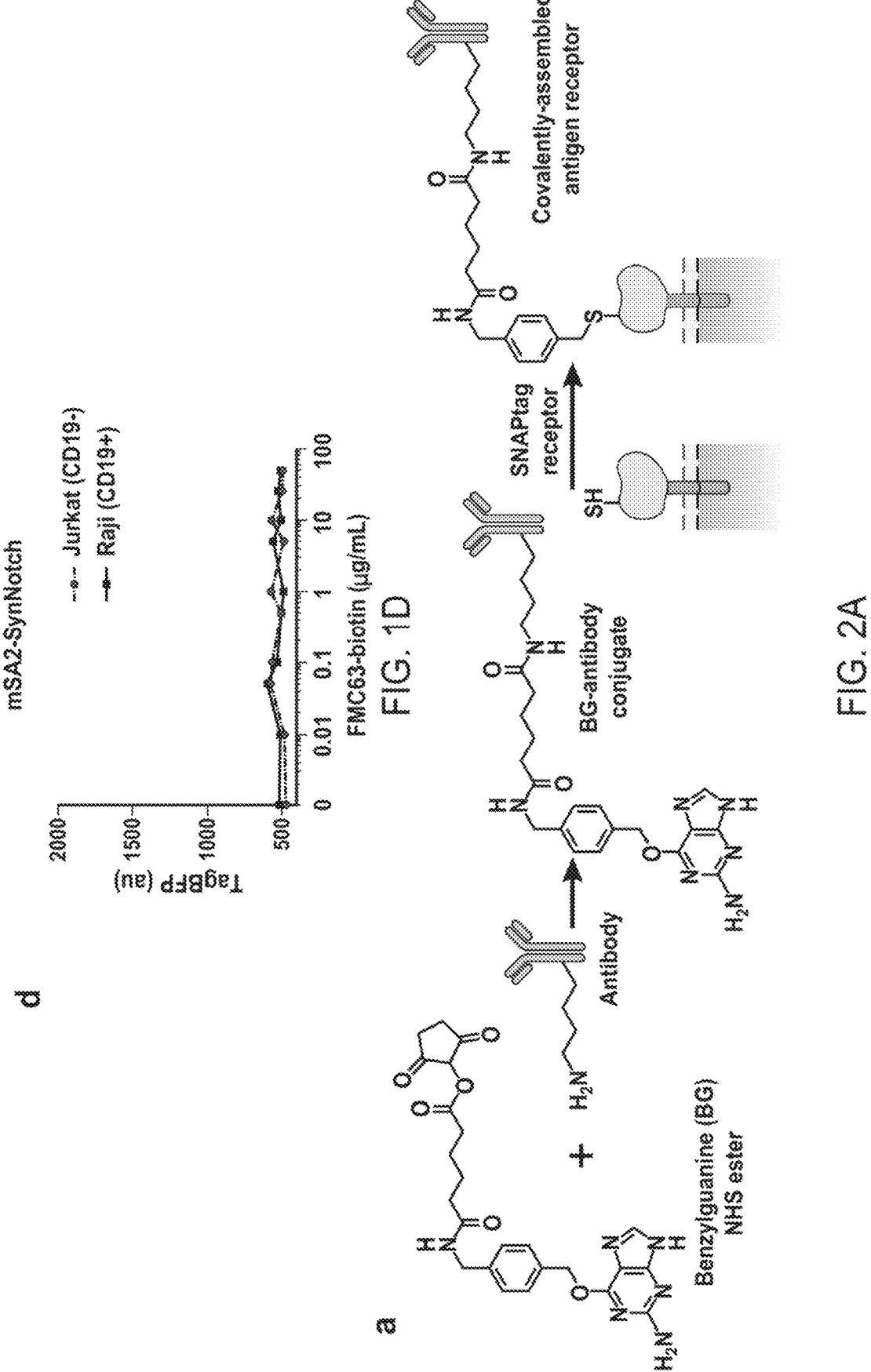

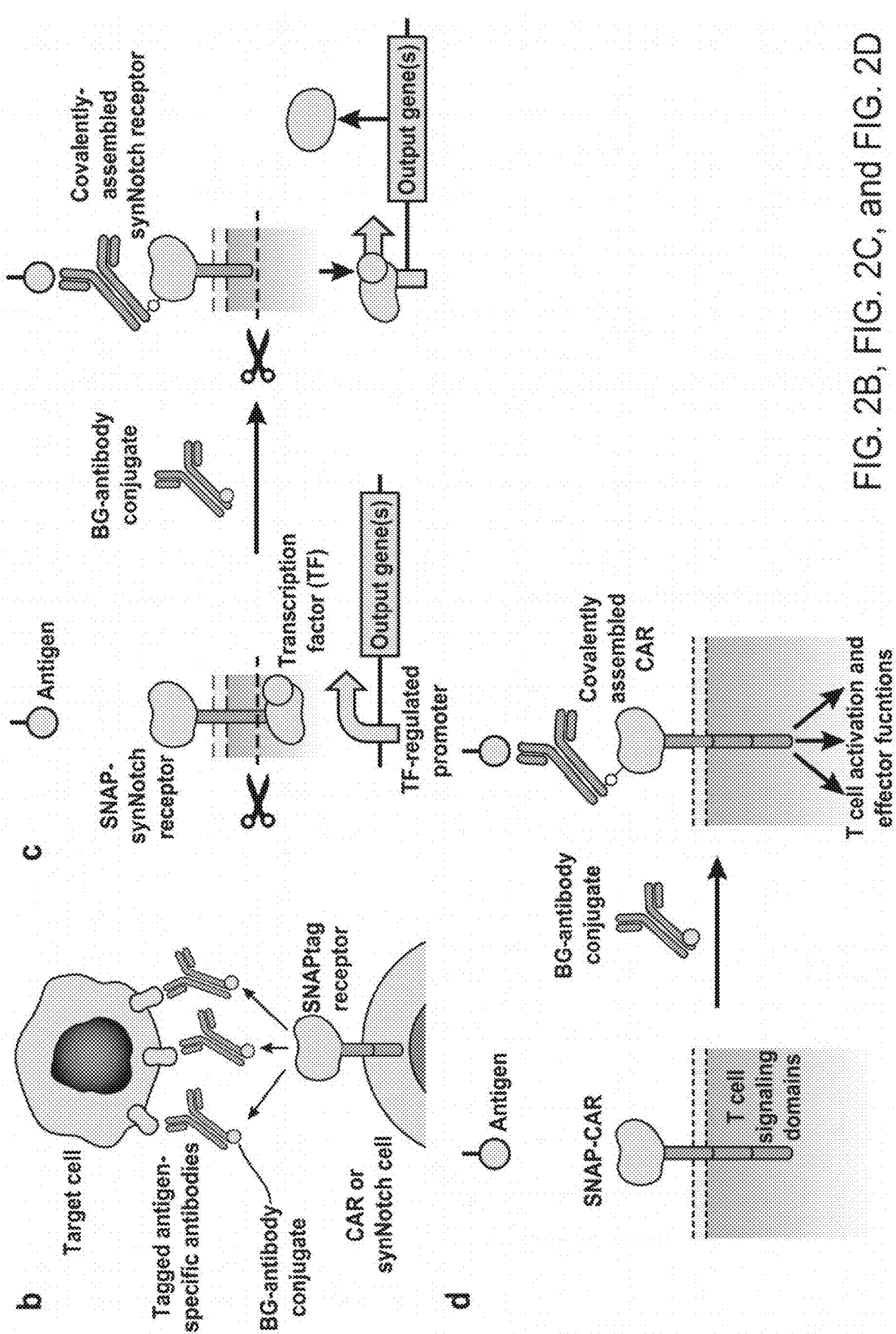
FIG. 2B, FIG. 2C, and FIG. 2D a
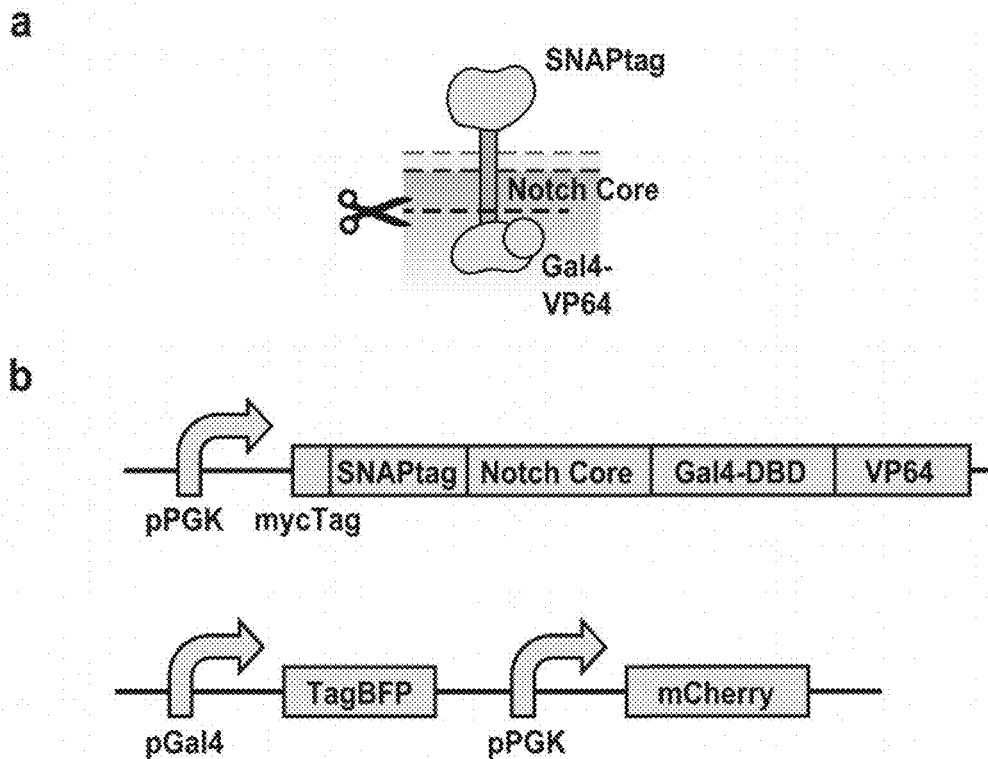
b
c
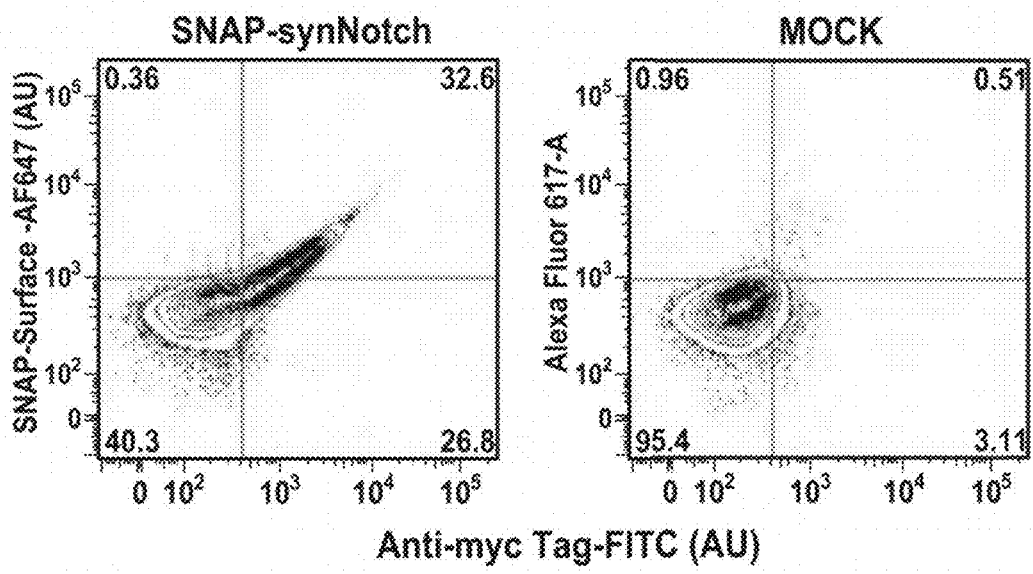
FIG. 3A, FIG. 3B, and FIG. 3C d e
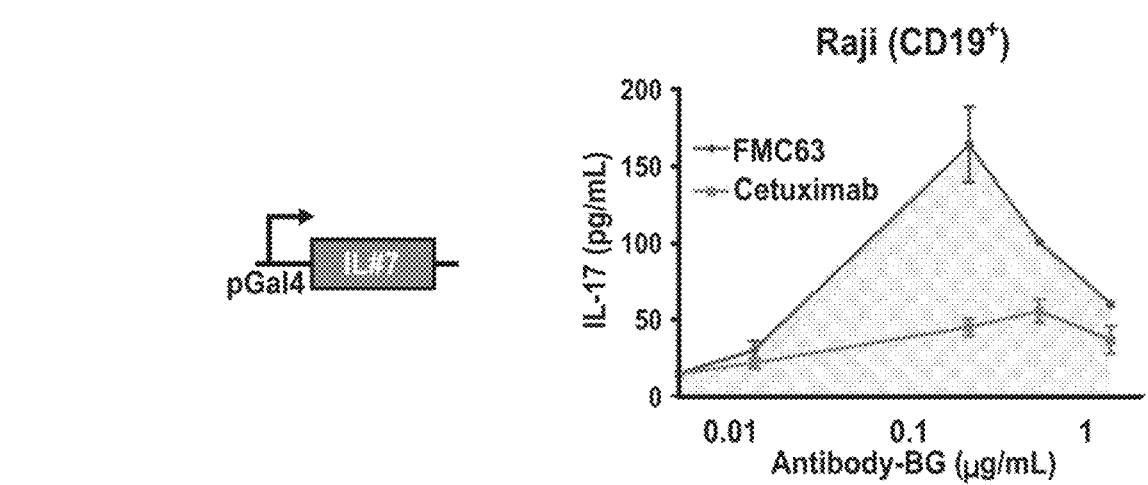
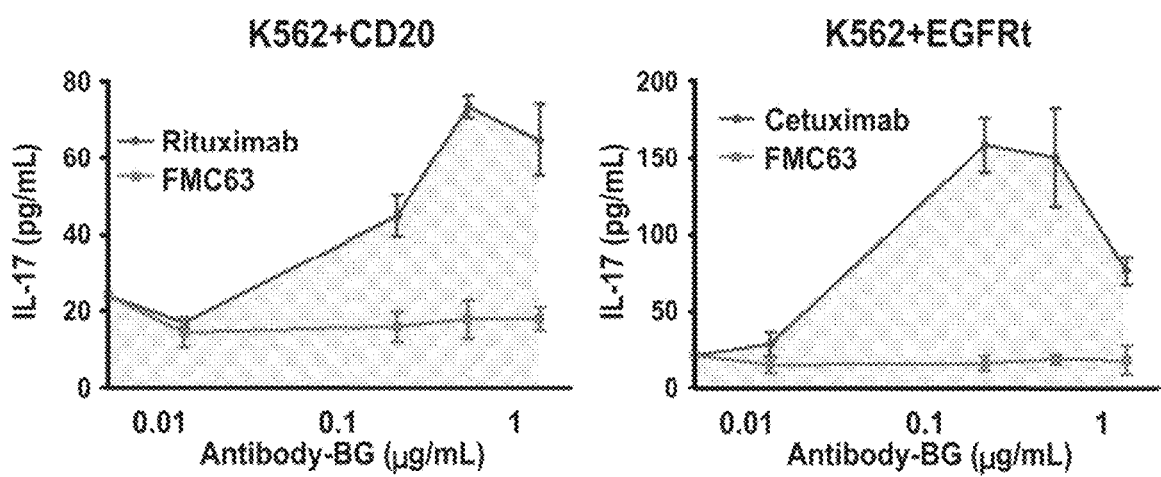
FIG. 3E a
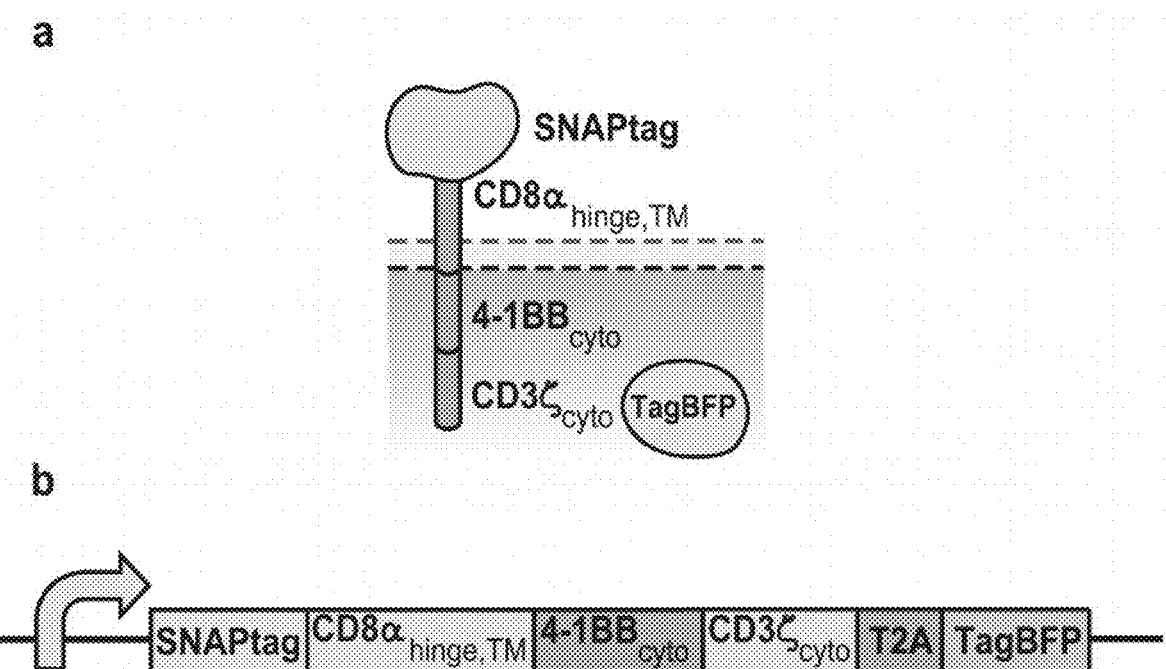
b
c
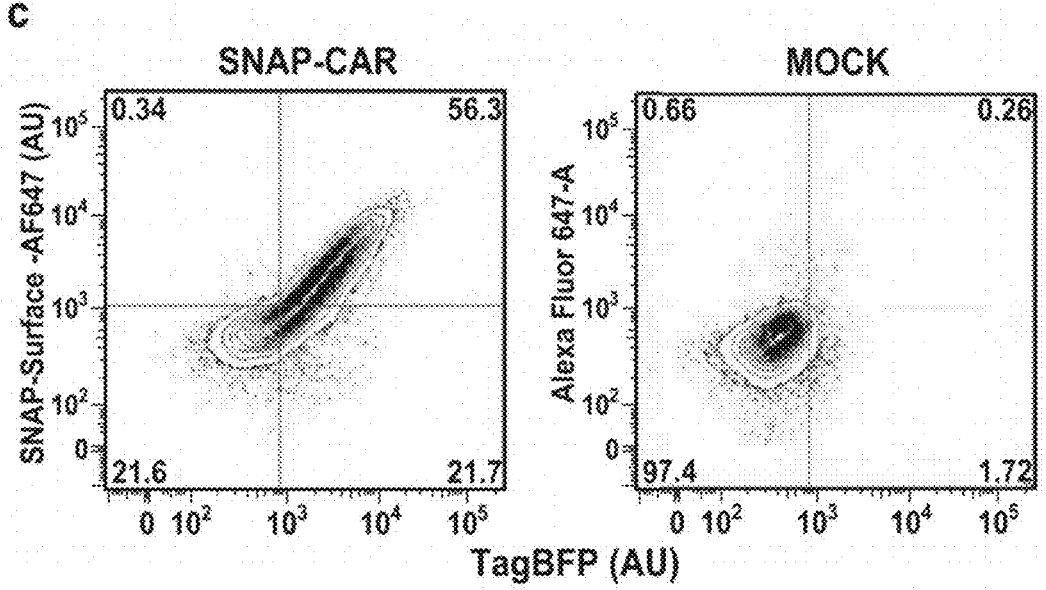
FIG. 5A, FIG. 5B, and FIG. 5C a
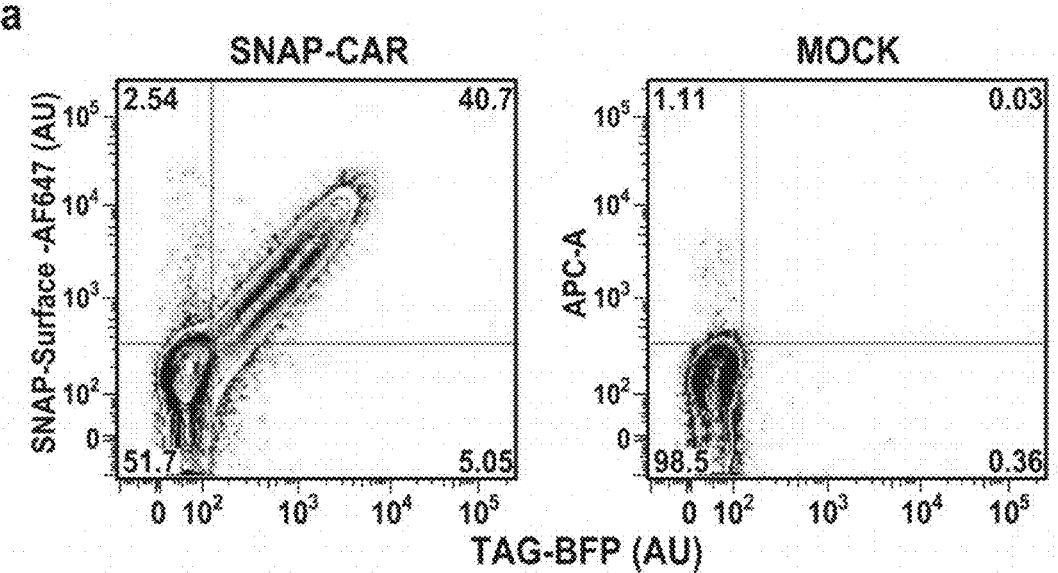
b
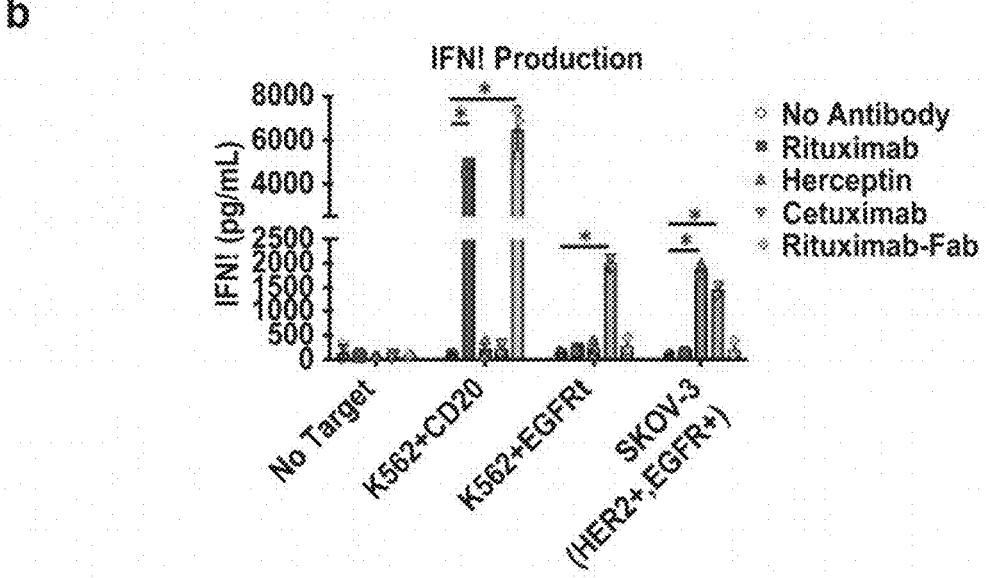
FIG. 6A, and FIG. 6B b

SEQUENCE LISTING

<160> NUMBER OF SEQ ID NOS: 9

<210> SEQ ID NO 1
<211> LENGTH: 2067
<212> TYPE: DNA
<213> ORGANISM: Artificial Sequence
<220> FEATURE:
<223> OTHER INFORMATION: Synthetic construct

<400> SEQUENCE: 1
atggagacag acacactcct gctatgggtg ctgctgctct gggttccagg ttccacaggt      60
atggacaaag attgcgagat gaagagaacc accctggata gccctctcgg caagctcgaa     120
ctttctggtt gtgaacaggg tttgcacagg atcatcttcc tgggaaaggg aacctcagcc     180
gcagatgcgg ttgaagtgcc agctccggct gcagtgcttg gtggaccga gcctcttatg      240 caagcaacgg catggcttaa tgcttatttt caccagcctg aggccattga agagtttcca     300

```
gttcctgcat tgcatcaccc cgttttttcag caggaatcct tcactagaca agtgctttgg      360
aagctcttga aagtggttaa atttgggggaa gtcatctcat acagccacct tgctgccctt      420
gcaggcaatc ctgcggccac ggctgcagtg aaaactgcac ttagcggaaa tccagtcccc      480
atcttgatac cgtgtcacag ggtagtacag ggcgacctgg acgtcggcgg ttacgagggc      540
ggtttggccg ttaaggaatg gttgctggcg catgagggtc accggctggg aaaaccaggt      600
cttggtggag gaagtggagg atctaccact actccggcac cgcgccccc aactcctgca       660 ccgacgatag cttcacaacc gctttcattg cggcccgaag catgtcggcc agccgccgga      720
ggcgctgtgc atacaagagg gctggatttt gcatgtgata tatatatttg ggcgcccctt      780
gctggcactt gcggcgttct tcttcttagc ctcgttatta cgctctactg taagcgaggt      840
aggaaaaaat tgctgtatat ctttaaacag cctttttatga gacccgtgca aacgactcaa      900
gaggaagacg ggtgtagctg tagatttcct gaagaggaag agggggggtg cgaactgcgg      960
gtgaagttca gcagaagcgc cgacgcccct gcctaccagc agggccagaa tcagctgtac      1020
aacgagctga acctgggcag aagggaagag tacgacgtcc tggataagcg gagaggccgg      1080
gaccctgaga tgggcggcaa gcctcggcgg aagaaccccc aggaaggcct gtataacgaa      1140
ctgcagaaag acaagatggc cgaggcctac agcgagatcg gcatgaaggg cgagcggagg      1200
cggggcaagg gccacgacgg cctgtatcag ggcctgtcca ccgccaccaa ggatacctac      1260
gacgccctgc acatgcaggc cctgcccca aggctcgagg gcggcggaga gggcagagga      1320
agtcttctaa catgcggtga cgtggaggag aatcccggcc ctcgcatgag cgagctgatt      1380
aaggagaaca tgcacatgaa gctgtacatg gagggcaccg tggacaacca tcacttcaag      1440
tgcacatccg agggcgaagg caagccctac gagggcaccc agaccatgag aatcaaggtg      1500
gtcgagggcg gccctctccc cttcgccttc gacatcctgg ctactagctt cctctacggc      1560
agcaagacct tcatcaacca cacccagggc atccccgact tcttcaagca gtccttccct      1620
gagggcttca catgggagag agtcaccaca tacgaagacg ggggcgtgct gaccgctacc      1680
caggacacca gcctccagga cggctgcctc atctacaacg tcaagatcag aggggtgaac      1740
ttcacatcca acggccctgt gatgcagaag aaaacactcg ctgggaggc cttcaccgag       1800 acgctgtacc ccgctgacgg cggcctggaa ggcagaaacg acatggccct gaagctcgtg      1860
ggcgggagcc atctgatcgc aaacatcaag accacatata gatccaagaa acccgctaag      1920
aacctcaaga tgcctggcgt ctactatgtg gactacagac tggaaagaat caaggaggcc      1980
aacaacgaaa catacgtcga gcagcacgag gtggcagtgg ccagatactg cgacctccct      2040
agcaaactgg ggcacaagct taattaa                                          2067
```

<210> SEQ ID NO 2
<211> LENGTH: 2271
<212> TYPE: DNA
<213> ORGANISM: Artificial Sequence
<220> FEATURE:
<223> OTHER INFORMATION: Synthetic construct

<400> SEQUENCE: 2

```
atggcgctcc ctgtcaccgc actgcttctt ccgctggcac tgctgctgca cgctgcacgg       60
cctgagcaaa aacttatctc tgaagaggac ctcatggaca aagattgcga gatgaagaga      120
accaccctgg atagccctct cggcaagctc gaactttctg ttgtgaaca gggtttgcac       180 aggatcatct tcctgggaaa gggaacctca gccgcagatg cggttgaagt gccagctccg      240
gctgcagtgc ttggtggacc cgagcctctt atgcaagcaa cggcatggct taatgcttat      300
```

-continued

```
tttcaccagc ctgaggccat tgaagagttt ccagttcctg cattgcatca ccccgttttt      360
cagcaggaat ccttcactag acaagtgctt tggaagctct tgaaagtggt taaatttggg      420
gaagtcatct catacagcca ccttgctgcc cttgcaggca atcctgcggc cacggctgca      480
gtgaaaactg cacttagcgg aaatccagtc cccatcttga taccgtgtca cagggtagta      540
cagggcgacc tggacgtcgg cggttacgag ggcggtttgg ccgttaagga atggttgctg      600
gcgcatgagg gtcaccggct gggaaaacca ggtcttggtg gaggaagtgg aggatctatc      660
ctggactaca gcttcacagg tggcgctggg cgcgacattc ccccaccgca gattgaggag      720
gcctgtgagc tgcctgagtg ccaggtggat gcaggcaata aggtctgcaa cctgcagtgt      780
aataatcacg catgtggctg ggatggtggc gactgctccc tcaacttcaa tgacccctgg      840
aagaactgca cgcagtctct acagtgctgg aagtatttta gcgacggcca ctgtgacagc      900
cagtgcaact cggccggctg cctctttgat ggcttcgact gccagctcac cgagggacag      960 tgcaacccc tgtatgacca gtactgcaag gaccacttca gtgatggcca ctgcgaccag     1020
ggctgtaaca gtgccgaatg tgagtgggat ggcctagact gtgctgagca tgtacccgag     1080
cggctggcag ccggcaccct ggtgctggtg gtgctgcttc cacccgacca gctacggaac     1140
aactccttcc actttctgcg ggagctcagc cacgtgctgc acaccaacgt ggtcttcaag     1200 cgtgatcgc aaggccagca gatgatcttc ccgtactatg ccacgagga agagctgcgc      1260 aagcacccaa tcaagcgctc tacagtgggt tgggccacct cttcactgct tcctggtacc     1320
agtggtgggc gccagcgcag ggagctggac cccatggaca tccgtggctc cattgtctac     1380
ctggagatcg acaaccggca atgtgtgcag tcatcctcgc agtgcttcca gagtgccacc     1440
gatgtggctg ccttcctagg tgctcttgcg tcacttggca gcctcaatat tccttacaag     1500
attgaggccg tgaagagtga gccggtggag cctccgctgc cctcgcagct gcacctcatg     1560
tacgtggcag cggccgcctt cgtgctcctg ttctttgtgg gctgtggggt gctgctgtcc     1620
cgcaagcgcc ggcggatgaa gctgctgagc agcatcgagc aggcctgtga catctgccgg     1680
ctgaagaaac tgaagtgcag caaagaaaag cccaagtgcg ccaagtgcct gaagaacaac     1740
tgggagtgcc ggtacagccc caagaccaag agaagccccc tgaccagagc ccacctgacc     1800
gaggtggaaa gccggctgga aagactggaa cagctgtttc tgctgatctt cccacgcgag     1860
gacctggaca tgatcctgaa gatggacagc ctgcaggaca tcaaggccct gctgaccggc     1920
ctgttcgtgc aggacaacgt gaacaaggac gccgtgaccg acagactggc cagcgtggaa     1980
accgacatgc ccctgaccct gcggcagcac agaatcagcg ccaccagcag cagcgaggaa     2040
agcagcaaca gggccagcg gcagctgaca gtgtctgctg ctgcaggcgg aagcggaggc     2100
tctggcggat ctgatgccct ggacgacttc gacctggata tgctgggcag cgacgccctg     2160
gatgattttg atctggacat gctgggatct gacgctctgg acgatttcga tctcgacatg     2220
ttgggatcag atgcactgga tgactttgac ctggacatgc tcggatcatg a           2271
```

```
<210> SEQ ID NO 3
<211> LENGTH: 564
<212> TYPE: DNA
<213> ORGANISM: Artificial Sequence
<220> FEATURE:
<223> OTHER INFORMATION: Synthetic construct

<400> SEQUENCE: 3
atggacaaag attgcgagat gaagagaacc accctggata gccctctcgg caagctcgaa       60
```

-continued

```
ctttctggtt gtgaacaggg tttgcacagg atcatcttcc tgggaaaggg aacctcagcc     120
gcagatgcgg ttgaagtgcc agctccggct gcagtgcttg gtggacccga gcctcttatg     180
caagcaacgg catggcttaa tgcttatttt caccagcctg aggccattga agagtttcca     240
gttcctgcat tgcatcaccc cgttttttcag caggaatcct tcactagaca agtgctttgg     300
aagctcttga aagtggttaa atttgggggaa gtcatctcat acagccacct tgctgccctt     360
gcaggcaatc ctgcggccac ggctgcagtg aaaactgcac ttagcggaaa tccagtcccc     420
atcttgatac cgtgtcacag ggtagtacag ggcgacctgg acgtcggcgg ttacgagggc     480
ggtttggccg ttaaggaatg gttgctggcg catgagggtc accggctggg aaaaccaggt     540
cttggtggag gaagtggagg atct                                            564
```

```
<210> SEQ ID NO 4
<211> LENGTH: 336
<212> TYPE: DNA
<213> ORGANISM: Artificial Sequence
<220> FEATURE:
<223> OTHER INFORMATION: Synthetic construct

<400> SEQUENCE: 4
cgggtgaagt tcagcagaag cgccgacgcc cctgcctacc agcagggcca gaatcagctg      60
tacaacgagc tgaacctggg cagaagggaa gagtacgacg tcctggataa gcggagaggc     120
cgggaccctg agatgggcgg caagcctcgg cggaagaacc cccaggaagg cctgtataac     180
gaactgcaga aagacaagat ggccgaggcc tacagcgaga tcggcatgaa gggcgagcgg     240
aggcggggca agggccacga cggcctgtat cagggcctgt ccaccgccac caaggatacc     300
tacgacgccc tgcacatgca ggccctgccc ccaagg                               336
```

```
<210> SEQ ID NO 5
<211> LENGTH: 978
<212> TYPE: DNA
<213> ORGANISM: Artificial Sequence
<220> FEATURE:
<223> OTHER INFORMATION: Synthetic construct

<400> SEQUENCE: 5
atcctggact acagcttcac aggtggcgct gggcgcgaca ttcccccacc gcagattgag      60
gaggcctgtg agctgcctga gtgccaggtg gatgcaggca ataaggtctg caacctgcag     120
tgtaataatc acgcatgtgg ctgggatggt ggcgactgct ccctcaactt caatgacccc     180
tggaagaact gcacgcagtc tctacagtgc tggaagtatt ttagcgacgg ccactgtgac     240
agccagtgca actcggccgg ctgcctcttt gatggcttcg actgccagct caccgaggga     300
cagtgcaacc cctgtatgaa ccagtactgc aaggaccact tcagtgatgg ccactgcgac     360
cagggctgta acagtgccga atgtgagtgg gatggcctag actgtgctga gcatgtaccc     420
gagcggctgg cagccggcac cctggtgctg tggtgctgc ttccacccga ccagctacgg      480
aacaactcct tccactttct gcgggagctc agccacgtgc tgcacaccaa cgtggtcttc     540
aagcgtgatg cgcaaggcca gcagatgatc ttcccgtact atggccacga ggaagagctg     600
cgcaagcacc caatcaagcg ctctacagtg ggttgggcca cctcttcact gcttcctggt     660
accagtggtg ggcgccagcg cagggagctg gaccccatgg acatccgtgg ctccattgtc     720
tacctggaga tcgacaaccg gcaatgtgtg cagtcatcct cgcagtgctt ccagagtgcc     780
accgatgtgt ctgccttcct aggtgctctt gcgtcacttg gcagcctcaa tattccttac     840
aagattgagg ccgtgaagag tgagccggtg gagcctccgc tgccctcgca gctgcacctc     900
```

-continued

```
atgtacgtgg cagcggccgc cttcgtgctc ctgttctttg tgggctgtgg ggtgctgctg      960
tcccgcaagc gccggcgg                                                     978

<210> SEQ ID NO 6
<211> LENGTH: 2122
<212> TYPE: DNA
<213> ORGANISM: Artificial Sequence
<220> FEATURE:
<223> OTHER INFORMATION: Synthetic construct

<400> SEQUENCE: 6
ggagcaaggc aggtggacag tggatcatgg agacagacac actcctgcta tgggtgctgc       60
tgctctgggt tccaggttcc acaggtatgg acaaagattg cgagatgaag agaaccaccc      120
tggatagccc tctcggcaag ctcgaacttt ctggttgtga acagggtttg cacaggatca      180
tcttcctggg aaagggaacc tcagccgcag atgcggttga agtgccagct ccggctgcag      240
tgcttggtgg acccgagcct cttatgcaag caacggcatg gcttaatgct tattttcacc      300
agcctgaggc cattgaagag tttccagttc ctgcattgca tcaccccgtt tttcagcagg      360
aatccttcac tagacaagtg ctttggaagc tcttgaaagt ggttaaattt ggggaagtca      420
tctcatacag ccaccttgct gcccttgcag gcaatcctgc ggccacggct gcagtgaaaa      480
ctgcacttag cggaaatcca gtccccatct tgataccgtg tcacagggta gtacagggcg      540
acctggacgt cggcggttac gagggcggtt tggccgttaa ggaatggttg ctggcgcatg      600
agggtcaccg gctgggaaaa ccaggtcttg gtggaggaag tggaggatct accactactc      660
cggcaccgcg ccccccaact cctgcaccga cgatagcttc acaaccgctt tcattgcggc      720
ccgaagcatg tcggccagcc gccggaggcg ctgtgcatac aagagggctg gattttgcat      780
gtgatatata tatttgggcg cccccttgctg gcacttgcgg cgttcttctt cttagcctcg      840
ttattacgct ctactgtaag cgaggtagga aaaaattgct gtatatcttt aaacagcctt      900
ttatgagacc cgtgcaaacg actcaagagg aagacgggtg tagctgtaga tttcctgaag      960
aggaagaggg ggggtgcgaa ctgcgggtga agttcagcag aagcgccgac gcccctgcct     1020
accagcaggg ccagaatcag ctgtacaacg agctgaacct gggcagaagg gaagagtacg     1080
acgtcctgga taagcggaga ggccgggacc ctgagatggg cggcaagcct cggcggaaga     1140
acccccagga aggcctgtat aacgaactgc agaaagacaa gatggccgag gcctacagcg     1200
agatcggcat gaagggcgag cggaggcggg gcaagggcca cgacggcctg tatcagggcc     1260
tgtccaccgc caccaaggat acctacgacg ccctgcacat gcaggccctg cccccaaggc     1320
tcgagggcgg cggagagggc agaggaagtc ttctaacatg cggtgacgtg gaggagaatc     1380
ccggccctcg catgagcgag ctgattaagg agaaacatgca catgaagctg tacatggagg     1440
gcaccgtgga caaccatcac ttcaagtgca catccgaggg cgaaggcaag ccctacgagg     1500
gcacccagac catgagaatc aaggtggtcg agggcggccc tctccccttc gccttcgaca     1560
tcctggctac tagcttcctc tacggcagca agaccttcat caaccacacc cagggcatcc     1620
ccgacttctt caagcagtcc ttccctgagg gcttcacatg ggagagagtc accacatacg     1680
aagacggggg cgtgctgacc gctacccagg acaccagcct ccaggacggc tgcctcatct     1740
acaacgtcaa gatcagaggg gtgaacttca catccaacgg ccctgtgatg cagaagaaaa     1800
cactcggctg ggaggccttc accgagacgc tgtaccccgc tgacggcggc ctggaaggca     1860
gaaacgacat ggccctgaag ctcgtgggcg ggagccatct gatcgcaaac atcaagacca     1920
```

-continued

```
catatagatc caagaaaccc gctaagaacc tcaagatgcc tggcgtctac tatgtggact    1980
acagactgga aagaatcaag gaggccaaca acgaaacata cgtcgagcag cacgaggtgg    2040
cagtggccag atactgcgac ctccctagca aactgggca caagcttaat taagatcctt    2100
gacttgcggc cgcaactccc ac                                            2122
```

<210> SEQ ID NO 7
<211> LENGTH: 624
<212> TYPE: DNA
<213> ORGANISM: Artificial Sequence
<220> FEATURE:
<223> OTHER INFORMATION: Synthetic construct

<400> SEQUENCE: 7

```
gagcaaaaac ttatctctga agaggacctc atggacaaag attgcgagat gaagagaacc      60
accctggata gccctctcgg caagctcgaa ctttctggtt gtgaacaggg tttgcacagg     120
atcatcttcc tgggaaaggg aacctcagcc gcagatgcgg ttgaagtgcc agctccggct     180
gcagtgcttg gtggacccga gcctcttatg caagcaacgg catggcttaa tgcttatttt     240
caccagcctg aggccattga agagtttcca gttcctgcat tgcatcaccc cgttttttcag    300 caggaatcct tcactagaca agtgctttgg aagctcttga aagtggttaa atttgggga     360 gtcatctcat acagccacct tgctgccctt gcaggcaatc ctgcggccac ggctgcagtg     420
aaaactgcac ttagcggaaa tccagtcccc atcttgatac cgtgtcacag ggtagtacag     480
ggcgacctgg acgtcggcgg ttacgagggc ggtttggccg ttaaggaatg gttgctggcg     540
catgagggtc accggctggg aaaaccaggt cttggtggag gaagtggagg atctatcctg     600
gactacagct tcacaggtgg cgct                                            624
```

<210> SEQ ID NO 8
<211> LENGTH: 624
<212> TYPE: DNA
<213> ORGANISM: Artificial Sequence
<220> FEATURE:
<223> OTHER INFORMATION: Synthetic construct

<400> SEQUENCE: 8

```
gagcaaaaac ttatctctga agaggacctc atggacaaag attgcgagat gaagagaacc      60
accctggata gccctctcgg caagctcgaa ctttctggtt gtgaacaggg tttgcacagg     120
atcatcttcc tgggaaaggg aacctcagcc gcagatgcgg ttgaagtgcc agctccggct     180
gcagtgcttg gtggacccga gcctcttatg caagcaacgg catggcttaa tgcttatttt     240
caccagcctg aggccattga agagtttcca gttcctgcat tgcatcaccc cgttttttcag    300 caggaatcct tcactagaca agtgctttgg aagctcttga aagtggttaa atttgggga     360 gtcatctcat acagccacct tgctgccctt gcaggcaatc ctgcggccac ggctgcagtg     420
aaaactgcac ttagcggaaa tccagtcccc atcttgatac cgtgtcacag ggtagtacag     480
ggcgacctgg acgtcggcgg ttacgagggc ggtttggccg ttaaggaatg gttgctggcg     540
catgagggtc accggctggg aaaaccaggt cttggtggag gaagtggagg atctatcctg     600
gactacagct tcacaggtgg cgct                                            624
```

<210> SEQ ID NO 9
<211> LENGTH: 591
<212> TYPE: DNA
<213> ORGANISM: Artificial Sequence
<220> FEATURE:
<223> OTHER INFORMATION: Synthetic construct

<400> SEQUENCE: 9

```
ccgatccagc ctctcgacat tcgttggatc atgttccacg taagtttcag atatatcttt      60
ggacttccgc cgctcatatt ggtattgttg ccagtggcat ctagtgactg tgacatagaa     120
ggaaaggatg gtaaacagta tgaaagcgta cttatggtat ccattgacca gcttctcgat     180
agtatgaaag agattggtag taattgcctc aataacgagt tcaatttctt taaacgacac     240
atttgtgatg cgaataaaga gggaatgttt ctgtttcgcg ccgcgaggaa gcttaggcag     300
ttccttaaaa tgaactcaac tggggatttc gacctccatc tgctgaaggt gagtgaaggt     360
actactattc tcctgaattg cacgggacag gtaaaggggc gaaaacctgc ggccttgggt     420
gaggcacaac caaccaaaag cctcgaagaa aacaagtccc tcaaagaaca gaagaagctc     480
aacgatctgt gctttctgaa aagactcttg caggagatca aaacttgttg gaataagatt     540
ttgatgggca ctaaggagca ttaagatcct tgacttgcgg ccgcaactcc c            591
```

COVALENT ADAPTOR SYNNOTCH AND CHIMERIC ANTIGEN RECEPTORS (CARS) FOR PROGRAMMABLE ANTIGEN-TARGETING

This application is a national stage application filed under 35 U.S.C. § 371 of PCT/US2019/054479, filed on Oct. 3, 2019, which claims the benefit of U.S. Provisional Application No. 62/740,801, filed on Oct. 3, 2018, applications which are incorporated herein by reference in its entirety.

This invention was made with government support under R35 CA210039 and R21 AI130815 awarded by the National Institutes of Health and under W911NF-17-1-0135 awarded by the Defense Advanced Research Projects Agency. The government has certain rights in the invention.

I. BACKGROUND

The ability to make a universal yet versatile system to generate T cells that are capable of recognizing various types of cancers has important clinical implications for the use of T cell-based therapies. One current strategy incorporates the use of genetic engineering to express a chimeric antigen receptor (CAR) on T cells. The extracellular domain of a typical CAR consists of the $V_H$ and $V_L$ domains—single-chain fragment variable (scFv)—from the antigen binding sites of a monoclonal antibody. The scFv is linked to a flexible transmembrane domain followed by a tyrosine-based activation motif such as that from CD35. Second and third generation CARs include additional activation domains from co-stimulatory molecules such as CD28 and CD137 (41BB) which serve to enhance T cell survival and proliferation. CAR T cells offer the opportunity to seek out and destroy cancer cells by recognizing tumor-associated antigens (TAA) expressed on their surface. As such, the recognition of a tumor cells occurs via an MHC-independent mechanism. Various preclinical and early-phase clinical trials highlight the efficacy of CAR T cells to treat cancer patients with solid tumors and hematopoietic malignancies.

Despite of the promise that CAR T cells might have in treating cancer patients there are several limitations to the generalized clinical application of CAR T cells. First, since no single tumor antigen is universally expressed by all cancer types, scFv in CAR needs to be constructed for each tumor antigen to be targeted. Second, the financial cost and labor-intensive tasks associated with identifying and engineering scFvs against a variety of tumor antigens poses a major challenge. Third, tumor antigens targeted by CAR could be down-regulated or mutated in response to treatment resulting in tumor evasion. Since current CAR T cells recognize only one target antigen, such changes in tumors negate the therapeutic effects. Therefore, the generation of CAR T cells capable of recognizing multiple tumor antigens is highly desired. Finally, CAR T cells react with target antigen weakly expressed on non-tumor cells, potentially causing severe adverse effects. To avoid such "on-target off-tumor" reaction, use of scFvs with higher specificity to tumor antigen is required. And although ongoing studies are focused on generating methods to shut off CAR T cells in vivo this system has yet to be developed and might pose additional inherent challenges.

Modifications to existing CAR T cell systems that address and overcome the hurdles currently preventing development of the systems into effective means of in vivo treatment are therefore needed.

II. SUMMARY

Disclosed are methods and compositions related to universal chimeric antigen receptor (CAR) and universal Synthetic Notch Receptor (synNotch) that fully addresses the deficiencies of current CAR T cell and synNotch systems. The universal CAR and synNotch are capable of recognizing various cancers types and that have broad and valuable clinical implications for the use of T cell-based therapies. As disclosed herein, a versatile universal CAR and universal synNotch receptors which grant T cells specificity to recognize and bind target proteins has been developed.

In one aspect, disclosed herein are universal chimeric antigen receptor (CAR), wherein the CAR comprises an adaptor molecule, a CD8& hinge domain, and a CD35 signaling domain.

Also disclosed herein are universal CAR of any preceding aspect, further comprising one or more co-stimulation domains (such as, for example, signaling domains for CD27, CD28, ICOS, 4-1BB, or OX40).

In one aspect, disclosed herein are universal synthetic Notch (synNotch) receptors, comprising an adaptor molecule, a notch core comprising one or more cleavage sites, and one or more transcription factors.

Also disclosed herein are universal synNotch, and/or universal CAR of any preceding aspect, wherein the adaptor molecule comprises a protein SNAP-Tag®, CLIP-Tag™, Halotag®, SpyTag, SnoopTag, or Isopep-tag. In some aspect, the universal CAR and/or universal synNotch of any preceding aspect can comprise an adaptor molecule, wherein the adaptor molecule comprises NHS-ester conjugation, bis-sulfone conjugation, glycan conjugating chemistry, recombinant antibodies with BG incorporation through short peptide tags, sortase mediated ligation, chemical ligation, split inteins, and/or unnatural amino acids. As used herein, unnatural amino acids refers to any nonstandard amino acid comprising chemistry deferent than 20 canonical proteinogenic amino acids found in eukaryotes including, but not limited to, beta amino acids, D-amino acids, dehydroamino acids, as well, as amino acids comprising alkyne, alkene, azide, tetrazene, keto, and other functional groups. Thus, in some aspects, it is understood and herein contemplated that the bioconjugation as used herein can occur via alkene-tetrazine reaction, alkyne-azide reactions, phosphine-azide reactions, alkene-tetrazine reactions, and/or keto-hydrazide reactions.

In one aspect, disclosed herein are universal synNotch, and/or universal CAR of any preceding aspect, further comprising an antigen recognition element; wherein the antigen recognition element is covalently linked to the adaptor molecule, and wherein the antigen recognition element comprises a modification that allows the formation of a covalent bond to the adaptor molecule. For example, the modification of the antigen recognition element can be the inclusion of a Spy Catcher Protein (for forming a covalent bond when the adaptor molecule comprises a SpyTag peptide), Snoop Catcher protein (for forming a covalent bond when the adaptor molecule comprises a SnoopTag peptide), chloroalkane linker for forming a covalent bond when the adaptor molecule comprises a Halotag®), $O^6$-benzylguanine (for forming a covalent bond when the adaptor molecule comprises a SNAP-Tag®), $O^2$-benzylcytosine (for forming a covalent bond when the adaptor molecule comprises a CLIP-Tag™).

Also disclosed herein are universal synNotch, and/or universal CAR of any preceding aspect, wherein the antigen recognition element comprises an antibody (such as, for example, rituximab, FMC63, Herceptin, Cetuximab, nimotuzumab, panitumumab, omalizumab, tositumomab, trastuzumab, gemtuzumab, alemtuzumab, bevacuzimab) or antigen recognizing fragment thereof. In some aspect, the antigen recognition element can comprise a protein binding domain (such as, for example, Nanobodies and single domain antibodies (e.g., monobodies), lectins, DNA aptamers, RNA aptamers, any small molecule ligands for cell surface receptors (e.g., folic acid which is bound by the folic acid receptor), peptide/protein ligands for natural protein receptors (such as, for example, NKG2D and/or cytokines which can be bound to their natural receptors).

In one aspect, disclosed herein are engineered cells (such as, for example, an immune cell (e.g., T cell, a B cell, memory T cell, memory B cell, NK T cell, a monocyte, a natural killer cell, a dendritic cell, a macrophage, a regulatory T cell, a helper T cell, or a cytotoxic T cell), a neuron, an epithelial cell, and endothelial cell, or a stem cell) comprising the universal CAR and/or universal synNotch). In one aspect, disclosed herein are engineered T cells comprising the universal CAR (universal CAR T cells) and/or universal synNotch (engineered universal synNotch cell) of any preceding aspect.

Also disclosed herein are engineered cells comprising a universal synthetic Notch (synNotch) receptor of any preceding aspect, further comprising a vector comprising with a transcriptional response element operatively linked to a promoter driving expression of one or more response genes (such as, for example, T cell effector molecules IL-4, IL-10, FASL, IFN-γ, TNF-α, granzyme A. granzyme B, granulysin, and/or perforin); wherein the one or more of the transcription factors on the synNotch receptor are specific for the transcriptional response element.

Also disclosed herein are engineered T cells comprising a universal synthetic Notch (synNotch) receptor of any preceding aspect, wherein one or more transcription factors of the universal synNotch receptor activate expression of one or more native response genes (such as, for example, IL-4, IL-10, FASL, IFN-γ, TNF-α, granzyme A. granzyme B, granulysin, and/or perforin).

In one aspect, disclosed herein are engineered T cell comprising the universal CAR and the universal synNotch receptors of any preceding aspect, wherein the CAR and synNotch receptor comprise different adaptor molecules.

In one aspect, disclosed herein are methods of treating a caner in a subject comprising administering to the subject the CAR T cell and/or the engineered T cell of any preceding aspect to the subject.

III. BRIEF DESCRIPTION OF THE DRAWINGS

The accompanying drawings, which are incorporated in and constitute a part of this specification, illustrate several embodiments and together with the description illustrate the disclosed compositions and methods.

Figure 1B:
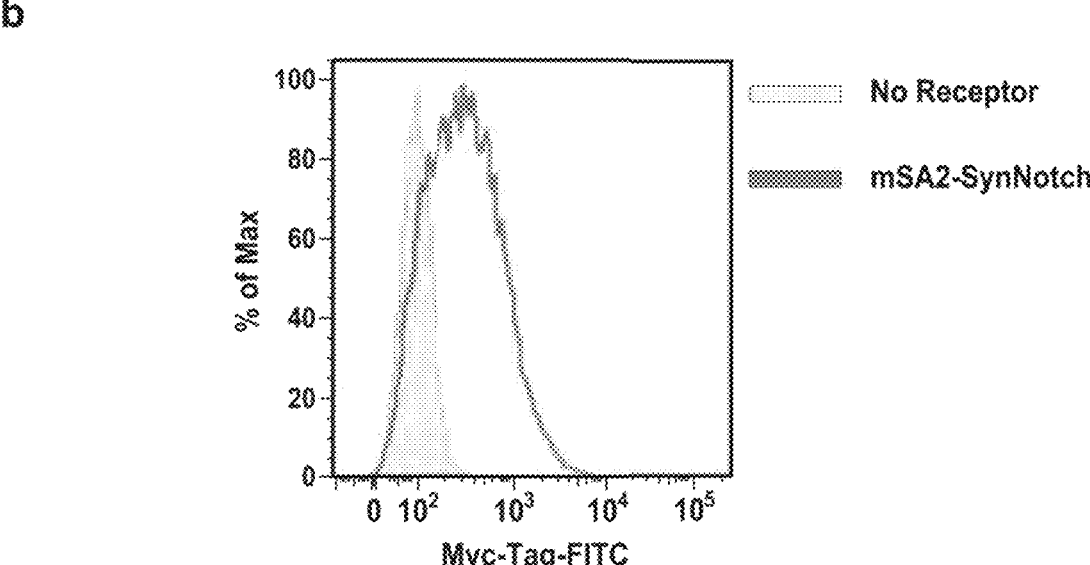
Figure 1C:
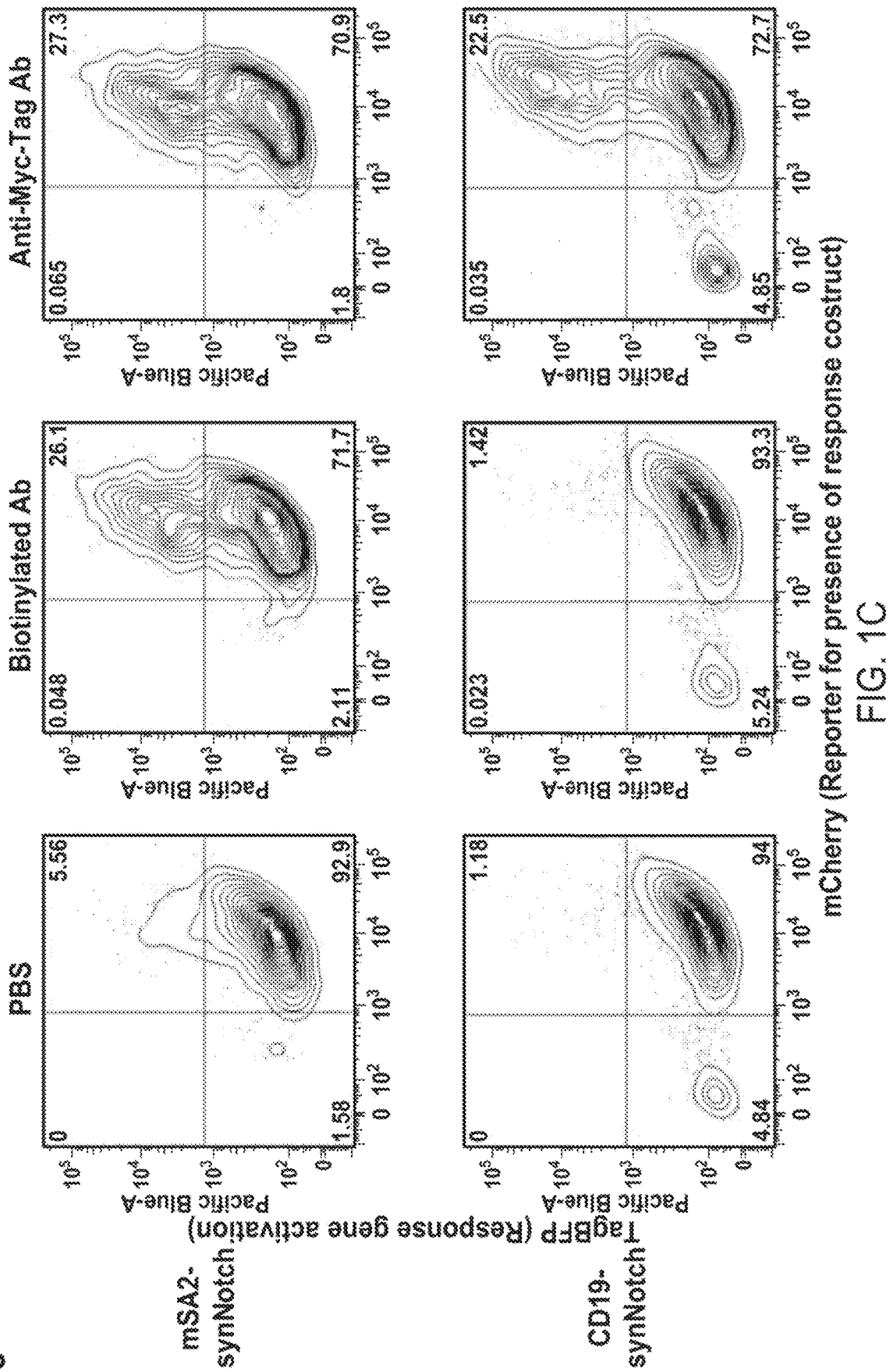

FIGS. 1A, 1B, 1C and 1D show that mSA2 biotin-binding synNotch receptor is activated by plate-bound biotinylated antibody but not antibody bound to the surface of target cells. FIG. 1A shows the design of SNAP-synNotch receptor expression and response lentiviral vectors. FIG. 1B shows flow cytometry analysis of the surface expression of the mSA2-synNotch receptor on transduced vs. MOCK (un) transduced Jurkat cells assessed by staining with the anti-Myc-Tag antibody. FIG. 1C shows flow cytometry analysis of the activation of mSA2-synNotch cells incubated on plates coated with PBS, biotinylated antibody, or anti-Myc-Tag antibody, for 48 hours for TagBFP output gene expression of response construct positive (mCherry+) cells. FIG. 1D shows low cytometry analysis of the activation of mSA2-synNotch cells co-incubated with the indicated target cell lines and antibody concentrations for 48 hours for TagBFP output gene expression reported as mean fluorescence intensity (MFI).

FIGS. 2A, 2B, 2C, and 2D show a schematic of the function of universal adaptor SNAP-CAR and synNotch Receptors. FIG. 2A shows that benzyl guanine tag (BG) is chemically-conjugated to an antibody using the benzylguanine NHS ester. The BG-antibody conjugate is then further conjugated to the extracellular SNAPtag enzyme domain of a SNAPtag receptor via the SNAPtag self-labeling enzymatic reaction. FIG. 2B shows that SNAPtag receptors enable the targeting of multiple different antigens using the same receptor by combining SNAP receptor cells with different BG-conjugated antibodies. FIG. 2C shows that the SNAP-synNotch receptor is re-targeted by a BG-conjugated antibody and upon antigen recognition leads to transcriptional regulation of a target gene or genes. FIG. 2D shows that the SNAP-CAR is re-targeted by a BG-conjugated antibody and upon antigen recognition activates T cell signaling and effector functions.

Figure 3D:
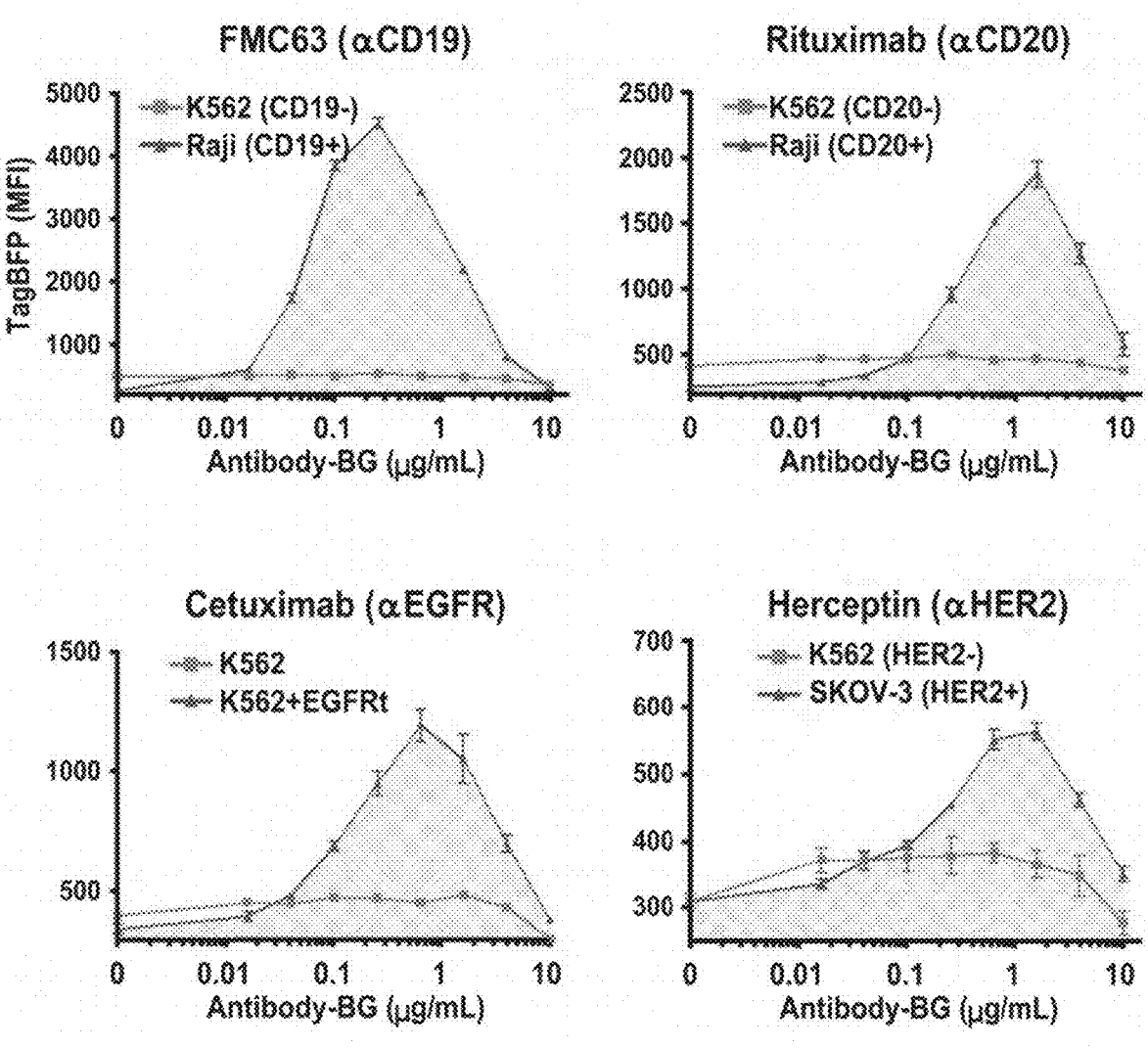

FIGS. 3A, 3B, 3C, 3D, and 3E show that SNAP-synNotch receptors can be targeted to desired antigens of interest by benzylguanine-conjugated binding proteins. FIG. 3A shows a diagram of the SNAP-synNotch receptor. FIG. 3B shows the design of SNAP-synNotch receptor expression and response lentiviral vectors. FIG. 3C shows flow cytometry analysis of the surface expression and enzymatic functionality of SNAP-synNotch receptor on transduced vs. MOCK (un) transduced Jurkat cells assessed by staining with the SNAP-Surface-AF647 dye and anti-Myc-Tag antibody. FIG. 3D shows flow cytometry analysis of the activation of SNAP-synNotch cells co-incubated with the indicated target cell lines and antibody concentrations for 48 hours for TagBFP output gene expression reported as mean fluorescence intensity (MFI) and 3E, by ELISA for the production of the IL-7 therapeutic transgene. For 3D and 3E, n=3 biologically-independent experiments±s.e.m.

Figure 4:
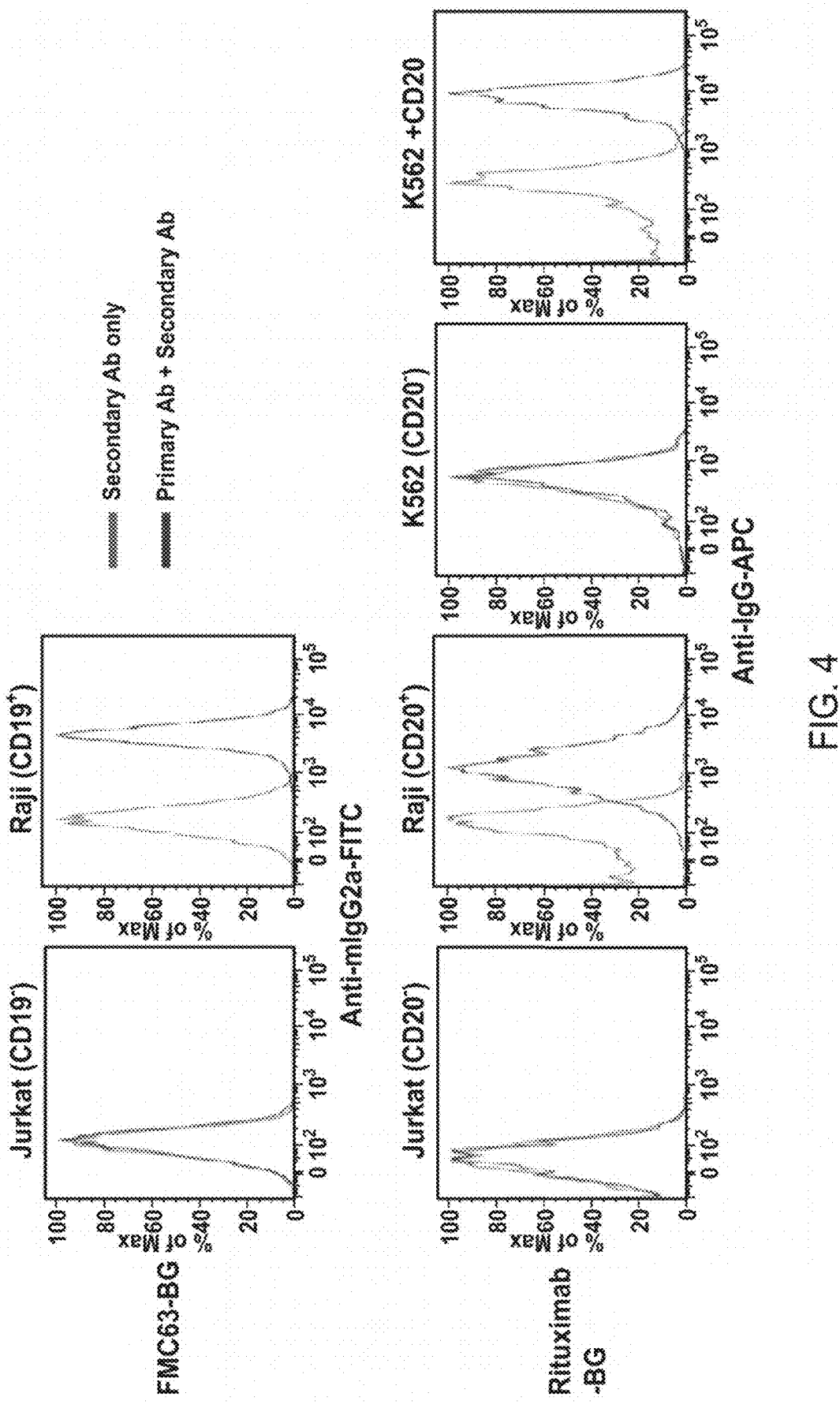
Figure 4:
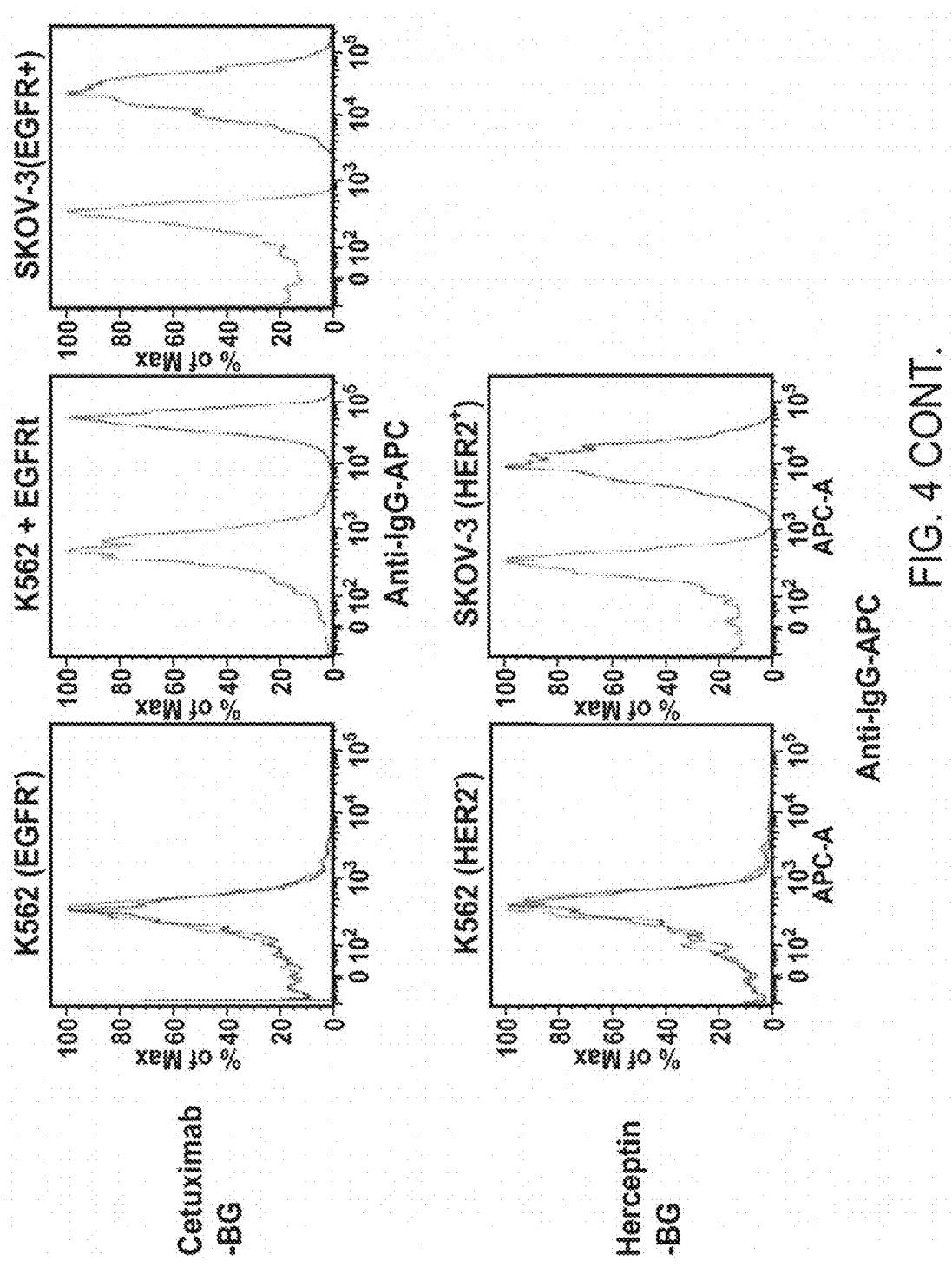

FIG. 4 shows staining of target cell lines by benzyl guanine (BG)-conjugated antibodies. Target cell lines were stained with 1.6 ug/mL of the indicated BG-conjugated antibodies (1 ug/mL was used for FMC63-BG) followed by staining with an anti-IgG secondary antibody (anti-mIgG2a-FITC for FMC63-BG and anti-IgG (Fab2)-APC for all other antibodies). Cells were then washed and analyzed by flow cytometry.

Figure 5D:
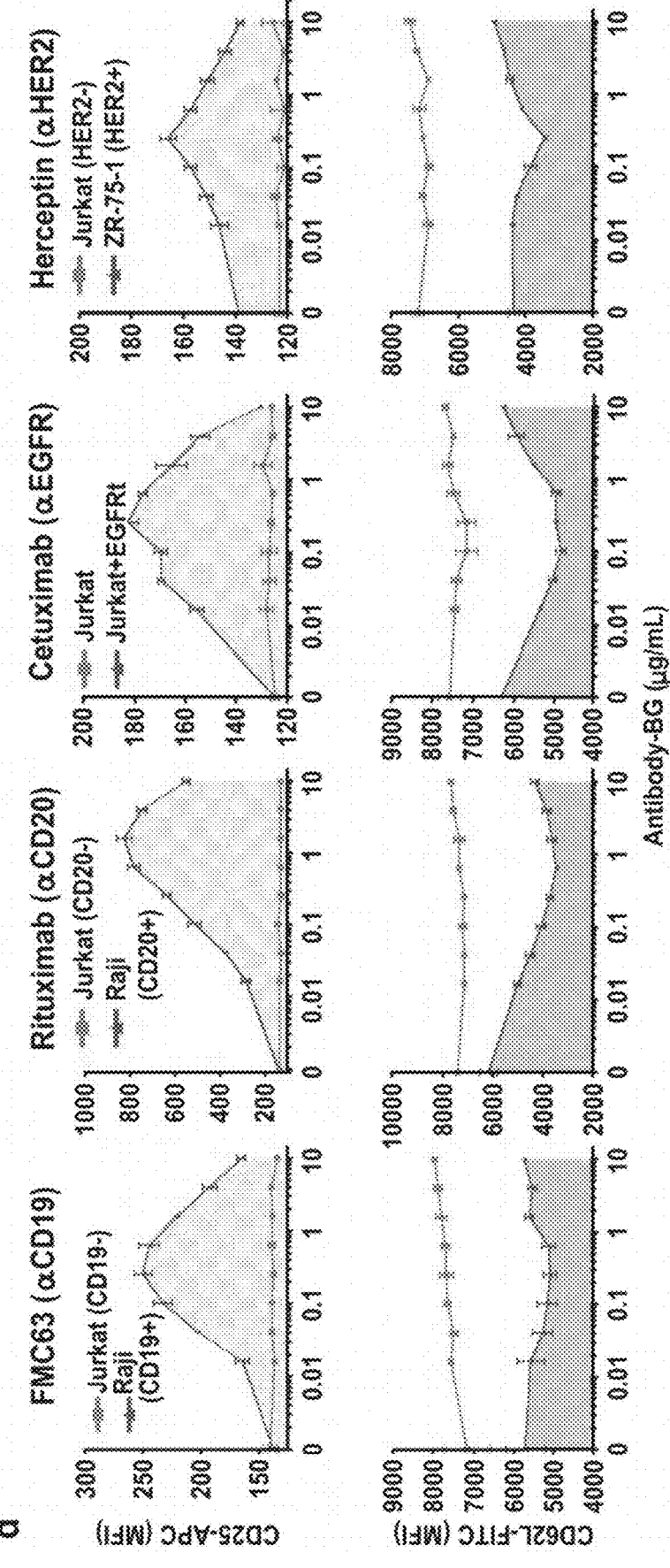

FIGS. 5A, 5B, 5C, and 5D show that the SNAP-CAR can be targeted to desired antigens of interest by benzylguanine-conjugated binding proteins. FIG. 5A shows a diagram of the SNAP-CAR. FIG. 5B shows the design of SNAP-CAR lentiviral expression construct. FIG. 5C shows flow cytometry analysis of the expression and enzymatic functionality of the SNAP-CAR receptor on transduced vs. MOCK (un) transduced Jurkat cells assessed by staining with SNAP-Surface-AF647 dye and recording TagBFP expression. FIG. 5D shows flow cytometry analysis of the activation of CD25 and CD62L T cell activation markers on Jurkat SNAP-CAR effector cells co-incubated with the indicated target cell lines and antibody concentrations for 24 hours reported as mean fluorescence intensity (MFI). CD25 increases while CD62L decreases with activation, n=3 biologically-independent experiments±s.e.m.

Figures 6C, 6D:
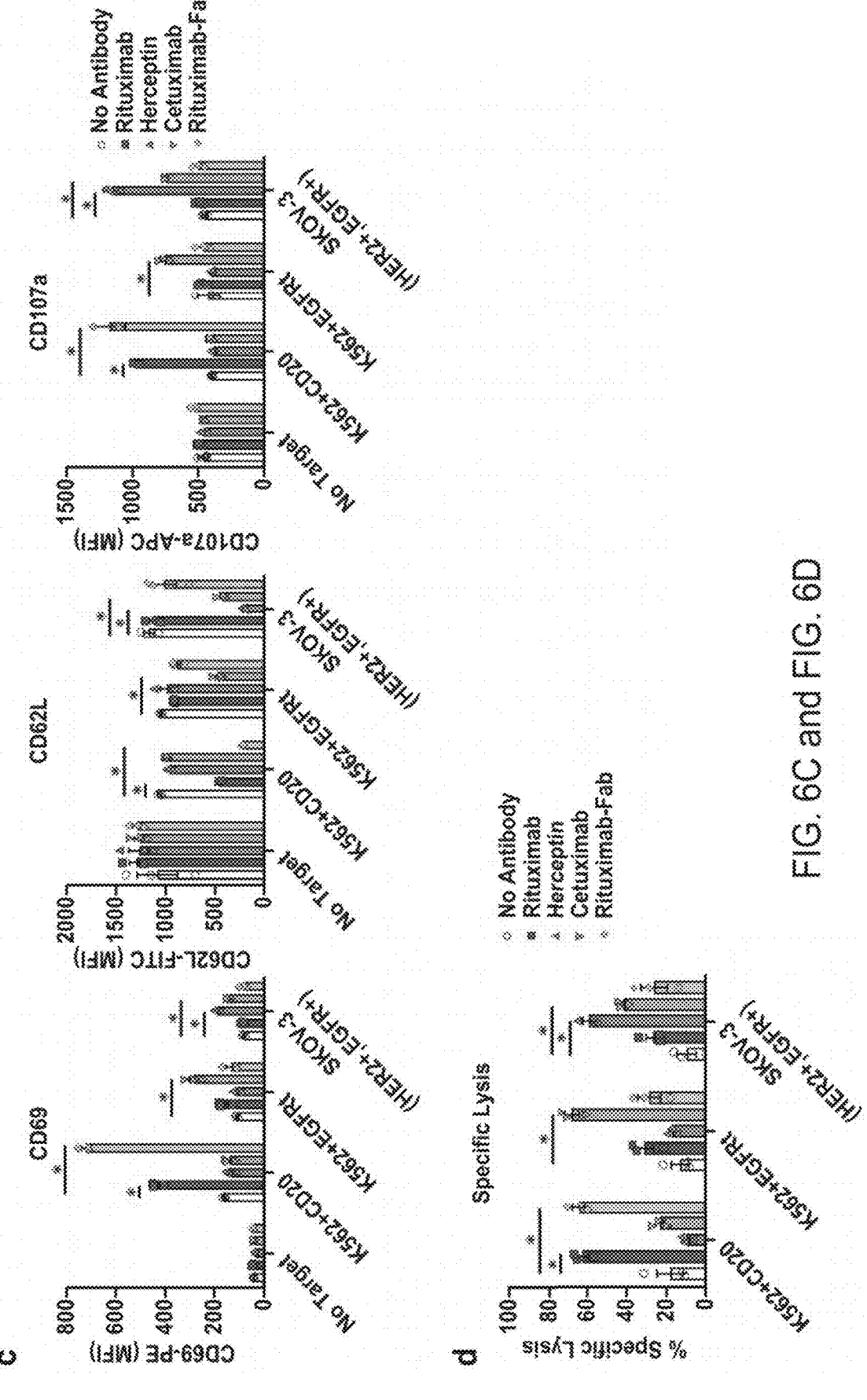

FIGS. 6A, 6B, 6C, and 6D show that the SNAP-CAR is effective on primary human T cells. FIG. 6A shows flow cytometry analysis of the expression and enzymatic functionality of the SNAP-CAR on transduced vs. MOCK (un) transduced primary human T cells by staining with SNAP-Surface-AF647 dye and recording TagBFP expression. FIG.

6B shows ELISA for IFNγ production from primary human SNAP-CAR T effector cells co-incubated with the indicated target cell lines and 1 μg/mL of the indicated antibody for 24 hours and 6C, flow cytometry analysis of CD69, CD62L, and CD105a T cell activation markers from the co-incubations in b, reported as MFI. FIG. 6D shows specific lysis of target cell lines by co-incubated primary human SNAP-CAR T cells and 1 μg/mL of the indicated BG-conjugated antibodies. For 6B, 6C, and 6D, multiple ANOVA comparisons were performed. As the data did not have homogeneity of variance (Levene's test), Tukey's HSD was used for post hoc analysis between antibody conditions. "*" denotes a significance of p<0.001, n=3 biologically-independent experiments±s.e.m.

Figures 7A, 7B:
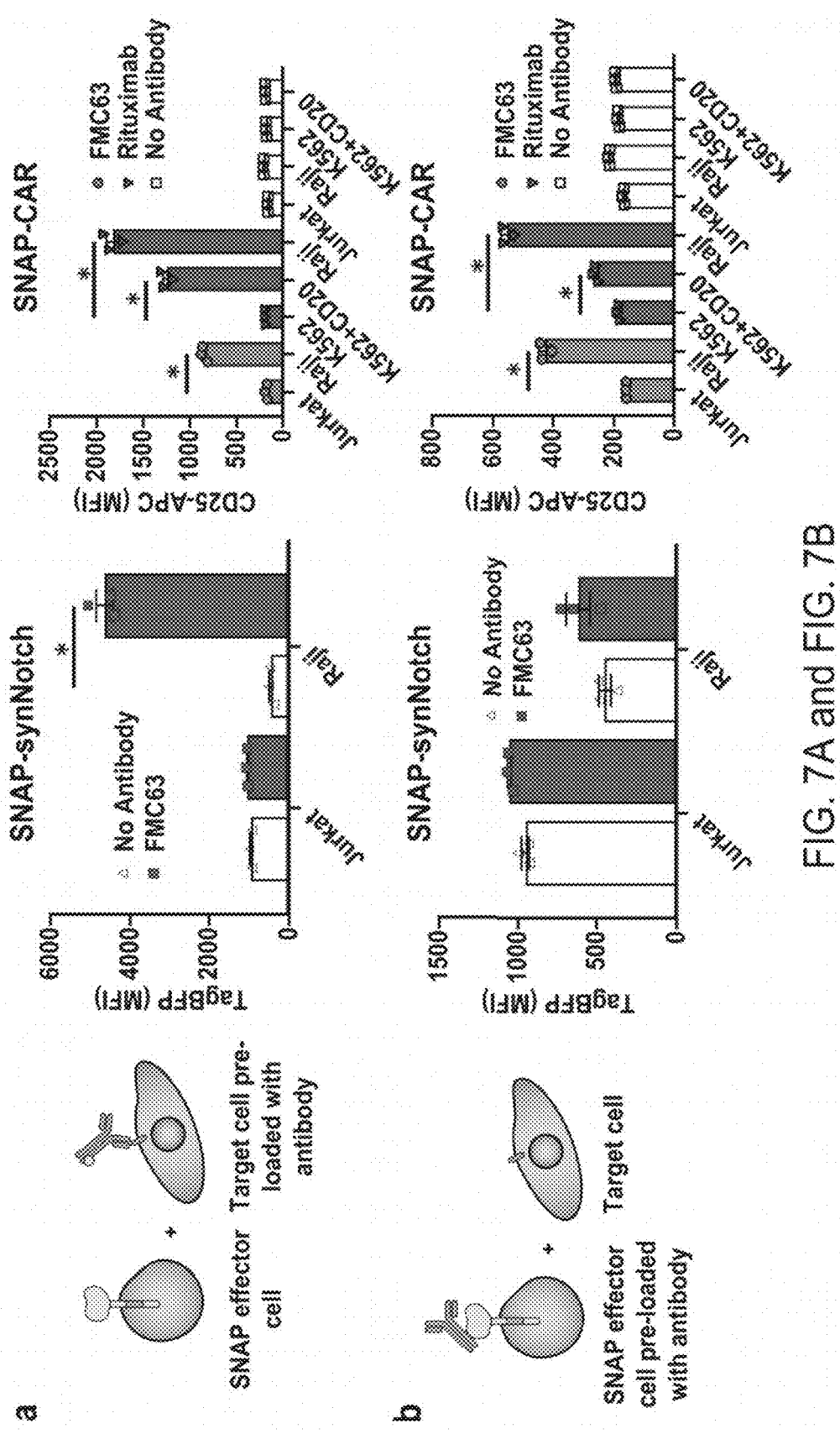

FIGS. 7A and 7B show the characterizing the activity of SNAP-synNotch and CAR receptors when pre-assembled or with pre-labeled target cells. FIG. 7A shows flow cytometry analysis of SNAP receptor activation for SNAP-synNotch and SNAP-CAR cells co-incubated, for 48 and 24 hours, respectively, with target cells that were pre-labeled with the indicated antibodies. FIG. 7B shows flow cytometry analysis of SNAP receptor activation for SNAP-synNotch and SNAP-CAR cells that were pre-labeled with the indicated antibodies and co-incubated with target cells for 48 and 24 hours, respectively. MFI of TagBFP output gene expression and CD25 marker expression were evaluated by flow cytometry for SNAP-SynnNotch and SNAP-CAR cells, respectively. For 7A and 7B, multiple ANOVA comparisons were performed. As the data did not have homogeneity of variance (Levene's test), Tukey's HSD was used for post hoc analysis between antibody conditions. "*" denotes a significance of p<. O$^{001}$, n=3 biologically-independent experiments±s.e.m.

Figure 8A:
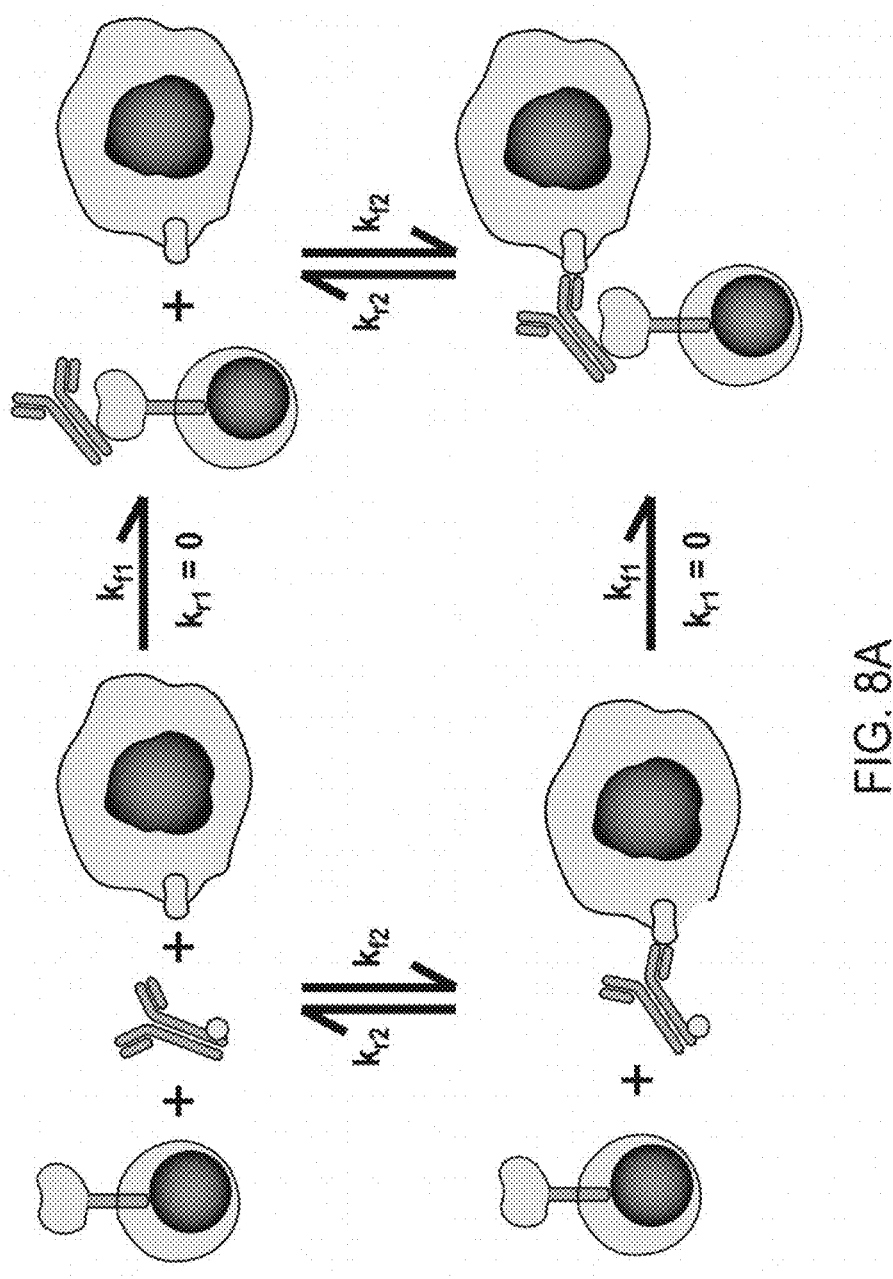
Figure 8B:
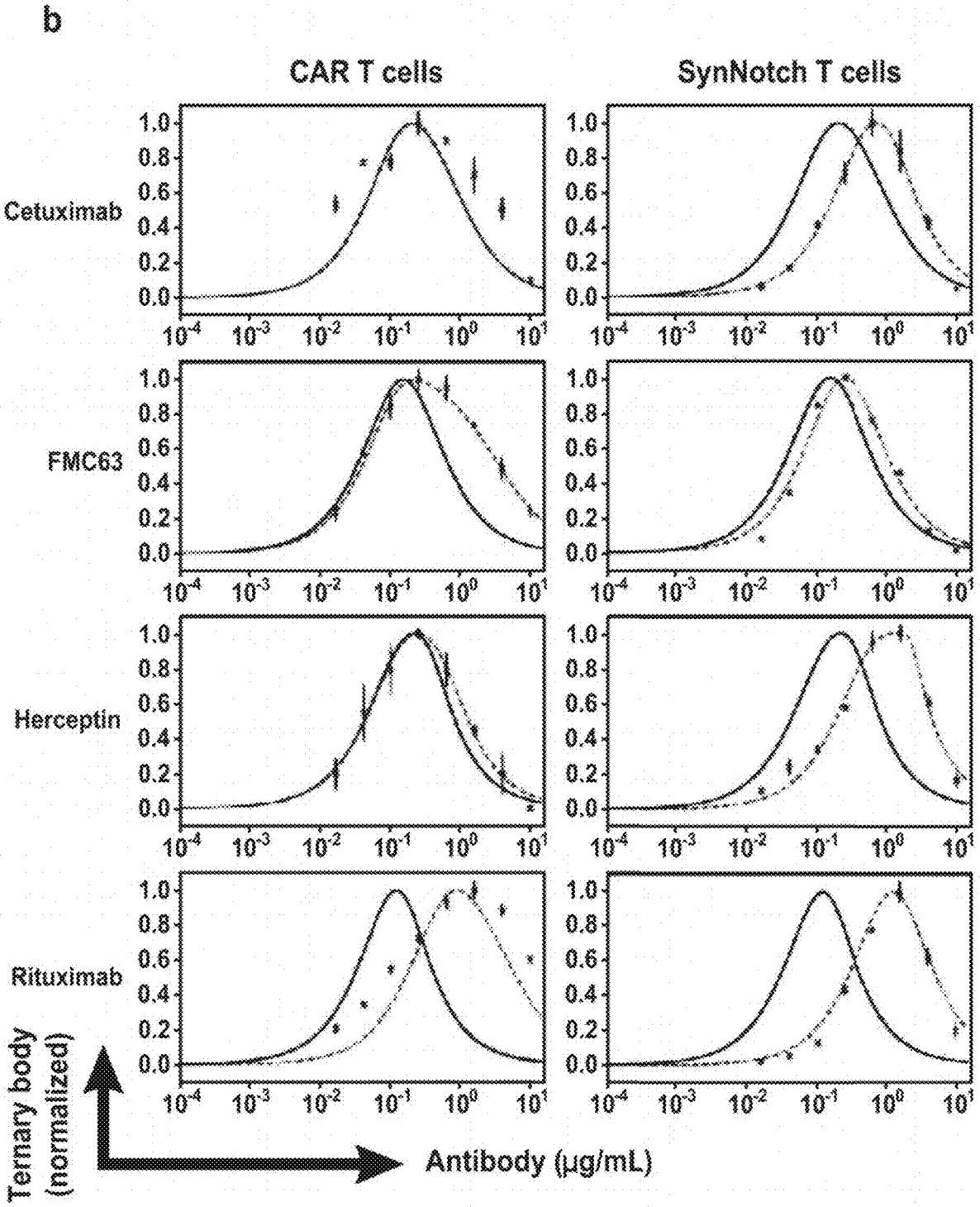
Figure 8C:
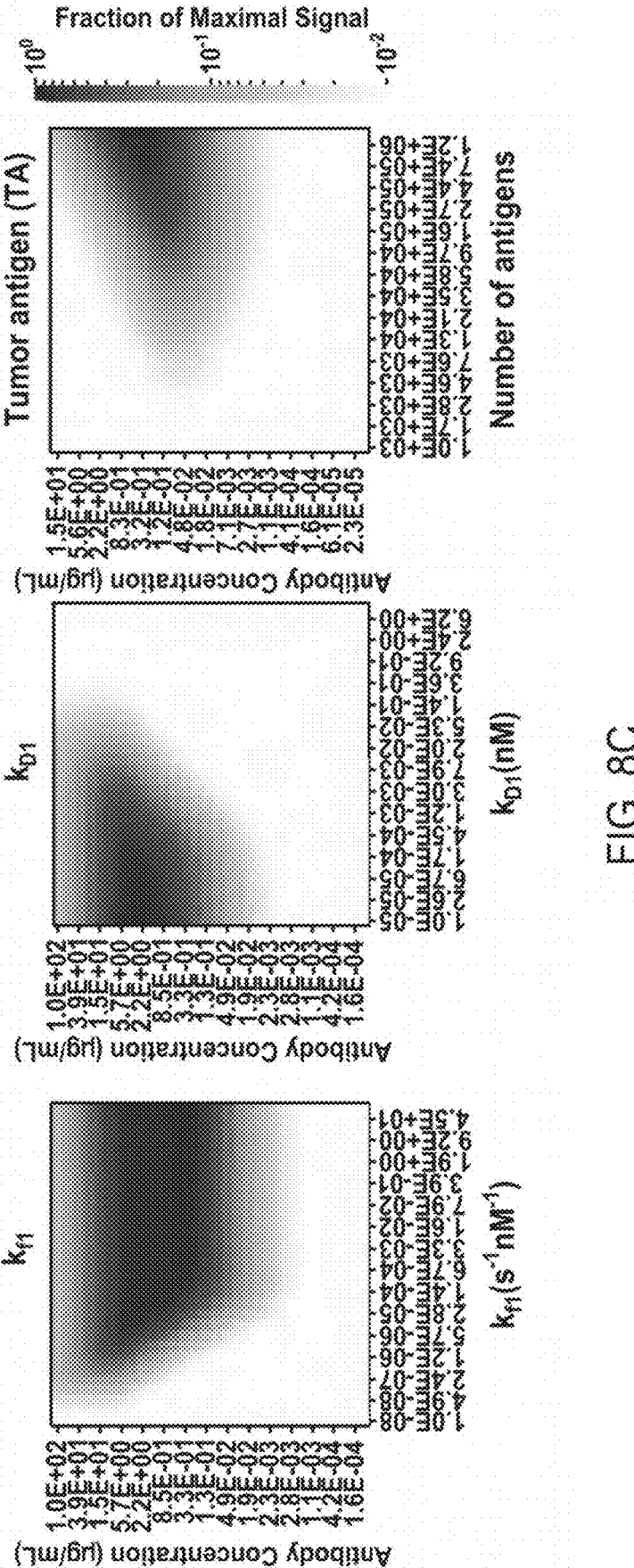

FIGS. 8A, 8B, and 8C show a mathematical model of three-body binding in the context of antibody mediated T Cell targeting. FIG. 8A shows a pictorial representation of the ODE model for SNAP receptor ternary body formation. FIG. 8B shows model simulations using parameters from the literature and after parameter estimation, compared to experimental results for four different antibody antigen pairs for CAR and SynNotch receptors. FIG. 8C shows parameter scans of $k_{f1}$ (binding rate of T cells to Antibody), $K_{D1}$ (dissociation constant between T cell and antibody), and the number of target antigens on the surface of the tumor.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

An "increase" can refer to any change that results in a greater amount of a symptom, disease, composition, condition or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular universal CAR T cell or universal synNotch cell is disclosed and discussed and a number of modifications that can be made to a number of molecules including the universal CAR T cell or universal synNotch cell are discussed, specifically contemplated is each and every combination and permutation of universal CAR T cell or universal synNotch cell and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Chimeric antigen receptor (CAR) T cells offer the opportunity to seek out and destroy cancer cells by recognizing tumor-associated antigens (TAA) expressed on their surface. These CAR T cells are engineered to express a TCR receptor where the MHC class I recognition portion of the receptor has been substituted with an antibody or antibody fragment that targets an antigen on a cancer cell and once bound turns on the effector mechanism of the T cell. Similarly, engineered T cells comprising synthetic notch (synNotch) secrete or display on their surface anti-tumor molecules that have an anti-tumor effect upon binding with TAA. synNotch receptors are designed to express antibody or an antibody fragment rather than the native notch receptor. Binding to the antibody or antibody fragment of a synNotch triggers cleavage of the notch receptor and release of a transcription factor when the desired TAA is bound. synNotch receptors can be further modified to incorporate specific or unique transcription elements to trigger expression of a desired genes.

However, these therapies are not without limitations. For example, no single tumor antigen is universally expressed by all cancer types and the tumor antigen could be down regulated in one subject's cancer and not down regulated in another. Thus, scFv in CAR or synNotch needs to be constructed for each tumor antigen to be targeted. This also means that if the first CAR or synNotch fails, a new CAR or Notch will have to be made. Moreover, traditional CAR T cells and synNotch are specific to the individual from whom the starting T cells are harvested and do not allow for a more global use of the same T cell. To overcome problems associated with adapting synNotch and CAR T cells to a new target antigen and/or new subject, new universal adaptor synNotch receptors and universal adaptor CARs are disclosed herein. The disclosed synNotch receptors and CARs achieve their universality through the use of adaptor molecules in the extracellular portion of the synNotch receptor or CAR and which adaptor molecules form a covalent bond with an antigen recognition element (FIGS. 2B and 5A). This system for creating universal CARs and synNotch receptors using adaptor molecules to form a covalent bond with an antigen recognition element represents a vast improvement over existing adaptor CAR T cells and is the first successful adaptor synNotch system ever created. Accordingly, disclosed herein are universal chimeric antigen receptors (CARs), wherein the CAR comprises an adaptor molecule, a CD8α hinge domain, and a CD3ζ signaling domain (FIGS. 5A and 5B). Also disclosed herein are universal synthetic Notch (synNotch) receptors, said synNotch receptors comprising an adaptor molecule, a notch core comprising one or more cleavage sites, and one or more transcription factors (FIGS. 3A and 3B).

Both the universal synNotch receptors and the universal CARs disclosed herein comprise adaptor molecules. These adaptor molecules facilitate the formation of a covalent bond with an antigen recognition element (such as for example, an antibody or antibody fragment) (FIG. 2D). Thus, covalent bonding can occur through pi-clamp; ligand directed yosyl chemistry; recombinant antibodies with BG incorporation through short peptide tags, sortase mediated labeling; unnatural amino acid mutagenesis followed by 'click' chemistry, [3+2] cycloaddition, split inteins, tetrazine ligation, Staudinger ligation, imine formation, thiol-ene reaction, native chemical ligation; biotin ligase mediated labeling; lipoic acid ligase mediated labeling; NHS-ester conjugation, bis-sulfone conjugation, glycan conjugating chemistry, or formyl glycine conversion. Covalent bond formation can also occur through the use of adaptor molecules that comprise polypeptide tags that covalently bind a target modification. Examples of polypeptide adaptor molecules include, but are not limited to SNAP-Tag® (which covalently bonds to a $O^6$-benzylguanine which can be inserted into the antigen recognition element), CLIP-Tag™ (which covalently bonds to a $O^2$-benzylcytosine which can be inserted into the antigen recognition element), Halotag® (which covalently bonds to a chloroalkane linker which can be inserted into the antigen recognition element), SpyTag (which covalently bonds to a Spy catcher peptide sequence which can be inserted into the antigen recognition element), SnoopTag (which covalently bonds to a Snoop catcher peptide sequence which can be inserted into the antigen recognition element), or Isopep-tag (which covalent bonds to its biding partner which can be inserted into the antigen recognition element). The formation of a covalent bond is a key improvement over other adaptor CAR T cell systems which rely on week interactions and which is sufficiently strong such that the bond is not broken upon antigen binding allowing for the Notch cleavage site(s) to be revealed in the synNotch receptor.

It is understood and herein contemplated that one of the greatest advantages of the disclosed universal CAR and/or universal synNotch receptors disclosed herein is the ability to specifically design the universal CAR and/or universal synNotch receptor to bind to any target of interest. This is accomplished through the use of an antigen recognition element which can be modified to covalently bond to the adaptor molecule on the universal CAR and/or universal synNotch receptor. For example, the modification of the antigen recognition element can be the inclusion of a Spy Catcher Protein (for forming a covalent bond when the adaptor molecule comprises a SpyTag peptide), Snoop Catcher protein (for forming a covalent bond when the adaptor molecule comprises a SnoopTag peptide), chloroalkane linker for forming a covalent bond when the adaptor molecule comprises a Halotag®), $O^6$-benzylguanine (for forming a covalent bond when the adaptor molecule comprises a SNAP-Tag®), $O^2$-benzylcytosine (for forming a covalent bond when the adaptor molecule comprises a CLIP-Tag™). Thus, in one aspect, disclosed herein are any engineered synNotch cells or CAR T cells disclosed herein, further comprising an antigen recognition element; wherein the antigen recognition element can be covalently linked to adaptor molecule. It is understood and herein contemplated that the antigen recognition element can be an antibody or any antigen recognizing fragment thereof (such as, for example, Fab, Fab'2, scFv, Fv, and the like). In one aspect, the antigen recognition element can comprise an anti-cancer-based monoclonal antibodies such as cetuximab (anti-EGFR), nimotuzumab (anti-EGFR), panitumumab (anti-EGFR), retuximab (anti-CD20), omalizumab (anti-CD20), tositumomab (anti-CD20), trastuzumab (anti-Her2), Herceptin (anti-Her2), gemtuzumab (anti-CD33), alemtuzumab (anti-CD52), FMC63 (anti-CD19), and bevacuzimab (anti-VEGF) or antigen recognizing fragment thereof. In some aspects, the antigen recognition element can comprise protein binding domains (such as, for example, Nanobodies and single domain antibodies (e.g., monobodies), lectins, DNA aptamers, RNA aptamers, any small molecule ligands for cell surface receptors (e.g., folic acid which is bound by the folic acid receptor), peptide/protein ligands for natural protein receptors (such as, for example, NKG2D and/or cytokines which can be bound to their natural receptors).

It is understood and herein contemplated that the disclosed CARs and synNotch receptors are made from and ultimately expressed on T cells for the CAR and any immune cell (e.g., T cell, a B cell, memory T cell, memory B cell, NK T cell, a monocyte, a natural killer cell, a dendritic cell, a macrophage, a regulatory T cell, a helper T cell, or a cytotoxic T cell), a neuron, an epithelial cell, and endothelial cell, or a stem cell for the synNotch receptor. The cells used to make and express the universal CARs and synNotch receptors disclosed herein as well as any cell comprising said receptors may be from an autologous, syngeneic or allogeneic source with the selection dependent on the disease to be treated and the means available to do so. When a T cell, suitable populations of effector cells that may be used in the methods include any immune cells with cytolytic activity, such as T cells. Exemplary sub-populations of T cells include, but are not limited to those expressing CD3+ including CD3+CD8+ T cells, CD3+CD4+ T cells, and NKT cells. In one aspect, the T cells are peripheral blood mononuclear cells (PBMC) of any HLA background from PBMCs and utilized in an autologous, syngeneic or allogeneic systems. T cells may also be isolated from any source, including but not limited to a tumor explant of the subject being treated or intratumoral T cells of the subject being treated. For the sake of convenience, the effector cells are commonly referred to herein as T cells, but it should be understood that any reference to T cells, unless otherwise indicated, is a reference to all effector cell types as defined herein. Accordingly, disclosed herein are engineered T cells comprising the universal CAR (universal CAR T cells) and/or universal synNotch (engineered universal synNotch T cell) disclosed herein. In one aspect, it is understood and herein contemplated that the synNotch receptor and CAR can be expressed on the same T cell. In such situations the antigen recognition element can be the same, allowing both synNotch transactivation of cytokines and T cell activation to occur. Alternatively, the synNotch receptor and CAR can comprise different antigen recognition elements. To ensure that the antigen recognition element on the CAR and synNotch are different, where both are present on the same cell, the synNotch receptor and CAR can comprise different adaptor molecules allowing for a different covalent interaction. Thus, in one aspect, disclosed herein are engineered T cell comprising any of the universal CAR and the universal synNotch receptors disclosed herein, wherein the CAR and synNotch receptor comprise different adaptor molecules.

In one aspect, it is understood and herein contemplated that for T cell activation of the CAR T cell to occur additional cellular signaling events need to occur beyond the CAR T cell antigen recognition element binding to its target. Co-stimulation is also required. Co-stimulation can occur via native interactions that occur during the activation of any T cell and already present on any CAR T cell such as the stimulation of CD28 and 4-1BB via interactions with their respective ligands B7 and 4-1BBL on the surface of the target cell. Alternatively, the universal CAR can further comprise one or more co-stimulation domains (such as, for example, signaling domains for CD27, CD28, ICOS, 4-1BB, or OX40), such that co-stimulation occurs upon the antigen recognition element binding its target without the further need of the target cell providing the necessary co-stimulatory signals (FIGS. 5A and 5B). Thus, in one aspect, disclosed herein are universal CAR comprising an adaptor molecule, a CD8α hinge domain, and a CD33 signaling domain; and wherein the CAR further comprises one or more co-stimulation domains (such as, for example, signaling domains for CD27, CD28, ICOS, 4-1BB, or OX40). Also disclosed herein are universal CAR T cells expressing any of the universal CARs disclosed herein further comprising one or more co-stimulation domains.

As noted above, the effector action of the universal synNotch receptor occurs through the transcriptional activation of a response genes in the cell. The one or more transcription factors (such as, for example, Gal4-VP64, Gal4-VP16, TetR-VP64, LacI-VP64, and the like) can be specifically designed to activate transcription of T cell where the response genes can be T cell effector molecules including, but not limited to IL-4, IL-10, FASL, IFN-γ, TNF-α, granzyme A. granzyme B, granulysin, and/or perforin. The transcriptional activation can occur through the use of native or designer transcription factors (Crispr/Cas9, TALEN, or zinc finger). Thus, in once aspect, disclosed herein are engineered T cells comprising a universal synthetic Notch (synNotch) receptor, wherein one or more transcription factors of the universal synNotch receptor activate expression of one or more native cell response genes (such as, for example, T cell effector molecules IL-4, IL-10, FASL, IFN-γ, TNF-α, granzyme A. granzyme B, granulysin, and/or perforin). Alternatively, it is contemplated herein that the transcription factor (such as, for example, Gal4-VP64, Gal4-VP16, TetR-VP64, LacI-VP64, and the like) can be specific for a transcriptional response element (such as, for example, Gal4-VP64, Gal4-VP16, TetR-VP64, LacI-VP64, and the like) on a vector expressing transgene system allowing for unique non-native interaction and expression of one or more response genes (such as, for example, IL-4, IL-10, FASL, IFN-γ, TNF-α, granzyme A. granzyme B, granulysin, and/or perforin). One or more response genes can be encoded on the vector along with the transcriptions response element and a promoter which drives the expression of the effector molecule. Thus, in one aspect, disclosed herein are engineered cells comprising a universal synthetic Notch (synNotch) receptor, further comprising a vector comprising with a transcriptional response element operatively linked to a promoter driving expression of one or more response genes (such as, for example, T cell effector molecules IL-4, IL-10, FASL, IFN-γ, TNF-α, granzyme A. granzyme B, granulysin, and/or perforin); wherein the transcriptional response element is specific for one or more of the transcription factors on the synNotch receptor (FIGS. 3A and 3B).

1. Homology/Identity

It is understood that one way to define any known variants and derivatives or those that might arise, of the disclosed genes and proteins herein is through defining the variants and derivatives in terms of homology to specific known sequences. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2:482 (1981), by the homology alignment algorithm of Needleman and Wunsch, *J. MoL Biol.* 48:443 (1970), by the search for similarity method of Pearson and Lipman, *Proc. Natl. Acad. Sci. U.S.A.* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

2. Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physicomechanical methods such as electroporation and direct diffusion of DNA, are described by, for example, Wolff, J. A., et al., *Science,* 247, 1465-1468, (1990); and Wolff, J. A. *Nature,* 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as chimeric antigen receptor or synNotch into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically, a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., *J. Virology* 61:1213-1220 (1987); Massie et al., *Mol. Cell. Biol.* 6:2872-2883 (1986); Haj-Ahmad et al., *J. Virology* 57:267-274 (1986); Davidson et al., *J. Virology* 61:1226-1239 (1987); Zhang "Generation and identification of recombinant adenovirus by liposome-mediated transfection and PCR analysis" *BioTechniques* 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Moullier, *Nature Genetics* 4:154-159 (1993); La Salle, *Science* 259:988-990 (1993); Gomez-Foix, *J. Biol. Chem.* 267:25129-25134 (1992); Rich, *Human Gene Therapy* 4:461-476 (1993); Zabner, *Nature Genetics* 6:75-83 (1994); Guzman, *Circulation Research* 73:1201-1207 (1993); Bout, *Human Gene Therapy* 5:3-10 (1994); Zabner, *Cell* 75:207-216 (1993); Caillaud, *Eur. J. Neuroscience* 5:1287-1291 (1993); and Ragot, *J. Gen. Virology* 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462-477 (1970); Brown and Burlingham, *J. Virology* 12:386-396 (1973); Svensson and Persson, *J. Virology* 55:442-449 (1985); Seth, et al., *J. Virol.* 51:650-655 (1984); Seth, et al., *Mol. Cell. Biol.* 4:1528-1533 (1984); Varga et al., *J. Virology* 65:6061-6070 (1991); Wickham et al., *Cell* 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, CA, which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically, the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., *Nature genetics* 8:33-41, 1994; Cotter and Robertson, *Curr Opin Mol Ther* 5:633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, MD), SUPERFECT (Qiagen, Inc. Hilden, Germany) and TRANSFECTAM (Promega Biotec, Inc., Madison, WI), as well as other liposomes developed according to procedures standard in the art. In addition, the disclosed nucleic acid or vector can be delivered in vivo by electroporation, the technology for which is available from Genetronics, Inc. (San Diego, CA) as well as by means of a SONOPORATION machine (ImaRx Pharmaceutical Corp., Tucson, AZ).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and Mckenzie, *Immunolog. Reviews*, 129:57-80, (1992); and Roffler, et al., *Biochem. Pharmacol*, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subject=s cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature*, 273:113 (1978)). The immediate early promoter of the human cytomegalovirus is conveniently obtained as a HindIII E restriction fragment (Greenway, P. J. et al., *Gene* 18:355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78:993 (1981)) or 3' (Lusky, M. L., et al., *Mol. Cell Bio.* 3:1108 (1983)) to the transcription unit. Furthermore, enhancers can be within an intron (Banerji, J. L. et al., *Cell* 33:729 (1983)) as well as within the coding sequence itself (Osborne, T. F., et al., *Mol. Cell Bio.* 4:1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1:327 (1982)), mycophenolic acid, (Mulligan, R. C. and Berg, P. *Science* 209:1422 (1980)) or hygromycin, (Sugden, B. et al., *Mol. Cell. Biol.* 5:410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

4. Antibodies (1) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with a given antigen target. The antibodies can be tested for their desired activity using the in vitro assays described herein, or by analogous methods, after which their in vivo therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces mono clonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody or fragments thereof" encompasses chimeric antibodies and hybrid antibodies, with dual or multiple antigen or epitope specificities, and fragments, such as F(ab')2, Fab', Fab, Fv, scFv, and the like, including hybrid fragments. Thus, fragments of the antibodies that retain the ability to bind their specific antigens are provided. For example, fragments of antibodies which maintain target binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual.* Cold Spring Harbor Publications, New York, (1988)).

Also included within the meaning of "antibody or fragments thereof" are conjugates of antibody fragments and antigen binding proteins (single chain antibodies).

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(2) Human Antibodies

The disclosed human antibodies can be prepared using any technique. The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an sFv, Fv, Fab, Fab', F(ab')2, or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature*, 321:522-525 (1986), Reichmann et al., *Nature*, 332:323-327 (1988), and Presta, *Curr. Opin. Struct. Biol.*, 2:593-596 (1992)).

Methods for humanizing non-human antibodies are well known in the art. For example, humanized antibodies can be generated according to the methods of Winter and co-workers (Jones et al., *Nature*, 321:522-525 (1986), Riechmann et al., *Nature*, 332:323-327 (1988), Verhoeyen et al., *Science*, 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

5. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol.*

*Immunother.,* 35:421-425, (1992); Pietersz and Mckenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies,* Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

6. Kits

Disclosed herein are kits that are drawn to reagents that can be used in practicing the methods disclosed herein. The kits can include any reagent or combination of reagent discussed herein or that would be understood to be required or beneficial in the practice of the disclosed methods and making the disclosed universal CAR, universal synNotch, universal CAR T cells, and/or universal synNotch cells. For example, the kits could include antibodies or fragments thereof and expression vectors to discussed in certain embodiments of the methods and composition, as well as the buffers and enzymes required.

C. Method of Treating Disease

The disclosed universal synNotch cells and universal CAR T cells can be used to treat any disease where uncontrolled cellular proliferation occurs such as cancers, autoimmune disorders, autoinflammatory disorders, and infectious disease. Accordingly, in one aspect, disclosed herein are methods of treating a cancer, autoimmune disorders, autoinflammatory disorders, and infectious disease in a subject comprising administering to the subject a therapeutically effective amount of any of the engineered universal CAR T cells and/or universal synNotch cells disclosed herein.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of a disease or an infection.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

The term "therapeutically effective" refers to the amount of the composition used is of sufficient quantity to ameliorate one or more causes or symptoms of a disease or disorder. Such amelioration only requires a reduction or alteration, not necessarily elimination.

A non-limiting list of different types of cancers that can be treated through the administration of the disclosed universal CAR T cells and/or universal synNotch cells is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, or pancreatic cancer.

Compounds disclosed herein may also be used for the treatment of precancer conditions such as cervical and anal dysplasias, other dysplasias, severe dysplasias, hyperplasias, atypical hyperplasias, and neoplasias.

It is intended herein that the disclosed methods of inhibiting, reducing, and/or treating a cancer can comprise the administration of any anti-cancer agent known in the art including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane),Arranon (Nelarabine), Arsenic Trioxide, Arzerra (Ofatumumab), Asparaginase *Erwinia chrysanthemi*, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPOX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil— Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate). Also contemplated herein are chemotherapeutics that are PD1/PDL1 blockade inhibitors (such as, for example, lambrolizumab, nivolumab, pembrolizumab, pidilizumab, BMS-936559, Atezolizumab, Durvalumab, or Avelumab).

As noted above, the disclosed universal synNotch cell and/or universal CAR T cell can be used to treat autoimmune diseases (i.e., a set of diseases, disorders, or conditions resulting from an adaptive immune response (T cell and/or B cell response) against the host organism). Examples of autoimmune diseases including, but not limited to Achalasia, Acute disseminated encephalomyelitis, Acute motor axonal neuropathy, Addison's disease, Adiposis dolorosa, Adult Still's disease, Agammaglobulinemia, Alopecia areata, Alzheimer's disease, Amyloidosis, Ankylosing spondylitis, Anti-GBM/Anti-TBM nephritis, Antiphospholipid syndrome, Aplastic anemia, Autoimmune angioedema, Autoimmune dysautonomia, Autoimmune encephalomyelitis, Autoimmune enteropathy, Autoimmune hemolytic anemia, Autoimmune hepatitis, Autoimmune inner ear disease (AIED), Autoimmune myocarditis, Autoimmune oophoritis, Autoimmune orchitis, Autoimmune pancreatitis, Autoimmune polyendocrine syndrome, Autoimmune retinopathy, Autoimmune urticaria, Axonal & neuronal neuropathy (AMAN), Baló disease, Behcet's disease, Benign mucosal emphigoid, Bickerstaff's encephalitis, Bullous pemphigoid, Castleman disease (CD), Celiac disease, Chagas disease, Chronic fatigue syndrome, Chronic inflammatory demyelinating polyneuropathy (CIDP), Chronic recurrent multifocal osteomyelitis (CRMO), Churg-Strauss Syndrome (CSS), Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Diabetes mellitus type 1, Discoid lupus, Dressler's syndrome, Endometriosis, Enthesitis, Eosinophilic esophagitis (EoE), Eosinophilic fasciitis, Erythema nodosum, Essential mixed cryoglobulinemia, Evans syndrome, Felty syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's encephalopathy, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenia purpura (ITP), Inclusion body myositis (IBM), Interstitial cystitis (IC), Inflamatory Bowel Disease (IBD), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus nephritis, Lupus vasculitis, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Ord's thyroiditis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Rheumatoid vasculitis, Sarcoidosis, Schmidt syndrome, Schnitzler syndrome, Scleritis, Scleroderma, Sjögren's syndrome, Sperm & testicular autoimmunity, Stiff person syndrome (SPS), Subacute bacterial endocarditis (SBE), Susac's syndrome, Sydenham chorea, Sympathetic ophthalmia (SO), Systemic Lupus Erythematosus, Systemic scleroderma, Takayasu's arteritis, Temporal arteritis/Giant cell arteritis, Thrombocytopenia purpura (TTP), Tolosa-Hunt syndrome (THS), Transverse myelitis, Type 1 diabetes, Ulcerative colitis (UC), Undifferentiated connective tissue disease (UCTD), Urticaria, Urticarial vasculitis, Uveitis, Vasculitis, Vitiligo, Vogt-Koyanagi-Harada Disease, and Wegener's granulomatosis (or Granulomatosis with Polyangiitis (GPA)).

Also disclosed herein are methods of treating an autoinflammatory diseases (i.e., disorders where the innate immune response attacks host cells) comprising administering to a subject with an autoinflammatory disease the universal CAR T cells and/or universal synNotch cells disclosed herein. Examples of autoinflammatory disorders include asthma, graft versus host disease, allergy, transplant rejection, Familial Cold Autoinflammatory Syndrome (FCAS), Muckle-Wells Syndrome (MWS), Neonatal-Onset Multisystem Inflammatory Disease (NOMID) (also known as Chronic Infantile Neurological Cutaneous Articular Syndrome (CINCA)), Familial Mediterranean Fever (FMF), Tumor Necrosis Factor (TNF)-Associated Periodic Syndrome (TRAPS), TNFRSF11A-associated hereditary fever disease (TRAPS11), Hyperimmunoglobulinemia D with Periodic Fever Syndrome (HIDS), Mevalonate Aciduria (MA), Mevalonate Kinase Deficiencies (MKD), Deficiency of Interleukin-1ß (IL-1ß) Receptor Antagonist (DIRA) (also known as Osteomyelitis, Sterile Multifocal with Periostitis Pustulosis), Majeed Syndrome, Chronic Nonbacterial Osteomyelitis (CNO), Early-Onset Inflammatory Bowel Disease, Diverticulitis, Deficiency of Interleukin-36-Receptor Antagonist (DITRA), Familial Psoriasis (PSORS2), Pustular Psoriasis (15), Pyogenic Sterile Arthritis, Pyoderma Gangrenosum, and Acne Syndrome (PAPA), Congenital sideroblastic anemia with immunodeficiency, fevers, and developmental delay (SIFD), Pediatric Granulomatous Arthritis (PGA), Familial Behçets-like Autoinflammatory Syndrome, NLRP12-Associated Periodic Fever Syndrome, Proteasome-associated Autoinflammatory Syndromes (PRAAS), Spondyloenchondrodysplasia with immune dysregulation (SPENCDI), STING-associated vasculopathy with onset in infancy (SAVI), Aicardi-Goutieres syndrome, Acute Febrile Neutrophilic Dermatosis, X-linked familial hemophagocytic lymphohistiocytosis, and Lyn kinase-associated Autoinflammatory Disease (LAID).

As noted above, the disclosed universal CAR T cells and universal synNotch cells can be used to treat disease resulting from an infection with a bacterium, virus, fungi, and/or parasite.

In one aspect, the infectious disease being treated can be the result of an infection with a virus selected from the group consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

In one aspect, the infectious disease being treated can be the result of an infection with a bacteria selected from the group of bacteria consisting of *Mycobaterium tuberculosis, Mycobaterium bovis, Mycobaterium bovis* strain BCG, BCG substrains, *Mycobaterium avium, Mycobaterium intracellular, Mycobaterium africanum, Mycobaterium kansasii, Mycobaterium marinum, Mycobaterium ulcerans, Mycobaterium avium* subspecies paratuberculosis, *Nocardia asteroides,* other *Nocardia* species, *Legionella pneumophila,* other *Legionella* species, *Salmonella typhi, Salmonella enterica,* other *Salmonella* species, *Shigella boydii, Shigella dysenteriae, Shigella sonnei, Shigella flexneri,* other *Shigella* species, *Yersinia pestis, Pasteurella haemolytica, Pasteurella multocida,* other *Pasteurella* species, *Actinobacillus pleuropneumoniae, Listeria monocytogenes, Listeria ivanovii, Brucella abortus,* other *Brucella* species, *Cowdria ruminantium, Borrelia burgdorferi, Bordetella avium, Bordetella pertussis, Bordetella bronchiseptica, Bordetella trematum, Bordetella hinzii, Bordetella pteri, Bordetella parapertussis, Bordetella ansorpii* other *Bordetella* species, *Burkholderia mallei, Burkholderia psuedomallei, Burkholderia cepacian, Chlamydia pneumoniae, Chlamydia trachomatis, Chlamydia psittaci, Coxiella burnetii, Rickettsial* species, *Ehrlichia species, Staphylococcus aureus, Staphylococcus epidermidis, Streptococcus pneumoniae, Streptococcus pyogenes, Streptococcus agalactiae, Escherichia coli, Vibrio cholerae, Campylobacter* species, *Neiserria meningitidis, Neiserria gonorrhea, Pseudomonas aeruginosa,* other *Pseudomonas* species, *Haemophilus influenzae, Haemophilus ducreyi,* other *Hemophilus* species,

33

*Clostridium tetani*, other *Clostridium* species, *Yersinia enterolitica*, and other *Yersinia* species. In one aspect the bacteria is not *Bacillus anthracis*.

In another aspect, the infectious disease being treated can be the result of an infection with a fungi selected from the group consisting of *Candida albicans, Cryptococcus neoformans, Histoplama capsulatum, Aspergillus fumigatus, Coccidiodes immitis, Paracoccidioides brasiliensis, Blastomyces dermitidis, Pneumocystis carnii, Penicillium marneffi*, and *Alternaria alternata*.

In another aspect, the infectious disease being treated can be the result of an infection with a parasite selected from the group of parasitic organisms consisting of *Toxoplasma gondii, Plasmodium falciparum, Plasmodium vivax, Plasmodium malariae*, other *Plasmodium* species, *Entamoeba histolytica, Naegleria fowleri, Rhinosporidium seeberi, Giardia lamblia, Enterobius vermicularis, Enterobius gregorii, Ascaris lumbricoides, Ancylostoma duodenale, Necator americanus, Cryptosporidium* spp., *Trypanosoma brucei, Trypanosoma cruzi, Leishmania major*, other *Leishmania* species, *Diphyllobothrium latum, Hymenolepis nana, Hymenolepis diminuta, Echinococcus granulosus, Echinococcus multilocularis, Echinococcus vogeli, Echinococcus oligarthrus, Diphyllobothrium latum, Clonorchis sinensis; Clonorchis viverrini, Fasciola hepatica, Fasciola gigantica, Dicrocoelium dendriticum, Fasciolopsis buski, Metagonimus yokogawai, Opisthorchis viverrini, Opisthorchis felineus, Clonorchis sinensis, Trichomonas vaginalis, Acanthamoeba species, Schistosoma intercalatum, Schistosoma haematobium, Schistosoma japonicum, Schistosoma mansoni*, other *Schistosoma* species, *Trichobilharzia regenti, Trichinella spiralis, Trichinella britovi, Trichinella nelsoni, Trichinella nativa*, and *Entamoeba histolytica*.

D. EXAMPLES

The following examples are put forth so as to provide those of ordinary skill in the art with a complete disclosure and description of how the compounds, compositions, articles, devices and/or methods claimed herein are made and evaluated and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Posttranslational Covalent Assembly of CAR and synNotch Receptors for Programmable Antigen Targeting Engineered antigen receptors are revolutionizing the treatment of blood cancers and show promise in cell therapies treating a wide range of other diseases. The most clinically advanced of these technologies are chimeric antigen receptors (CARs), synthetic T cell receptors most often comprised of an antigen-specific antibody single chain variable fragment (scFv) fused by spacer and transmembrane domains to intracellular T cell signaling domains. Upon binding to a target antigen, CARs stimulate T cell activation and effector functions including cytokine production, cell proliferation, and target cell lysis. Adoptively transferred CAR T cells targeting the B cell antigen CD19 are now FDA-approved and have been highly successful in treating refractory acute lymphoblastic leukemia. Creating CARs against additional targets to treat other types of cancer and immune-related diseases is a major research focus. Another class of highly versatile antigen receptors are synthetic Notch, "synNotch" receptors which consist of an antigen binding domain, the Notch core protein from the Notch/Delta signaling pathway, and a transcription factor. Instead of activating T cell signaling upon binding to the target antigen, the Notch core protein is cleaved by endogenous cell proteases thus releasing the transcription factor from the cell membrane. Subsequent nuclear translocation leads to transcriptional regulation of one or more target genes. These receptors are highly modular, they can be created to target different cell surface antigens by changing the scFv, and can positively or negatively regulate any gene of interest by either fusing different transcription factors as components of the receptors or by changing the transgenes under their control. This versatile receptor type receives increasing clinical interest in immunotherapies as well as applications to tissue engineering.

To gain additional control over CAR function, a "switchable" adaptor CAR systems was developed for which the CAR, instead of directly binding to an antigen on a target cell, binds to common tag molecule fused or conjugated to an antigen-specific antibody. These switchable adaptor CAR systems are designed such that patients are infused with a tagged, antigen-specific antibody that binds to target cells and T cells expressing AT-CARs that react with the tagged antibodies on the surface of target cells. They are also referred to as "universal CARs" as they have the potential to allow for one population of T cells to target multiple tumor antigens by administering different antibodies sequentially or simultaneously. Additionally, the activity of the adaptor CARs can be tuned by altering the concentration of tagged antibodies or halting antibody administration for better control over potential toxicities resulting from over-active CAR T cells. To date several adaptor CAR systems have been developed recognizing a variety of peptides or small molecules conjugated to antibodies including biotin, fluorescein isothiocyanate (FITC), peptide neo-epitopes (PNE), Fcgamma, and leucine zippers, and the first adaptor CAR system is currently in clinical trials.

Here, key advances were described in antigen receptor design—the creation of a switchable adaptor synNotch system and the creation of a novel universal CAR system that acts through self-labeling enzyme chemistry. The first attempt to create a switchable adaptor synNotch system that functioned through transient binding of the receptor to an antibody was unsuccessful, and it was reasoned that a stronger antibody/receptor interaction would be necessary. Seeking to create a self-labeling synNotch receptor that would perform a chemical reaction to covalently fuse with the adaptor antibody, a synNotch receptor containing the SNAPtag protein was generated. SNAPtag is a modified human O-6-methylguanine-DNA methyltransferase (MGMT) that was engineered to react to benzylguanine, a bio-orthogonal tag molecule, and is known to be specific and efficient at self-labeling in both cells and animals (FIG. 2A). Herein is descried that a CARcontaining the SNAPtag was created and characterized as there is a positive correlation between CAR function and the CAR/adaptor binding affinity. The SNAP-CAR and SNAP-synNotch systems are highly modular receptor platforms for diverse programming of cell behaviors using covalent chemistry (FIG. 2B, 2C, 2D).

US 12,655,213 B2

35 a) Results (1) Engineering a Self-Labeling SNAP Universal synNotch Receptor.

The first attempts to create a universal synNotch system with the biotin-avidin tag-receptor interaction using the biotin-binding protein, 'mSA2' as the targeting domain were unsuccessful, leading to the seeking of a higher-affinity CAR-tag interaction design. The goal of this initial system was to re-direct receptor activity by combining mSA2-synNotch cells with biotinylated antibodies, similar to the mSA2 CAR T cell system (FIG. 1A). The mSA2 synNotch receptor was cloned into a lentiviral expression vector and transduced Jurkat cells with the receptor along with a Gal4-driven TagBFP reporter gene. Assaying the cells by flow cytometry, it was found that the receptor was efficiently expressed on the cell surface. Furthermore, incubating mSA2-synNotch cells with plates labeled with biotinylated antibody showed some TagBFP response gene activation when stimulated with plate-immobilized biotin (FIG. 1B). However, the receptor was ultimately not functional at detecting cell-surface antigen, as no receptor activation was seen when the cells were incubated with biotinylated antibody-labeled tumor cells (FIG. 1C). It was posited that the lack of signaling by the mSA2 synNotch receptor compared to potent signaling by mSA2 CAR T cells was the result of the Notch receptor's differing signaling mechanism that requires a pulling force. It was reasoned that a stronger receptor to tag binding interaction (mSA2-biotin $K_d$=5.5× $10^9$) was required to create a functional, universal synNotch system.

Next a synNotch receptor was generated containing the SNAPtag self-labeling enzyme which forms a covalent bond via a benzene ring with a BG-tagged molecule (FIG. 3A). The goal of this system is to re-direct receptor activation by combining SNAP-synNotch cells with BG-labeled antibodies (FIGS. 2B and 2C). A lentiviral vector encoding the SNAP-synNotch receptor was generated and transduced Jurkat cells (FIG. 3B). Antibody labeling of the myc epitope tag and labeling with a fluorophore-conjugated BG reagent confirmed cell surface expression of the receptor and SNAP-BG cell-surface labeling activity (FIG. 3C).

To generate the adaptor targeting molecules, BG was conjugated to several clinically relevant antibodies using a BG-NHS ester (FIG. 2A). These antibodies included Rituximab targeting CD20, FMC63 targeting CD19, Herceptin targeting HER2, and Cetuximab targeting EGFR. The NHS ester conjugates BG to N-termini or lysines in the protein. While the conjugation products are heterogenous, the average number of BG molecules conjugated to each antibody were quantified by a SNAP protein-labeling assay in which SNAP-conjugation leads to a shift in the antibodies' molecular weight that can be resolved by SDS-PAGE electrophoresis. The numbers of BG molecules per antibody ranged from 2.0-2.8 as summarized in Table 1. The antigen expression and BG-antibody staining of various target cell lines were characterized by flow cytometry in which the antibodies displayed expected specificities (FIG. 4).

TABLE 1

Quantification of the number of BG molecules conjugated per antibody.

| Antibody | Antigen | # of BG/Antibody |
|---|---|---|
| Rituximab | CD20 | 2.8 |
| FMC63 | CD19 | 2 |
| Cetuximab | EGFR | 2.6 |
| Herceptin | HER2 | 2.3 |
| Rituximab-Fab | CD20 | 2.5 |

Next, the BG-conjugated FMC63 antibody (FMC63-BG) was tested for its ability to activate synNotch signaling in response to CD19 positive tumor cells. A co-incubation assay of SNAP-synNotch cells and CD19 positive and negative tumor cells was performed in the presence of different levels of FMC63-BG, and after 48 hours TagBFP response gene expression was assayed for by flow cytometry. TagBFP expression was significantly up-regulated in response to CD19 positive tumor cells for various concentrations of antibody. Receptor activation was sensitive, significant activation being observed at an antibody concentration as low as 0.04 ug/mL and increasing to a peak at 0.25 ug/mL. Response gene activation then decreased with increasing antibody before being completely inhibited at a concentration of 10 μg/mL, indicative of a hook effect, which is commonly observed with chemical and cell processes that involve ternary body formation (FIG. 3D).

It was found that BG-conjugated antibodies targeting other antigens were also capable of activating the SNAP-synNotch receptor in an antigen-specific manner (FIG. 3D). Similar co-incubation assays of SNAP-synNotch cells and antigen positive and negative tumor cells were performed in the presence of different levels of BG-conjugated Cetuximab, Herceptin, and Rituximab antibodies and assayed for TagBFP response gene expression by flow cytometry. Significant up-regulation of TagBFP was again observed for each of the tested antibodies at several antibody concentrations and in a target antigen-specific manner. Each of the antibodies displayed a similar activation pattern in which activation increased with the antibody dose until it peaked and then higher doses began to inhibit activation. Receptor activation was also target cell dose-dependent, having optimal activity at high target to SNAP-synNotch cell ratios as shown in Table 2.

TABLE 2

Effector to target effect on SNAP-synNotch receptor activity

| | SNAP-synNotch Cells (Millions) | | | | | | | | | | | |
|---|---|---|---|---|---|---|---|---|---|---|---|---|
| Raji Cells (Millions) | 1 | 0.5 | 0.1 | 0.01 | 1 | 0.5 | 0.1 | 0.01 | 1 | 0.5 | 0.1 | 0.01 |
| | 0 μg/mL FMC63-BG | | | | 0.1 μg/mL FMC63-BG | | | | 1.0 μg/mL FMC63-BG | | | |
| 1 | 431 | 463 | 551 | 541 | 748 | 955 | 1176 | 1518 | 1970 | 2877 | 4219 | 4434 |
| 0.5 | 485 | 525 | 557 | 505 | 979 | 1125 | 1939 | 1809 | 1813 | 2683 | 4567 | 5349 |

TABLE 2-continued

| | Effector to target effect on SNAP-synNotch receptor activity | | | | | | | | | | | |
|---|---|---|---|---|---|---|---|---|---|---|---|---|
| | SNAP-synNotch Cells (Millions) | | | | | | | | | | | |
| Raji Cells (Millions) | 1 | 0.5 | 0.1 | 0.01 | 1 | 0.5 | 0.1 | 0.01 | 1 | 0.5 | 0.1 | 0.01 |
| | 0 μg/mL FMC63-BG | | | | 0.1 μg/mL FMC63-BG | | | | 1.0 μg/mL FMC63-BG | | | |
| 0.1 | 447 | 483 | 470 | 341 | 1158 | 1568 | 2537 | 3397 | 1218 | 1488 | 2264 | 2468 |
| 0.01 | 445 | 522 | 511 | 286 | 550 | 732 | 1016 | 1823 | 519 | 667 | 984 | 806 |

Flow cytometry analysis of the activation of SNAP-syn-Notch cells co-incubated with the indicated target cell lines and FMC63-BG antibody at the indicated cell numbers and antibody concentrations for 48 hours for TagBFP output gene expression reported as mean fluorescence intensity (MFI)

The SNAP-synNotch receptor was capable of regulating expression of the IL-7 response gene, a candidate therapeutic gene of interest for its ability to promote T cell proliferation. An IL-7 response gene expression construct was generated in which the TagBFP gene was replaced by the IL-7 coding region. This construct is again transcriptionally activated by the Gal4-VP64 transcription factor upon receptor activation. SNAP-synNotch cells were transduced with this response vector and co-incubated them with several different antibodies and antigen positive and negative tumor cells for evaluation of IL-7 response gene expression by ELISA (FIG. 3E). Similar to TagBFP response gene activation, IL-7 was significantly up-regulated in an antigen-specific and antibody dose-responsive manner confirming the output gene modularity of the SNAP-synNotch system.

(2) Engineering Self-Labeling SNAP Switchable Adaptor CAR.

Next a switchable adaptor CAR system was created using the SNAPtag self-labeling enzyme to re-target T cell receptor signaling when combined with BG-tagged antibodies (FIG. 2D). The SNAPtag domain was cloned into a lentiviral vector containing the standard CAR components including the CD8α hinge and transmembrane domains, the 4-1BB cytoplasmic co-signaling domain, the CD3zeta T cell signaling cytoplasmic domain, and a TagBFP reporter gene co-expressed via a T2A co-translational peptide (FIGS. 5A and 5B). This vector was packaged into lentivirus particles and transduced Jurkat cells. The receptor was efficiently expressed and that the SNAPtag protein was functional as indicated by TagBFP expression and staining with a BG-fluorophore reagent and analysis by flow cytometry (FIG. 5C).

Next was tested whether BG-conjugated antibodies could be combined with SNAP-CAR Jurkat cells to target their T cell activation signaling in an antibody-dependent manner. SNAP-CAR cells were co-incubated with various antigen positive or negative tumor cell lines and various doses of BG-conjugated antibodies. After 24 hours the cells were assayed for T cell signaling activation by staining with antibodies for T cell activation marker CD25 that is up-regulated upon T cell activation and CD62L which is down-regulated. The activation of these markers was assessed in SNAP-CAR cells by specifically gating on the TagBFP CAR+ cell population. It was found that markers were controlled in an antigen-specific and dose-responsive manner by the BG-conjugated antibodies (FIG. 5D). Similar to the activation of the SNAP-synNotch cells, the SNAP-CAR activation increased with increasing antibody concentration, until reaching a peak dose/activation level between 0.1-1.0 ug/mL, before steadily decreasing, again indicative of a hook effect.

(3) the SNAP-CAR is Functional in Primary Human T Cells.

Next tested was the expression level and functional activity of the SNAP-CAR in primary human T cells. Primary human T cells were transduced with SNAP-CAR lentivirus and expanded them. Staining with the BG-fluorophore and assaying by flow cytometry, it was found that the SNAP receptor was efficiently expressed in ~40% of cells in a manner that correlated well with the expression of the TagBFP marker gene (FIG. 6A). To test their functional activity, SNAP-CAR T cells were co-incubated with various antigen positive or negative tumor cell lines and 1 μg/mL of BG-conjugated antibodies for 24 hours. Targeted antigens included CD20, EGFR, and Her2. Analyzing the supernatants of the co-incubated cells by ELISA it was found that the SNAP-CAR T cells can be re-directed by the BG-antibodies to produce significant amounts of IFNγ only when target cells expressed the antigen recognized by the co-administered antibody (FIG. 6B). Analyzing co-incubated cells by flow cytometry, it was found that the antibodies also led to induction of T cell activation markers, up-regulation of CD69 and CD107a and down-regulation of CD62L, as well as potent target cell lysis (FIGS. 6C and 6D). Again, T cell marker activation and target cell lysis were significantly higher only when the co-administered antibody targeted an antigen expressed by the co-administered cells. In addition to full length IgG antibodies, a BG-conjugated Fab fragment of Rituximab was also tested. This molecule, more similar to a traditional CAR containing an scFv antibody fragment, also showed potent activity for each of the effector functions equal to or greater than that of the full-length Rituximab.

(4) BG-Antibody Pre-Loading Experiments to Investigate the Receptor Signaling Mechanism.

Further investigating the mechanism of SNAP-SynNotch receptor activation, it was found that tumor-cells pre-labeled with BG-conjugated antibodies can activate the SNAP-synNotch cells while in contrast SNAP-synNotch cells that were pre-labeled with BG-conjugated antibody were not effective. CD19 positive and negative tumor cells were labeled with BG-conjugated antibody, washing away residual unbound antibody, and co-incubated these cells with SNAP-synNotch cells for 48 hours. Evaluating response gene activation, it was found that labeled tumor cells significantly up-regulated the expected gene programs to a level comparable to the peak level of activation in the previous dose-response assay (FIG. 7A). The SNAP-synNotch cells were pre-labeled with BG-conjugated antibody and after washing away residual antibody, a similar co-incubation assay was performed with CD19 positive and negative tumor cells. No significant response gene activation was observed (FIG. 7B).

Performing the same pre-staining experiments with SNAP-CAR cells, it was found that the SNAP-CAR was functional both when the receptors were pre-assembled by pre-loading SNAP-CAR cells with antibody or when the tumor cells are pre-labeled with BG-conjugated antibodies. CD20 positive and negative tumor cells were labeled with BG-conjugated antibody, washed away residual unbound antibody, and co-incubated these cells with Jurkat SNAP-CAR cells for 24 hours. Evaluating response gene activation, it was found that labeled tumor cells led to significant up-regulation of response gene expression to a level comparable to the peak level of activation in the previous dose-response assay (FIG. 7A). The SNAP-CAR cells were then pre-labeled with BG-labeled antibody and after washing away residual antibody, a similar co-incubation assay order of magnitude of each antibody dose expected to yield maximum receptor signaling (FIG. 8B). The sum of squared error (SSE) calculations was used to measure error in model simulations against experimental results. With the exception of Rituximab, model simulations using literature values alone, resulted in good recapitulations of experimental data (average SSE with literature values=1.03) (Table 4). Next, using SciPy, the sum of squared error was minimized to optimize the kinetic parameters and better fit the model to the experimental data for each antibody pair. During parameter estimation, the literature values were used as initial estimates and bounded within one order of magnitude. With these constraints, the model error was minimized in seven of the experimental results to (average SSE after fitting=0.09) (Table 4).

TABLE 3

| Experimental Setup | | |
|---|---|---|
| Description | Value | Units |
| Well Volume | 150 | uL |
| Number of T cells | 150,000 | cells |
| Number of Tumor Cells | 400,000 | cells |
| $K_f$ for BG-site covalent bonding (Gautier 2008) | 2.8e−05 | $nM^{-1}sec^{-1}$ |

| Antigen Parameters | |
|---|---|
| Antigen | Range |
| Cd19 | 10,000-500,000 |
| CD20 | 100,000-300,000 |
| EGFR | 100,000-1,000,000 |
| HER2 | 150,000-1,000,000 |

| Kinetic Parameters | | | | | |
|---|---|---|---|---|---|
| Antibody | Antigen | $K_f (nM^{-1}sec^{-1})$ | $K_r (sec^{-1})$ | $K_{equilibrium} (nM)$ | Citation |
| Cetuximab | EGFR | 3.10e−03 | 5.80e−03 | 1.87e−00 | Talavera 2009 |
| FMC63 | CD19 | 6.24e−04 | 5.50e−04 | 8.81e−01 | Kramer 2017 |
| Herceptin | HER2 | 5.70e−05 | 1.20e−06 | 2.11e−01 | Bondza 217 |
| Rituximab | CD20 | 5.56e−04 | 1.11e−04 | 2.00e−01 | Melhus 2007 | was performed with CD20 or CD19 positive and negative tumor cells. Significant T cell up-regulation of T cell activation was observed, however, to a lower magnitude than that observed with pre-labeled cancer cells (FIG. 7B).

(5) Mathematical Model of Switchable Adaptor Complex Formation.

To gain a better understanding of the switchable adaptor receptor signaling and the observed hook effect, a continuous mathematical model of the ternary complex formation between T cell, adaptor antibody, and target cell was generated. Using Python Jupyter Notebook, a generalizable model of ordinary differential equations (ODEs) that describe the binding reactions was created. A system of equations was defined to describe the accumulation and concentration of each of the six species in the model: T cells, antibodies, tumor cells, T cells bound to antibody, tumor cells bound to antibody, and T cell-antibody-tumor cell ternary complexes. A pictorial representation of the model is shown in FIG. 8A.

To validate the model, simulations were run using kinetic parameters taken directly from the literature and then through bounded parameter fitting (Table 3). Using direct literature values, the model was able to recapitulate the general features of the experimental data, including the observed hook effect and a prediction accurate within an

TABLE 4

| Model Error | | |
|---|---|---|
| Simulation | Literature Simulation | Fitted Simulation |
| CAR with Cetuximab | 0.38 | 0.38 |
| CAR with FMC63 | 0.61 | 0.01 |
| CAR with Herceptin | 0.08 | 0.02 |
| CAR with Rituximab | 2.36 | 0.21 |
| synNotch with Cetuximab | 0.73 | 0.02 |
| synNotch with FMC63 | 0.20 | 0.03 |
| synNotch with Herceptin | 1.39 | 0.02 |
| synNotch with Rituximab | 2.51 | 0.02 |

With a validated model, the model was used to predict how different system parameters affect receptor signaling and conducted parameter scans with the model. First, $k_{f1}$, the forward reaction rate of the antibody binding to the T cell receptor, was varied to simulate the effects increasing the on-rate, which can also be experimentally varied by changing the number of BG's conjugated to an antibody. It was found that the model predicted that increasing the number of BG's per antibody leads to greater ternary body formation at higher concentrations of antibody. Once the $k_{f1}$ rate becomes greater than a threshold of $10^{-3}$ $nm^{-1}$ $sec^{-1}$, this effect was expected to plateau. (FIG. 8C). Next, different values were scanned for the antibody to T cell affinity, the parameter maximized by the use of the covalent SNAP to antibody interaction. It was found that stronger affinity was predicted to lead to ternary body formation over a wider range of antibody concentrations and to lead to a higher overall level of ternary body formation. Finally, as target antigen concentration can vary based on the antigen being targeted, and for cancer, expression levels can also significantly vary greatly between patients and on cells within the same patient, a parameter scan varying the level of tumor antigen concentration as performed. It was found that greater antigen concentrations were expected to broaden the effective antibody dosage window for successful ternary complex formation, while lower antigen levels were predicted to require a higher amount of antibody to induce signaling, and were predicted to be more susceptible to inhibition by the hook effect.

b) Discussion

The switchable adaptor SNAP-synNotch system further increases the versatility of the synNotch receptor framework leading to post-translational control of receptor signaling by co-administered antibody dose, as well as the ability to target multiple antigens using a single genetically-encoded receptor. While other adaptor CARs have been described, this is, to the knowledge, the first adaptor synNotch system. The unsuccessful initial attempts to create an adaptor synNotch system using a non-covalent interaction (between mSA2 and biotin) indicate that a very high affinity interaction (ideally covalent) between the synNoch receptor and the tag are required for the adaptor system to function; presumably since the signaling mechanism for Notch is based on an actual pulling force.

With the covalent bond generated by the self-labeling enzyme, the SNAP-CAR has several beneficial characteristics over other adaptor CAR technologies. The results supported by the modeling analysis, herein indicate that the affinity of the interaction between the CAR and the adaptor molecule is a key parameter for productive receptor signaling. The covalent bond produced by the SNAP enzyme and the benzylguanine moiety provides the tightest theoretical bond-a covalent bond- and thus maximizes this critical parameter. While many antibodies will be functional with a non-covalent, lower-affinity adaptor CAR, the model predicts that covalent bond formation can enable use of antibodies that otherwise have a binding affinity to the target antigen that is too low to elicit an effect. Furthermore, the SNAP enzyme reacting to the bio-orthogonal benzylguanine grants the CAR exquisite specificity, and, being an enzyme of human origin, the SNAP protein is likely to be well-tolerated in a human host. This characteristic satisfies a key requirement for the persistence of the adoptively transferred therapeutic cells and minimizes the possibility of toxicities resulting from their immune rejection.

The ability to create functional CARs by preloading the SNAP receptor, followed by removal of excess BG-antibody, provides unique opportunities to test candidate antigen binding regions as components of traditional CARs. Compared to adaptor CARs binding to antigen through a transient interaction, the covalently assembled receptor will more closely resemble that of a traditional CAR. That the pre-assembled SNAP-synNotch receptors were not functional and instead require pre-targeting of the cancer cells was surprising. However, this result can be explained by considering the mechanism of signaling, in which the receptor is proteolytically cleaved and thus destroyed following activation, not allowing for multiple signaling events from recycled receptors. This result indicates that multiple bursts of receptor activation from distinct receptors over time are needed to sufficiently trigger synNotch signaling. As the pre-assembled CARs were capable of signaling, pre-loading the SNAP-CAR T cells can be a clinical approach, however, upon T cell activation, the cells would be induced to expand thus diluting out the assembled receptor, requiring supplementation of additional antibody. Both the CAR and Syn-Notch receptors were maximally effective against tumor cells pre-labeled with antibodies indicating that pre-dosing of a patient with tagged antibody prior to T cell infusion is a superior treatment regimen.

Based on the results, additional self-labeling or covalent protein assembly systems can also provide good frameworks for universal adaptor CARs. Such systems include candidates such as: CLIPtag, Halotag, SpyTag, SnoopTag, Isopeptag, Sortase or split inteins.

The molecular model of switchable receptor systems provided key insights into the observed signaling behaviors and yielded predictions on how to optimize receptor function. The model results indicated that the binding strength between the CAR and the adaptor is a critical parameter for signaling and that the SNAP receptors for which this interaction strength is maximized via a covalent bond are expected to be desirable. Furthermore, the model indicated that one way to improve activity is to increase the forward reaction rate of the CAR binding to the adaptor, which can be accomplished by increasing the number of BG molecules per antibody. Lastly the model predicted that using adaptor CARs to target antigens that are expressed at high levels is preferable as these antigens induce receptor signaling at lower antibody concentrations and are less susceptible to the hook effect at higher antibody doses.

SNAP-synNotch and SNAP-CAR T cells provide a powerful new adaptor strategy for fully programmable targeting of engineered cells to multiple antigens using covalent chemistry. These systems have great potential for clinical application and biotechnological utility by providing researchers with the ability to rapidly screen CAR and synNotch antibody candidates and to rewire and activate cellular programs in response to highly specific antibody-antigen interactions.

c) Methods (1) Construction of Lentiviral Expression Vectors.

pHR_PGK_antiCD19_synNotch_Gal4VP64 and pHR_Gal4UAS_tBFP_PGK_mCherry were gifts from Wendell Lim (Addgene plasmid #79125; RRID: Addgene_79125 and Addgene plasmid #79130; RRID: Addgene_79130, respectively). Sequences for all receptor coding regions and response constructs are listed in the sequence descriptions for SEQ ID NOs: 1, 2, 3, 4, 56, 7, 8, and 9 below. To generate pHR-PGK-SNAP-41BBζ, a DNA fragment encoding SNAP-41BBL was codon-optimized, synthesized (Integrated DNA Technologies) and cloned into the pHR-PGK vector backbone using isothermal assembly. To generate pHR-PGK-SNAP-synNotch-Gal4VP64 and pHR-PGK-mSA2-synNotch-Gal4VP64, DNA encoding the SNAP or mSA2 coding region was codon-optimized and synthesized (Integrated DNA Technologies) and cloned in place of the anti-CD19scFv in plasmid pHR-PGK-antiCD19-synNotch-Gal4VP64 (Addgene #79125) using isothermal assembly. To generate pHR-Gal4UAS-IL7-PGK-mCherry, a DNA fragment encoding IL-7 was codon-optimized, synthesized (Integrated DNA Technologies) and cloned in place of TagBFP in the pHR_Gal4UAS_tBFP_PGK_mCherry vector backbone using isothermal assembly. Virus was generated using the above described transfer vectors following methods described herein.

(2) Production of BG-Antibody Conjugates.

Rituximab (Rituxan, Genentech), Cetuximab (Erbitux, Eli Lily), and Herceptin (Traztuzumab, Genentech) and FMC63 (Novus Biologicals) underwent buffer exchange into PBS using 2 mL 7K MWCO Zeba Spin Desalting Columns (ThermoFisher Scientific). The Rituximab Fab fragment was generated using the Fab Preparation Kit (Pierce) following the manufacturer's protocol. Antibodies were then co-incubated with a 20-fold molar excess of BG-GLA-NHS (NEB) for 30 minutes at room temperature, followed by buffer exchange into PBS using 2 mL 7K MWCO Zeba Spin Desalting Columns.

(3) Quantification of BGs on BG-Conjugated Antibodies.

For in vitro conjugation of whole antibodies with SNAPtag, BG-conjugated purified antibodies (0.5 ug) were incubated with recombinant SNAPtag protein (2 ug). The solution was incubated in PBS (10 μL, pH 7.4) containing DTT (1 mM) at 37° C. for two hours. Conjugation solutions were then diluted with Laemmli buffer, boiled for 5 minutes, and analyzed on an 8% SDS-PAGE (120 V, 1.5 h). Gels were visualized using imidazole-SDS-Zn reverse staining. 1 Briefly, gels were stained with a 200 mM imidazole aqueous solution containing 0.1% SDS for 15 minutes with light agitation. The staining solution was decanted and replaced with water. After 30 seconds, the water was decanted and the gel was developed for 45 seconds with a 200 mM ZnSO4 aqueous solution with light agitation. The gel was then rinsed under running water for 10 seconds. Gels were imaged on a ChemiDoc (Bio-Rad) using epi white light on a black background. Relative band intensities were quantified with ImageJ. A correction factor of 1.5 was applied to the average number of BG/antibody to account for the light chain. Light chains were conjugated to SNAPtag in the same manner except 3 μg of antibody was incubated with 6 ug SNAPtag, gels were analyzed on a 10% SDS-PAGE (120 V, 1.2 h) and stained with Coomassie, and a correction factor was not applied.

(4) Cell Line Culture.

Human tumor cell lines Jurkat Clone E6-1 (TIB-152), ZR-75-1 (CRL-1500), K562 (CCL-243), SKOV-3 (HTB-77), and Raji (CCL-86) were obtained from American Type Culture Collection (ATCC) and cultured at 37° C. in RPMI medium supplemented with 1×MEM amino acids solution, 10 mM Sodium Pyruvate, 10% fetal bovine serum (FBS), and Penicillin-Streptomycin (Life Technologies). K562+ EGFRt, K562+CD20, and Jurkat+EGFRt cells that stably express full-length CD20 and the EGFRt gene, were generated by transducing Jurkat cells with the indicated tumor antigen expressing lentivirus and sorting for cells positive for antigen expression. To create the SNAP-CAR stable cell line, Jurkat cells were transduced with SNAP-41BBζ, and underwent fluorescence-activated cell sorting (FACS) for TagBFP expression. and reporter (mCherry+) expression. To generate SNAP-synNotch lines, SNAP-synNotch-Gal4VP64 was co-transduced with either pHR-Gal4UAS-tBFP-PGKmCherry or pHR-Gal4UAS-IL7-PGKmCherry lentivirus, and receptor and response construct positive cells were obtained by FACS for mycTag antibody staining (Cell signaling Technology) and mCherry expression, respectively. HEK293T cells (ATTC, CRL-3216), used for lentivirus production were cultured at 37° C. in DMEM supplemented with 10% FBS, and Penicillin-Streptomycin.

(5) Primary Human T Cell Culture and Transduction.

All primary T cells for experiments were sourced from deidentified human Buffy Coat samples purchased from the Pittsburgh Central Blood Bank fulfilling the basic exempt criteria 45 CFR 46.101(b)(4) in accordance with the University of Pittsburgh IRB guidelines. PBMC were isolated from a Buffy Coat from healthy volunteer donors using Ficoll gradient centrifugation and human T cells were isolated using the Human Pan T cell isolation kit (Miltenyi Biotec). Human T cells were cultured in supplemented RPMI media as described for cell lines above, however, 10% Human AB serum (Gemini Bio Products) was used instead of FBS, and the media was further supplemented with 100 U/ml human IL-2 IS (Miltenyi Biotec), 1 ng/ml IL-15 (Miltenyi Biotec), and 4 mM L-Arginine (Sigma Aldrich). T cells were stimulated and expanded using TransAct Human T cell Activation Reagent (Miltenyi Biotec). For transduction, 48 hours after activation, lentivirus was added to cells at an MOI of 10-50 in the presence of 6 mg/ml of DEAE-dextran (Sigma Aldrich). After 18 hours, cells were washed and resuspended in fresh T cell media containing 100 U/ml IL-2 and 1 ng/ml IL-15. Cells were split to a concentration of 1M/mL and supplemented with fresh IL-2 and IL-15 every 2-3 days. After 10-12 days of stimulation and expansion, transduced cells were evaluated for CAR expression by flow cytometry and evaluated for activity in subsequent functional assays.

(6) Flow Cytometry Staining.

Cells were washed and resuspended in flow cytometry buffer (PBS+2% FBS) and then stained using the indicated antibodies for 30 minutes at 4° C. followed by two washes with flow cytometry buffer. Live cells and singlets were gated based on scatter. To evaluate SNAP-CAR and SNAP-synNotch expression, 1M cells were labeled with SNAP-Surface 647 (NEB) following manufacturer's recommendation (50 μM concentration of SNAP-Surface 647 in complete cell media) for 30 minutes at 37° C. and washed three times in complete culture media. SNAP-synNotch cells were additionally stained with Myc-Tag-FITC antibody (Cell Signaling Technology) to stain the Myc-Tag on the N-terminus of the receptor.

(7) SNAP-synNotch Cell and Target Cell Co-Incubation Assays for Antibody-Mediated Activation.

100,000 SynNotch Jurkat effector cells were co-cultured with 200,000 of the indicated target cells and BG-conjugated antibody for 48 hours. For assays with SNAP-synNotch cells engineered with the pHR_Gal4UAS_tBFP_PGK_mCherry response construct, co-incubated cells were evaluated by flow cytometry, gating for synNotch cells by mCherry positivity, and then quantifying TagBFP fluorescence for this mCherry+ population. For assays with SNAP-synNotch cells engineered with the pHR_Gal4UAS_IL7_PGK_mCherry construct, following 48 hr incubation, co-incubations were spun down and supernatants were collected and analyzed by ELISA for IL-7 following the manufacturer's recommended protocol (Peprotech).

(8) SNAP-CAR T Cell and Target Cell Co-Incubation Assays for Antibody-Mediated Activation.

100,000 SNAP-CAR Jurkat or primary human T cell effector cells were co-incubated with 200,000 of the indicated target cells and antibody concentrations for 24 hours and assayed by flow cytometry for T cell marker gene expression. For primary cell assays, cells were stained with CD69-PE (BD Biosciences), CD62L-FITC (BD Biosciences), and CD107a-APC (BD Biosciences) antibodies and for Jurkat effector assays, cells were stained with CD62L-FITC (BD Biosciences) and CD25-APC (BD Biosciences)

antibodies. For flow cytometry CAR+ cells were analyzed by gating for the TagBFP+ population. Supernatants from primary cell assays were also collected and analyzed for IFNγ by ELISA (BioLegend). All assays were performed in triplicate and average IFNγ production was plotted with standard deviation.

(9) Target Cell Lysis Assay.

The indicated target cells were stained with Cell Trace Yellow following the manufacturer's recommended protocol (ThermoFisher), and 10,000 target cells per well were co-cultured with 50,000 SNAP-CAR T cells (E:T=5:1) in a 96 well V-bottom plate with 1 μg/mL of the indicated BG-conjugated antibody. Plates underwent a quick-spin to collect cells at the bottom of the wells and were then incubated at 37° C. for 24 hours. To identify lysed cells, co-incubated cells were stained with Ghost Dye Red Viability Dye (Tonbo Biosciences) and analyzed by flow cytometry. Target cells were identified by Cell Trace Yellow and lysed target cells were identified by positive Ghost Dye staining. Percent specific cytotoxicity was calculated by the equation: 100*(% experimental lysis–% target-only lysis)/(100–% target-only lysis).

(10) Pre-Labeling Co-Incubation Assays.

Pre-labeling co-incubation activation assays, were carried out as above, except prior to co-incubation for pre-labeled SNAP effector cell assays, SNAP-CAR or SNAP-synNotch Jurkat cells were first labeled with 1 μg/mL of the indicated BG-modified antibody in complete media for 30 minutes at 37° C. and then washed three times in complete media, and for pre-labeled target cell assays, target cells were labeled with 5 μg/mL of the indicated antibody for 30 minutes at 4° C. and washed two times with flow buffer. No additional antibody was added to these co-incubations.

(11) Mathematical Model.

The model for ternary body formation considered the following 8 binding reactions between the tumor cells, T cells, and antibody with six different species: T cell (Tc), antibody (Ab), tumor cell (Tu), T cell bound to antibody (Tc.Ab), tumor cell bound to antibody (Ab.Tu), and a ternary body complex of a T cell bound to antibody and tumor cell (Tc.Ab.Tu) and where rates $k_{fi}$ (i=1 . . . 4) represent the forward kinetic rate constants, and rates $k_{ri}$ represent the reverse kinetic rate constants:

$$Tc + Ab \underset{k_{r1}}{\overset{k_{f1}}{\rightleftharpoons}} Tc.Ab \qquad \text{Reactions 1 and 2}$$

$$Ab + Tu \underset{k_{r2}}{\overset{k_{f2}}{\rightleftharpoons}} Ab.Tu \qquad \text{Reactions 3 and 4}$$

$$Tc.Ab + Tu \underset{k_{r3}}{\overset{k_{f3}}{\rightleftharpoons}} Tc.Ab.Tu \qquad \text{Reactions 5 and 6}$$

$$Tc + Ab.Tu \underset{k_{r4}}{\overset{k_{f4}}{\rightleftharpoons}} Tc.Ab.Tu \qquad \text{Reactions 7 and 8}$$

From reactions 1-8, a system of equations was derived to describe the accumulation of each of the six species in the model. In Equations 1-8 below, are listed the forward and backward components of the eight reactions expressing the change in concentration of each species:

$rxn_1 = k_{f1}*[Tc]*[Ab]$ (binding of T cell to antibody) [Eq 1]

$rxn_2 = k_{r1} \cdot [Tc.Ab]$ (dissociation of T cell-antibody) [Eq 2]

$rxn_3 = k_{f2} \cdot [Ab]*[Tu]$ (binding of tumor cell to antibody) [Eq 3]

$rxn_4 = k_{r2} \cdot [Ab.Tu]$ (dissociation of tumor cell-antibody) [Eq 4]

$rxn_5 = k_{f3} \cdot [Tc.Ab]*[Tu]$ (binding of T cell-antibody to tumor cell) [Eq 5]

$rxn_6 = k_{r3} \cdot [Tc.Ab.Tu]$ (dissociation of tumor cell from ternary body) [Eq 6]

$rxn_7 = k_{f4} \cdot [Tc] \cdot [Ab.Tu]$ (binding of T cell to tumor cell-antibody) [Eq 7]

$rxn_8 = k_{r4}*[Tc.Ab.Tu]$ (dissociation of T cell from ternary body) [Eq 8]

The equations 9-14 below were used to compute the change in concentration of each species.

$$\frac{d[Tc]}{dt} = -rxn_1 + rxn_2 - rxn_7 + rxn_8 \qquad \text{[Eq 9]}$$

(change in free T Cell receptor)

$$\frac{d[Ab]}{dt} = -rxn_1 + rxn_2 - rxn_3 + rxn_4 \qquad \text{[Eq 10]}$$

(change in free antibody)

$$\frac{d[Tu]}{dt} = -rxn_3 + rxn_4 - rxn_5 + rxn_6 \qquad \text{[Eq 11]}$$

(change in free Tumor cell receptor)

$$\frac{d[Tc.Ab]}{dt} = +rxn_1 - rxn_2 - rxn_5 + rxn_6 \qquad \text{[Eq 12]}$$

(change in T cell – Antibody)

$$\frac{d[Ab.Tu]}{dt} = +rxn_3 - rxn_4 - rxn_7 + rxn_8 \qquad \text{[Eq 13]}$$

(change in Tumor Cell – Antibody)

$$\frac{d[Tc.Ab.Tu]}{dt} = +rxn_5 - rxn_6 + rxn_7 - rxn_8 \qquad \text{[Eq 14]}$$

(change in Ternary Body)

The ODE model was created under the assumption was made that the system components were well-mixed. Variables used in the ODEs were taken from the experimental design and literature values of kinetic binding and dissociation rates as summarized in Supplementary Table S2[34-37]. The ODE model was written in Python and solved using SciPy. To examine the concentration of each species with time, the system of ODEs was solved using the initial conditions and experimental setup values through a kinetic simulation (Supplementary Fig. S5). To generate equilibrium simulations (Supplementary Fig. S6), kinetic simulations were run for variety of antibody concentrations ($10^{-4}$ ug/mL-$10^1$ ug/mL) and total ternary body formation from the equilibrium state of each kinetic simulation was plotted. To fit the model, the sum of squared error (SSE) was calculated between the experimental data and the simulation results. For the experimental data the TagBFP MFI for synNotch (FIG. 5D) and CD25 MFI were used for the read-out of SNAP-CAR activation (FIG. 6D). As the experimental data was only collected at specific points of antibody concentration, only the matching points in the simulations were used. Using SciPy, SSE was minimized to optimize the kinetic parameters and better fit the model to the experimental data for each antibody pair (FIG. 8B). During parameter estimation, the literature values were used as initial estimates and bounded within one order of magnitude. Parameter scans of $k_{f1}$, $K_{d2}$, and the number of tumor antigens were conducted as above for equilibrium simulations using 900 simulations over the bounds for each parameter. Ternary body formation was normalized to the maximal concentration across all simulations.

(12) Statistical Methods.

The number of replicates, mean value, and error are described in the respective figure legends and/or methods. Error bars are shown for all data points with replicates as a measure of variation within a group.

E. References

Andersen, P. S. et al. Quantifying the energetics of cooperativity in a ternary protein complex. *Biochemistry* 41, 5177-5184, doi:10.1021/bi0200209 (2002).

Cho, J. H., Collins, J. J. & Wong, W. W. Universal Chimeric Antigen Receptors for Multiplexed and Logical Control of T Cell Responses. *Cell* 173, 1426-1438 e1411, doi: 10.1016/j.cell.2018.03.038 (2018).

Chudasama, V. L. et al. Simulations of site-specific target-mediated pharmacokinetic models for guiding the development of bispecific antibodies. *J Pharmacokinet Pharmacodyn* 42, 1-18, doi:10.1007/s10928-014-9401-1 (2015).

De Lean, A., Stadel, J. M. & Lefkowitz, R. J. A ternary complex model explains the agonist-specific binding properties of the adenylate cyclase-coupled beta-adrenergic receptor. *J Biol Chem* 255, 7108-7117 (1980).

Doldan-Martelli, V., Guantes, R. & Miguez, D. G. A mathematical model for the rational design of chimeric ligands in selective drug therapies. *CPT Pharmacometrics Syst Pharmacol* 2, e26, doi:10.1038/psp.2013.2 (2013).

Douglass, E. F., Jr., Miller, C. J., Sparer, G., Shapiro, H. & Spiegel, D. A. A comprehensive mathematical model for three-body binding equilibria. *J Am Chem Soc* 135, 6092-6099, doi:10.1021/ja311795d (2013).

Eric Jones, T. O., Pearu Peterson. *SciPy: Open Source Scientific Tools for Python* (2001).

Esensten, J. H., Bluestone, J. A. & Lim, W. A. Engineering Therapeutic T Cells: From Synthetic Biology to Clinical Trials. *Annu Rev Pathol* 12, 305-330, doi:10.1146/annurev-pathol-052016-100304 (2017).

Gautier, A. et al. An engineered protein tag for multiprotein labeling in living cells. *Chem Biol* 15, 128-136, doi: 10.1016/j.chembiol.2008.01.007 (2008).

Gross, G., Waks, T. & Eshhar, Z. Expression of immunoglobulin-T-cell receptor chimeric molecules as functional receptors with antibody-type specificity. *Proc Natl Acad Sci USA* 86, 10024-10028, doi:10.1073/pnas.86.24.10024 (1989).

June, C. H. & Sadelain, M. Chimeric Antigen Receptor Therapy. *N Engl J Med* 379, 64-73, doi:10.1056/NEJMra1706169 (2018).

Keppler, A. et al. A general method for the covalent labeling of fusion proteins with small molecules in vivo. *Nat Biotechnol* 21, 86-89, doi:10.1038/nbt765 (2003).

Kershaw, M. H. et al. A phase I study on adoptive immunotherapy using gene-modified T cells for ovarian cancer. *Clinical cancer research: an official journal of the American Association for Cancer Research* 12, 6106-6115, doi:10.1158/1078-0432.CCR-06-1183 (2006).

Kudo, K. et al. T lymphocytes expressing a CD16 signaling receptor exert antibody-dependent cancer cell killing. *Cancer research* 74, 93-103, doi:10.1158/0008-5472.CAN-13-1365 (2014).

Lamers, C. H. et al. Treatment of metastatic renal cell carcinoma with autologous T-lymphocytes genetically retargeted against carbonic anhydrase IX: first clinical experience. *J Clin Oncol* 24, e20-22, doi:10.1200/JCO.2006.05.9964 (2006).

Lim, K. H., Huang, H., Pralle, A. & Park, S. Stable, high-affinity streptavidin monomer for protein labeling and monovalent biotin detection. *Biotechnol Bioeng* 110, 57-67, doi:10.1002/bit.24605 (2013).

Lohmueller, J. & Finn, O. J. Current modalities in cancer immunotherapy: Immunomodulatory antibodies, CARs and vaccines. *Pharmacol Ther* 178, 31-47, doi:10.1016/j.pharmthera.2017.03.008 (2017).

Lohmueller, J. J. et al. Antibodies elicited by the first non-viral prophylactic cancer vaccine show tumor-specificity and immunotherapeutic potential. *Sci Rep* 6, 31740, doi:10.1038/srep31740 (2016).

Lohmueller, J. J., Ham, J. D., Kvorjak, M. & Finn, O. J. mSA2 affinity-enhanced biotin-binding CAR T cells for universal tumor targeting. *Oncoimmunology* 7, e1368604, doi:10.1080/2162402X.2017.1368604 (2017).

Los, G. V. et al. HaloTag: a novel protein labeling technology for cell imaging and protein analysis. *ACS Chem Biol* 3, 373-382, doi:10.1021/cb800025k (2008).

Lu, C. & Wang, Z. X. Quantitative Analysis of Ligand Induced Heterodimerization of Two Distinct Receptors. *Anal Chem* 89, 6926-6930, doi:10.1021/acs.analchem.7b01274 (2017).

Ma, J. S. et al. Versatile strategy for controlling the specificity and activity of engineered T cells. *Proc Natl Acad Sci USA* 113, E450-458, doi:10.1073/pnas. 1524193113 (2016).

Mackall, C. L., Fry, T. J. & Gress, R. E. Harnessing the biology of IL-7 for therapeutic application. *Nat Rev Immunol* 11, 330-342, doi:10.1038/nri2970 (2011).

Maloney, D. G. et al. IDEC-C2B8 (Rituximab) anti-CD20 monoclonal antibody therapy in patients with relapsed low-grade non-Hodgkin's lymphoma. *Blood* 90, 2188-2195 (1997).

Maude, S. L. et al. Chimeric antigen receptor T cells for sustained remissions in leukemia. *N Engl J Med* 371, 1507-1517, doi:10.1056/NEJMoa1407222 (2014).

Maus, M. V. et al. T cells expressing chimeric antigen receptors can cause anaphylaxis in humans. *Cancer Immunol Res* 1, 26-31, doi:10.1158/2326-6066.CIR-13-0006 (2013).

Morsut, L. et al. Engineering Customized Cell Sensing and Response Behaviors Using Synthetic Notch Receptors. *Cell* 164, 780-791, doi:10.1016/j.cell.2016.01.012 (2016).

Otsuki, J., Narita, T., Tsutsumida, K., Takatsuki, M. & Kaneko, M. Modular approach toward supramolecular functional assemblies: characterization of Donor-spacer-acceptor ternary complexes. *J Phys Chem A* 109, 6128-6134, doi:10.1021/jp051012f (2005).

Porter, D. L., Levine, B. L., Kalos, M., Bagg, A. & June, C. H. Chimeric antigen receptor-modified T cells in chronic lymphoid leukemia. *N Engl J Med* 365, 725-733, doi: 10.1056/NEJMoa1103849 (2011).

Rodgers, D. T. et al. Switch-mediated activation and retargeting of CAR-T cells for B-cell malignancies. *Proc Natl Acad Sci USA* 113, E459-468, doi:10.1073/pnas. 1524155113 (2016).

Roybal, K. T. et al. Engineering T Cells with Customized Therapeutic Response Programs Using Synthetic Notch Receptors. *Cell* 167, 419-432 e416, doi:10.1016/j.cell.2016.09.011 (2016).

Roybal, K. T. et al. Precision Tumor Recognition by T Cells With Combinatorial Antigen-Sensing Circuits. *Cell* 164, 770-779, doi:10.1016/j.cell.2016.01.011 (2016).

Sadelain, M., Brentjens, R. & Riviere, I. The basic principles of chimeric antigen receptor design. *Cancer Discov* 3, 388-398, doi:10.1158/2159-8290.CD-12-0548 (2013).

Slamon, D. J. et al. Use of chemotherapy plus a monoclonal antibody against HER2 for metastatic breast cancer that overexpresses HER2. *N Engl J Med* 344, 783-792, doi: 10.1056/NEJM200103153441101 (2001).

Sun, X. et al. Development of SNAP-tag fluorogenic probes for wash-free fluorescence imaging. *Chembiochem* 12, 2217-2226, doi:10.1002/cbic.201100173 (2011).

Tamada, K. et al. Redirecting gene-modified T cells toward various cancer types using tagged antibodies. *Clinical cancer research: an official journal of the American Association for Cancer Research* 18, 6436-6445, doi: 10.1158/1078-0432.CCR-12-1449 (2012).

Toda, S., Blauch, L. R., Tang, S. K. Y., Morsut, L. & Lim, W. A. Programming self-organizing multicellular structures with synthetic cell-cell signaling. *Science* 361, 156-162, doi:10.1126/science.aat0271 (2018).

Urbanska, K. et al. A universal strategy for adoptive immunotherapy of cancer through use of a novel T-cell antigen receptor. *Cancer research* 72, 1844-1852, doi:10.1158/0008-5472.CAN-11-3890 (2012).

van Steeg, T. J., Bergmann, K. R., Dimasi, N., Sachsenmeier, K. F. & Agoram, B. The application of mathematical modelling to the design of bispecific monoclonal antibodies. *MAbs* 8, 585-592, doi:10.1080/19420862.2016.1141160 (2016).

Veggiani, G. et al. Programmable polyproteams built using twin peptide superglues. *Proc Natl Acad Sci USA* 113, 1202-1207, doi:10.1073/pnas. 1519214113 (2016).

Wang, J., Yu, Y. & Xia, J. Short peptide tag for covalent protein labeling based on coiled coils. *Bioconjug Chem* 25, 178-187, doi:10.1021/bc400498p (2014).

Wang, X. & Ha, T. Defining single molecular forces required to activate integrin and notch signaling. *Science* 340, 991-994, doi:10.1126/science.1231041 (2013).

Wu, H., Hu, Z. & Liu, X. Q. Protein trans-splicing by a split intein encoded in a split DnaE gene of *Synechocystis* sp. PCC6803. *Proc Natl Acad Sci USA* 95, 9226-9231, doi: 10.1073/pnas.95.16.9226 (1998).

Wu, X., Fan, Z., Masui, H., Rosen, N. & Mendelsohn, J. Apoptosis induced by an anti-epidermal growth factor receptor monoclonal antibody in a human colorectal carcinoma cell line and its delay by insulin. *J Clin Invest* 95, 1897-1905, doi:10.1172/JCI117871 (1995).

Yang, G. et al. Genetic targeting of chemical indicators in vivo. *Nat Methods* 12, 137-139, doi:10.1038/nmeth.3207 (2015).

Zola, H. et al. Preparation and characterization of a chimeric CD19 monoclonal antibody. *Immunol Cell Biol* 69 (Pt 6), 411-422, doi:10.1038/icb.1991.58 (1991).

SEQ ID NO: 1 SNAP-41BBζ CAR DNA sequence

```
ATGGAGACAGACACACTCCTGCTATGGGTGCTGCTGCTCTGGGTTCCAGGTTCCACA

GGTATGGACAAAGATTGCGAGATGAAGAGAACCACCCTGGATAGCCCTCTCGGCAA

GCTCGAACTTTCTGGTTGTGAACAGGGTTTGCACAGGATCATCTTCCTGGGAAAGGG

AACCTCAGCCGCAGATGCGGTTGAAGTGCCAGCTCCGGCTGCAGTGCTTGGTGGAC

CCGAGCCTCTTATGCAAGCAACGGCATGGCTTAATGCTTATTTTCACCAGCCTGAGG

CCATTGAAGAGTTTCCAGTTCCTGCATTGCATCACCCCGTTTTTCAGCAGGAATCCTT

CACTAGACAAGTGCTTTGGAAGCTCTTGAAAGTGGTTAAATTTGGGGAAGTCATCTC

ATACAGCCACCTTGCTGCCCTTGCAGGCAATCCTGCGGCCACGGCTGCAGTGAAAA

CTGCACTTAGCGGAAATCCAGTCCCCATCTTGATACCGTGTCACAGGGTAGTACAGG

GCGACCTGGACGTCGGCGGTTACGAGGGCGGTTTGGCCGTTAAGGAATGGTTGCTG

GCGCATGAGGGTCACCGGCTGGGAAAACCAGGTCTTGGTGGAGGAAGTGGAGGAT

CTACCACTACTCCGGCACCGCGCCCCCCAACTCCTGCACCGACGATAGCTTCACAAC

CGCTTTCATTGCGGCCCGAAGCATGTCGGCCAGCCGCCGGAGGCGCTGTGCATACA

AGAGGGCTGGATTTTGCATGTGATATATATATTTGGGCGCCCCTTGCTGGCACTTGC

GGCGTTCTTCTTCTTAGCCTCGTTATTACGCTCTACTGTAAGCGAGGTAGGAAAAAA

TTGCTGTATATCTTTAAACAGCCTTTTATGAGACCCGTGCAAACGACTCAAGAGGAA

GACGGGTGTAGCTGTAGATTTCCTGAAGAGGAAGAGGGGGGGTGCGAACTGCGGGT

GAAGTTCAGCAGAAGCGCCGACGCCCCTGCCTACCAGCAGGGCCAGAATCAGCTGT

ACAACGAGCTGAACCTGGGCAGAAGGGAAGAGTACGACGTCCTGGATAAGCGGAG

AGGCCGGGACCCTGAGATGGGCGGCAAGCCTCGGCGGAAGAACCCCCAGGAAGGC

CTGTATAACGAACTGCAGAAAGACAAGATGGCCGAGGCCTACAGCGAGATCGGCAT

GAAGGGCGAGCGGAGGCGGGGCAAGGGCCACGACGGCCTGTATCAGGGCCTGTCC
```

-continued
ACCGCCACCAAGGATACCTACGACGCCCTGCACATGCAGGCCCTGCCCCCAAGGCT

CGAGGGCGGCGGAGAGGGCAGAGGAAGTCTTCTAACATGCGGTGACGTGGAGGAG

AATCCCGGCCCTCGCATGAGCGAGCTGATTAAGGAGAACATGCACATGAAGCTGTA

CATGGAGGGCACCGTGGACAACCATCACTTCAAGTGCACATCCGAGGGCGAAGGCA

AGCCCTACGAGGGCACCCAGACCATGAGAATCAAGGTGGTCGAGGGCGGCCCTCTC

CCCTTCGCCTTCGACATCCTGGCTACTAGCTTCCTCTACGGCAGCAAGACCTTCATC

AACCACACCCAGGGCATCCCCGACTTCTTCAAGCAGTCCTTCCCTGAGGGCTTCACA

TGGGAGAGAGTCACCACATACGAAGACGGGGGCGTGCTGACCGCTACCCAGGACA

CCAGCCTCCAGGACGGCTGCCTCATCTACAACGTCAAGATCAGAGGGGTGAACTTC

ACATCCAACGGCCCTGTGATGCAGAAGAAAACACTCGGCTGGGAGGCCTTCACCGA

GACGCTGTACCCCGCTGACGGCGGCCTGGAAGGCAGAAACGACATGGCCCTGAAGC

TCGTGGGCGGGAGCCATCTGATCGCAAACATCAAGACCACATATAGATCCAAGAAA

CCCGCTAAGAACCTCAAGATGCCTGGCGTCTACTATGTGGACTACAGACTGGAAAG

AATCAAGGAGGCCAACAACGAAACATACGTCGAGCAGCACGAGGTGGCAGTGGCC

AGATACTGCGACCTCCCTAGCAAACTGGGGCACAAGCTTAATTAA
Murine kappa leader sequence 60 nucleotides, residues 1-60
SNAPf 564 nucleotides, residues 61-624
CD8αHinge, Transinembrane 207 nucleotides, residues 625-831
4-1BBcyto 126 nucleotides, residues 832-957
CD3zeta 336 nucleotides, residues 958-1293
T2A-Ta2BFP 774 nucleotides, residues 1294-2067

SEQ ID NO: 2 SNAP-synNotch-Gal4VP64 DNA sequence
ATGGCGCTCCCTGTCACCGCACTGCTTCTTCCGCTGGCACTGCTGCTGCACGCTGCA

CGGCCTGAGCAAAAACTTATCTCTGAAGAGGACCTCATGGACAAAGATTGCGAGAT

GAAGAGAACCACCCTGGATAGCCCTCTCGGCAAGCTCGAACTTTCTGGTTGTGAAC

AGGGTTTGCACAGGATCATCTTCCTGGGAAAGGGAACCTCAGCCGCAGATGCGGTT

GAAGTGCCAGCTCCGGCTGCAGTGCTTGGTGGACCCGAGCCTCTTATGCAAGCAAC

GGCATGGCTTAATGCTTATTTTCACCAGCCTGAGGCCATTGAAGAGTTTCCAGTTCC

TGCATTGCATCACCCCGTTTTTCAGCAGGAATCCTTCACTAGACAAGTGCTTTGGAA

GCTCTTGAAAGTGGTTAAATTTGGGGAAGTCATCTCATACAGCCACCTTGCTGCCCT

TGCAGGCAATCCTGCGGCCACGGCTGCAGTGAAAACTGCACTTAGCGGAAATCCAG

TCCCCATCTTGATACCGTGTCACAGGGTAGTACAGGGCGACCTGGACGTCGGCGGTT

ACGAGGGCGGTTTGGCCGTTAAGGAATGGTTGCTGGCGCATGAGGGTCACCGGCTG

GGAAAACCAGGTCTTGGTGGAGGAAGTGGAGGATCTATCCTGGACTACAGCTTCAC

AGGTGGCGCTGGGCGCGACATFCCCCCACCGCAGATTGAGGAGGCCTGTGAGCTGC

CTGAGTGCCAGGTGGATGCAGGCAATAAGGTCTGCAACCTGCAGTGTAATAATCAC

GCATGTGGCTGGGATGGTGGCGACTGCTCCCTCAACTTCAATGACCCCTGGAAGAA

CTGCACGCAGTCTCTACAGTGCTGGAAGTATTTTAGCGACGGCCACTGTGACAGCCA

GTGCAACTCGGCCGGCTGCCTCTTTGATGGCTTCGACTGCCAGCTCACCGAGGGACA

GTGCAACCCCCTGTATGACCAGTACTGCAAGGACCACTTCAGTGATGGCCACTGCG

ACCAGGGCTGTAACAGTGCCGAATGTGAGTGGGATGGCCTAGACTGTGCTGAGCAT

GTACCCGAGCGGCTGGCAGCCGGCACCCTGGTGCTGGTGGTGCTGCTTCCACCCGA

CCAGCTACGGAACAACTCCTTCCACTTTCTGCGGGAGCTCAGCCACGTGCTGCACAC

CAACGTGGTCTTCAAGCGTGATGCGCAAGGCCAGCAGATGATCTTCCCGTACTATG

GCCACGAGGAAGAGCTGCGCAAGCACCCAATCAAGCGCTCTACAGTGGGTTGGGCC

ACCTCTTCACTGCTTCCTGGTACCAGTGGTGGGCGCCAGCGCAGGGAGCTGGACCCC

ATGGACATCCGTGGCTCCATTGTCTACCTGGAGATCGACAACCGGCAATGTGTGCA

GTCATCCTCGCAGTGCTTCCAGAGTGCCACCGATGTGGCTGCCTTCCTAGGTGCTCT

TGCGTCACTTGGCAGCCTCAATATTCCTTACAAGATMAGGCCGTGAAGAGTGAGCC

GGTGGAGCCTCCGCTGCCCTCGCAGCTGCACCTCATGTACGTGGCAGCGGCCGCCTT

CGTGCTCCTGTTCTTTGTGGGCTGTGGGGTGCTGCTGTCCCGCAAGCGCCGGCGGAT

GAAGCTGCTGAGCAGCATCGAGCAGGCCTGTGACATCTGCCGGCTGAAGAAACTGA

AGTGCAGCAAAGAAAAGCCCAAGTGCGCCAAGTGCCTGAAGAACAACTGGGAGTG

CCGGTACAGCCCCAAGACCAAGAGAAGCCCCCTGACCAGAGCCCACCTGACCGAGG

TGGAAAGCCGGCTGGAAAGACTGGAACAGCTGTTTCTGCTGATCTTCCCACGCGAG

GACCTGGACATGATCCTGAAGATGGACAGCCTGCAGGACATCAAGGCCCTGCTGAC

CGGCCTGTTCGTGCAGGACAACGTGAACAAGGACGCCGTGACCGACAGACTGGCCA

GCGTGGAAACCGACATGCCCCTGACCCTGCGGCAGCACAGAATCAGCGCCACCAGC

AGCAGCGAGGAAAGCAGCAACAAGGGCCAGCGGCAGCTGACAGTGTCTGCTGCTG

CAGGCGGAAGCGGAGGCTCTGGCGGATCTGATGCCCTGGACGACTTCGACCTGGAT

ATGCTGGGCAGCGACGCCCTGGATGATTTTGATCTGGACATGCTGGGATCTGACGCT

CTGGACGATTTCGATCTCGACATGTTGGGATCAGATGCACTGGATGACTTTGACCTG

GACATGCTCGGATCATGA
Notch leader sequence 63 nucleotides, residues 1-63
mycTag 30 nucleotides, residues 64-93
SNAPf 564 nucleotides, residues 94-657
Notch Core 978 nucleotides, residues 658-1635
Gal4-VP64 636 nucleotides, residues 1636-2271

SEQ ID NO: 3 SNAPf nucleic acid sequence
ATGGACAAAGATTGCGAGATGAAGAGAACCACCCTGGATAGCCCTCTCGGCAAGCT

CGAACTTTCTGGTTGTGAACAGGGTTTGCACAGGATCATCTTCCTGGGAAAGGGAA

CCTCAGCCGCAGATGCGGTTGAAGTGCCAGCTCCGGCTGCAGTGCTTGGTGGACCC

GAGCCTCTTATGCAAGCAACGGCATGGCTTAATGCTTATTTTCACCAGCCTGAGGCC

ATTGAAGAGTTTCCAGTTCCTGCATTGCATCACCCCGTTTTTCAGCAGGAATCCTTC

ACTAGACAAGTGCTTTGGAAGCTCTTGAAAGTGGTTAAATTTGGGGAAGTCATCTCA

TACAGCCACCTTGCTGCCCTTGCAGGCAATCCTGCGGCCACGGCTGCAGTGAAAACT

GCACTTAGCGGAAATCCAGTCCCCATCTTGATACCGTGTCACAGGGTAGTACAGGG

CGACCTGGACGTCGGCGGTTACGAGGGCGGTTTGGCCGTTAAGGAATGGTTGCTGG

CGCATGAGGGTCACCGGCTGGGAAAACCAGGTCTTGGTGGAGGAAGTGGAGGATCT

SEQ ID NO: 4 CD3zeta
CGGGTGAAGTTCAGCAGAAGCGCCGACGCCCCTGCCTACCAGCAGGGCCAGAATCA

GCTGTACAACGAGCTGAACCTGGGCAGAAGGGAAGAGTACGACGTCCTGGATAAG

CGGAGAGGCCGGGACCCTGAGATGGGCGGCAAGCCTCGGCGGAAGAACCCCCAGG

AAGGCCTGTATAACGAACTGCAGAAAGACAAGATGGCCGAGGCCTACAGCGAGAT

CGGCATGAAGGGCGAGCGGAGGCGGGGCAAGGGCCACGACGGCCTGTATCAGGGC

CTGTCCACCGCCACCAAGGATACCTACGACGCCCTGCACATGCAGGCCCTGCCCCC

AAGG

-continued

SEQ ID NO: 5 Notch core
ATCCTGGACTACAGCTTCACAGGTGGCGCTGGGCGCGACATTCCCCCACCGCAGATT

GAGGAGGCCTGTGAGCTGCCTGAGTGCCAGGTGGATGCAGGCAATAAGGTCTGCAA

CCTGCAGTGTAATAATCACGCATGTGGCTGGGATGGTGGCGACTGCTCCCTCAACTT

CAATGACCCCTGGAAGAACTGCACGCAGTCTCTACAGTGCTGGAAGTATTTTAGCG

ACGGCCACTGTGACAGCCAGTGCAACTCGGCCGGCTGCCTCTTTGATGGCTTCGACT

GCCAGCTCACCGAGGGACAGTGCAACCCCCTGTATGACCAGTACTGCAAGGACCAC

TTCAGTGATGGCCACTGCGACCAGGGCTGTAACAGTGCCGAATGTGAGTGGGATGG

CCTAGACTGTGCTGAGCATGTACCCGAGCGGCTGGCAGCCGGCACCCTGGTGCTGG

TGGTGCTGCTTCCACCCGACCAGCTACGGAACAACTCCTTCCACTTTCTGCGGGAGC

TCAGCCACGTGCTGCACACCAACGTGGTCTTCAAGCGTGATGCGCAAGGCCAGCAG

ATGATCTTCCCGTACTATGGCCACGAGGAAGAGCTGCGCAAGCACCCAATCAAGCG

CTCTACAGTGGGTTGGGCCACCTCTTCACTGCTTCCTGGTACCAGTGGTGGGCGCCA

GCGCAGGGAGCTGGACCCCATGGACATCCGTGGCTCCATTGTCTACCTGGAGATCG

ACAACCGGCAATGTGTGCAGTCATCCTCGCAGTGCTTCCAGAGTGCCACCGATGTG

GCTGCCTTCCTAGGTGCTCTTGCGTCACTTGGCAGCCTCAATATTCCTTACAAGATTG

AGGCCGTGAAGAGTGAGCCGGTGGAGCCTCCGCTGCCCTCGCAGCTGCACCTCATG

TACGTGGCAGCGGCCGCCTTCGTGCTCCTGTTCTTTGTGGGCTGTGGGGTGCTGCTG

TCCCGCAAGCGCCGGCGG

SEQ ID NO: 6 SNAP-41BBζ-T2A-TagBFP (entire coding region
inserted into pHR-PGK vector)
GGAGCAAGGCAGGTGGACAGTGGATCATGGAGACAGACACACTCCTGCTATGGGTG

CTGCTGCTCTGGGTTCCAGGTTCCACAGGTATGGACAAAGATTGCGAGATGAAGAG

AACCACCCTGGATAGCCCTCTCGGCAAGCTCGAACTTTCTGGTTGTGAACAGGGTTT

GCACAGGATCATCTTCCTGGGAAAGGGAACCTCAGCCGCAGATGCGGTTGAAGTGC

CAGCTCCGGCTGCAGTGCTTGGTGGACCCGAGCCTCTTATGCAAGCAACGGCATGG

CTTAATGCTTATTTTCACCAGCCTGAGGCCATTGAAGAGTTTCCAGTTCCTGCATTGC

ATCACCCCGTTTTTCAGCAGGAATCCTTCACTAGACAAGTGCTTTGGAAGCTCTTGA

AAGTGGTTAAATTTGGGGAAGTCATCTCATACAGCCACCTTGCTGCCCTTGCAGGCA

ATCCTGCGGCCACGGCTGCAGTGAAAACTGCACTTAGCGGAAATCCAGTCCCCATC

TTGATACCGTGTCACAGGGTAGTACAGGGCGACCTGGACGTCGGCGGTTACGAGGG

CGGTTTGGCCGTTAAGGAATGGTTGCTGGCGCATGAGGGTCACCGGCTGGGAAAAC

CAGGTCTTGGTGGAGGAAGTGGAGGATCTACCACTACTCCGGCACCGCGCCCCCA

ACTCCTGCACCGACGATAGCTTCACAACCGCTTTCATTGCGGCCCGAAGCATGTCGG

CCAGCCGCCGGAGGCGCTGTGCATACAAGAGGGCTGGATTTTGCATGTGATATATA

TATTTGGGCGCCCCTTGCTGGCACTTGCGGCGTTCTTCTTCTTAGCCTCGTTATTACG

CTCTACTGTAAGCGAGGTAGGAAAAAATTGCTGTATATCTTTAAACAGCCTTTTATG

AGACCCGTGCAAACGACTCAAGAGGAAGACGGGTGTAGCTGTAGATTTCCTGAAGA

GGAAGAGGGGGGGTGCGAACTGCGGGTGAAGTTCAGCAGAAGCGCCGACGCCCCT

GCCTACCAGCAGGGCCAGAATCAGCTGTACAACGAGCTGAACCTGGGCAGAAGGG

AAGAGTACGACGTCCTGGATAAGCGGAGAGGCCGGGACCCTGAGATGGGCGGCAA

GCCTCGGCGGAAGAACCCCCAGGAAGGCCTGTATAACGAACTGCAGAAAGACAAG

ATGGCCGAGGCCTACAGCGAGATCGGCATGAAGGGCGAGCGGAGGCGGGGCAAGG

GCCACGACGGCCTGTATCAGGGCCTGTCCACCGCCACCAAGGATACCTACGACGCC

CTGCACATGCAGGCCCTGCCCCCAAGGCTCGAGGGCGGCGGAGAGGGCAGAGGAA

GTCTTCTAACATGCGGTGACGTGGAGGAGAATCCCGGCCCTCGCATGAGCGAGCTG

ATTAAGGAGAACATGCACATGAAGCTGTACATGGAGGGCACCGTGGACAACCATCA

CTTCAAGTGCACATCCGAGGGCGAAGGCAAGCCCTACGAGGGCACCCAGACCATGA

GAATCAAGGTGGTCGAGGGCGGCCCTCTCCCCTTCGCCTTCGACATCCTGGCTACTA

GCTTCCTCTACGGCAGCAAGACCTTCATCAACCACACCCAGGGCATCCCCGACTTCT

TCAAGCAGTCCTTCCCTGAGGGCTTCACATGGGAGAGAGTCACCACATACGAAGAC

GGGGGCGTGCTGACCGCTACCCAGGACACCAGCCTCCAGGACGGCTGCCTCATCTA

CAACGTCAAGATCAGAGGGGTGAACTTCACATCCAACGGCCCTGTGATGCAGAAGA

AAACACTCGGCTGGGAGGCCTTCACCGAGACGCTGTACCCCGCTGACGGCGGCCTG

GAAGGCAGAAACGACATGGCCCTGAAGCTCGTGGGCGGGAGCCATCTGATCGCAA

ACATCAAGACCACATATAGATCCAAGAAACCCGCTAAGAACCTCAAGATGCCTGGC

GTCTACTATGTGGACTACAGACTGGAAAGAATCAAGGAGGCCAACAACGAAACATA

CGTCGAGCAGCACGAGGTGGCAGTGGCCAGATACTGCGACCTCCCTAGCAAACTGG

GGCACAAGCTTAATTAAGATCCTTGACTTGCGGCCGCAACTCCCAC
5' region of pHR-PGK acceptor vector, residues 1-26
Leader sequence and Kozak sequence, residues 27-86
SNAPtag, residues 87-650
CD8α-hinge, TM, residues 651-857
4-1BBcyto. residues 858-983
CD3ζcyto, residues 984-1319
T2A, residues 1320-1391
TagBFP, residues 1392-2093
3' region of pHR-PGK acceptor vector, residues 2094-2122

SEQ ID NO: 7: pHR-PGK-SNAP-synNotch-Gal4-VP64 (insert for
pHR-PGK-[]-synNotch-Gal4-VP64 backbone)
GAGCAAAAACTTATCTCTGAAGAGGACCTCATGGACAAAGATTGCGAGATGAAGAG

AACCACCCTGGATAGCCCTCTCGGCAAGCTCGAACTTTCTGGTTGTGAACAGGGTTT

GCACAGGATCATCTTCCTGGGAAAGGGAACCTCAGCCGCAGATGCGGTTGAAGTGC

CAGCTCCGGCTGCAGTGCTTGGTGGACCCGAGCCTCTTATGCAAGCAACGGCATGG

CTTAATGCTTATTTTCACCAGCCTGAGGCCATTGAAGAGTTTCCAGTTCCTGCATTGC

ATCACCCCGTTTTTCAGCAGGAATCCTTCACTAGACAAGTGCTTTGGAAGCTCTTGA

AAGTGGTTAAATTTGGGGAAGTCATCTCATACAGCCACCTTGCTGCCCTTGCAGGCA

ATCCTGCGGCCACGGCTGCAGTGAAAACTGCACTTAGCGGAAATCCAGTCCCCATC

TTGATACCGTGTCACAGGGTAGTACAGGGCGACCTGGACGTCGGCGGTTACGAGGG

CGGTTTGGCCGTTAAGGAATGGTTGCTGGCGCATGAGGGTCACCGGCTGGGAAAAC

CAGGTCTTGGTGGAGGAAGTGGAGGATCTATCCTGGACTACAGCTTCACAGGTGGC

GCT
Legend:
5' region of pHR_PGK_antiCD19_synNotch_Gal4VP64 acceptor
vector, residues 1-30 SNAPtag, residues 31-594
3' region of pHR_PGK_antiCD19_synNotch_Gal4VP64 acceptor
vector, residues 595-624

SEQ ID NO: 8: pHR-PGK-mSA2x2-synNotch-Gal4-VP64 (insert for
pHR_PGK_[]_synNotch_Gal4VP64 vector backbone)
GAGCAAAAACTTATCTCTGAAGAGGACCTCATGGACAAAGATTGCGAGATGAAGAG

AACCACCCTGGATAGCCCTCTCGGCAAGCTCGAACTTTCTGGTTGTGAACAGGGTTT

-continued

GCACAGGATCATCTTCCTGGGAAAGGGAACCTCAGCCGCAGATGCGGTTGAAGTGC

CAGCTCCGGCTGCAGTGCTTGGTGGACCCGAGCCTCTTATGCAAGCAACGGCATGG

CTTAATGCTTATTTTCACCAGCCTGAGGCCATTGAAGAGTTTCCAGTTCCTGCATTGC

ATCACCCCGTTTTTCAGCAGGAATCCTTCACTAGACAAGTGCTTTGGAAGCTCTTGA

AAGTGGTTAAATTTGGGGAAGTCATCTCATACAGCCACCTTGCTGCCCTTGCAGGCA

ATCCTGCGGCCACGGCTGCAGTGAAAACTGCACTTAGCGGAAATCCAGTCCCCATC

TTGATACCGTGTCACAGGGTAGTACAGGGCGACCTGGACGTCGGCGGTTACGAGGG

CGGTTTGGCCGTTAAGGAATGGTTGCTGGCGCATGAGGGTCACCGGCTGGGAAAAC

CAGGTCTTGGTGGAGGAAGTGGAGGATCTATCCTGGACTACAGCTTCACAGGTGGC

GCT

Legend:
5' region of pHR_PGK_antiCD19_synNotch_Gal4VP64 acceptor
vector, residues 1-30 mSA2x2, residues 31-807
3' region of pHR_PGK_antiCD19_synNotch_Gal4VP64 acceptor
vector, residues 807-837

SEQ ID NO: 9 pHR-pGal-IL7-PGK-mCherry (insert for
pHR_Gal4UAS_[]_PGK_mCherry vector backbone)
CCGATCCAGCCTCTCGACATTCGTTGGATCATGTTCCACGTAAGTTTCAGATATATC

TTTGGACTTCCGCCGCTCATATTGGTATTGTTGCCAGTGGCATCTAGTGACTGTGAC

ATAGAAGGAAAGGATGGTAAACAGTATGAAAGCGTACTTATGGTATCCATTGACCA

GCTTCTCGATAGTATGAAAGAGATTGGTAGTAATTGCCTCAATAACGAGTTCAATTT

CTTTAAACGACACATTTGTGATGCGAATAAAGAGGGAATGTTTCTGTTTCGCGCCGC

GAGGAAGCTTAGGCAGTTCCTTAAAATGAACTCAACTGGGGATTTCGACCTCCATCT

GCTGAAGGTGAGTGAAGGTACTACTATTCTCCTGAATTGCACGGGACAGGTAAAGG

GGCGAAAACCTGCGGCCTTGGGTGAGGCACAACCAACCAAAAGCCTCGAAGAAAA

CAAGTCCCTCAAAGAACAGAAGAAGCTCAACGATCTGTGCTTTCTGAAAAGACTCT

TGCAGGAGATCAAAACTTGTTGGAATAAGATTTTGATGGGCACTAAGGAGCATTAA

GATCCTTGACTTGCGGCCGCAACTCCC

Legend:
5' region of pHR_Gal4UAS_[]_PGK_mCherry acceptor
vector, residues 1-30 IL-7, residues 31-531
3' region of pHR_PGK_antiCD19_synNotch_Gal4VP64 acceptor
vector, residues 532-591

---

What is claimed is:

1. A universal chimeric antigen receptor (CAR), wherein the CAR comprises an adaptor molecule, a CD8α hinge domain, and a CD3ζ signaling domain, wherein the adaptor molecule comprises a modified O-6-methylguanine-DNA methyltransferase (protein SNAP-tag) that reacts specifically with $O^6$-benzylguanine (BG), and wherein the protein SNAP-tag is covalently linked to an antibody or antigen-binding fragment thereof comprising one or more BGs.

2. The universal CAR of claim 1, wherein the antibody or antigen binding fragment thereof comprises rituximab, cetuximab, nimotuzumab, panitumumab, omalizumab, tositumomab, trastuzumab, gemtuzumab, alemtuzumab, bevacuzimab or an antigen-binding fragment of any one thereof.

3. The universal CAR of claim 1, further comprising one or more co-stimulation domains.

4. The universal CAR of claim 3, wherein the one or more co-stimulation domains comprise signaling domains for CD27, CD28, ICOS, 4-1BB, or OX40.

5. A CAR T cell comprising the universal CAR of claim 1.

6. A method of treating a cancer in a subject comprising administering to the subject
   a CAR T cell comprising a universal chimeric antigen receptor (CAR), wherein the CAR comprises an adaptor molecule, a CD8& hinge domain, and a CD35 signaling domain, wherein the adaptor molecule comprises a first modified O-6-methylguanine-DNA methyltransferase (protein SNAP-tag) that reacts specifically with $O^6$-benzylguanine (BG) and wherein the first protein SNAP-tag is covalently linked to an antibody or antigen-binding fragment thereof comprising one or more BGs, wherein the antibody or antigen binding fragment thereof comprises rituximab, trastuzumab, or cetuximab.

7. The method of claim 6, wherein the antibody or antigen-binding fragment thereof comprises rituximab and the cancer is non-Hodgkins lymphoma.

8. The method of claim 6, wherein the antibody or antigen-binding fragment thereof comprises Herceptin and the cancer is breast or ovarian cancer.

9. The method of claim 6, wherein the antibody or antigen-binding fragment thereof comprises cetuximab and the cancer is head and neck cancer.

10. The universal CAR of claim 1, wherein the adaptor molecule further comprises a short peptide tag to which the BG is linked.

* * * * *